US011969433B2

(12) United States Patent
Blau et al.

(10) Patent No.: US 11,969,433 B2
(45) Date of Patent: *Apr. 30, 2024

(54) COMPOSITIONS AND METHODS FOR MUSCLE REGENERATION USING PROSTAGLANDIN E2

(71) Applicant: The Board of Trustees of the Leland Stanford Junior University, Stanford, CA (US)

(72) Inventors: Helen M. Blau, Stanford, CA (US); Andrew Tri Van Ho, Stanford, CA (US); Adelaida R. Palla, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 677 days.

This patent is subject to a terminal disclaimer.

(21) Appl. No.: 16/548,531

(22) Filed: Aug. 22, 2019

(65) Prior Publication Data

US 2020/0147103 A1 May 14, 2020

Related U.S. Application Data

(63) Continuation of application No. 15/891,278, filed on Feb. 7, 2018, now Pat. No. 10,449,205, which is a continuation of application No. 15/498,293, filed on Apr. 26, 2017, now Pat. No. 9,918,994, which is a continuation of application No. PCT/US2017/020650, filed on Mar. 3, 2017.

(60) Provisional application No. 62/348,116, filed on Jun. 9, 2016, provisional application No. 62/303,979, filed on Mar. 4, 2016.

(51) Int. Cl.
| | | |
|---|---|---|
| A61K 35/34 | (2015.01) | |
| A61K 31/5575 | (2006.01) | |
| C12N 5/077 | (2010.01) | |
| A61P 9/10 | (2006.01) | |
| A61P 21/00 | (2006.01) | |

(52) U.S. Cl.
CPC .......... *A61K 31/5575* (2013.01); *A61K 35/34* (2013.01); *C12N 5/0658* (2013.01); *A61P 9/10* (2018.01); *A61P 21/00* (2018.01); *C12N 2501/02* (2013.01)

(58) Field of Classification Search
None
See application file for complete search history.

(56) References Cited

U.S. PATENT DOCUMENTS

| | | |
|---|---|---|
| 3,927,213 A | 12/1975 | Lippmann |
| 5,466,676 A | 11/1995 | Booth et al. |
| 5,599,561 A | 2/1997 | Gonzalez, Jr. |
| 5,736,396 A | 4/1998 | Bruder et al. |
| 5,833,978 A | 11/1998 | Tremblay |
| 5,942,225 A | 8/1999 | Bruder et al. |
| 5,962,528 A | 10/1999 | Scott |
| 6,841,573 B2 | 1/2005 | Llewellyn |
| 7,632,848 B1 | 12/2009 | Scott |
| 7,772,433 B2 | 8/2010 | Dalton et al. |
| 8,193,220 B1 | 6/2012 | Scott |
| 8,227,466 B2 | 7/2012 | Schuster et al. |
| 8,436,026 B2 | 5/2013 | Sakai et al. |
| 9,248,185 B2 | 2/2016 | Rubin et al. |
| 9,649,350 B2 | 5/2017 | Choi et al. |
| 9,660,998 B1 | 5/2017 | Sethi |
| 9,782,417 B2 | 10/2017 | Rubin et al. |
| 9,918,994 B2 | 3/2018 | Blau et al. |
| 10,449,205 B2 | 10/2019 | Blau et al. |
| 2011/0004589 A1 | 1/2011 | Rischar et al. |
| 2012/0282242 A1 | 11/2012 | Abreu |
| 2013/0236433 A1 | 9/2013 | Webster |
| 2013/0331389 A1 | 12/2013 | Hsieh et al. |
| 2014/0348802 A1 | 11/2014 | Shoemaker et al. |
| 2015/0072998 A1 | 3/2015 | Markowitz et al. |
| 2017/0252354 A1 | 9/2017 | Blau et al. |
| 2018/0177799 A1 | 6/2018 | Blau et al. |
| 2018/0200264 A1 | 7/2018 | Blau et al. |
| 2019/0167695 A1 | 6/2019 | Blau et al. |

(Continued)

FOREIGN PATENT DOCUMENTS

| | | |
|---|---|---|
| CN | 101495623 A | 7/2009 |
| CN | 102014921 A | 4/2011 |
| WO | 9628541 A1 | 9/1996 |

(Continued)

OTHER PUBLICATIONS

Cho et al (Prostaglandins, Leukotrienes and Essential Fatty Acids 67:431-465, 2002) (Year: 2002).*
Hsu et al (Radiat Res 149:482-486, 1998—Abstract only) (Year: 1998).*
Zhang et al (Science 348(6240):aaa2340-1 to aaa2340-8, 2015) (Year: 2015).*
EP18813514.9, Extended European Search Report, dated May 12, 2021, 10 pages.
Ho et al., "Prostaglandin E2 is Essential For Efficacious Skeletal Muscle Stem-Cell Function, Augmenting Regeneration and Strength," Proc Natl Acad Sci U S A, vol. 114, No. 26, 2017, pp. 1-11.

(Continued)

*Primary Examiner* — Craig D Ricci
(74) *Attorney, Agent, or Firm* — Kilpatrick Townsend & Stockton LLP

(57) ABSTRACT

Provided herein are compositions, methods, and kits for proliferating muscle cells by exposing the muscle cells to a prostaglandin E2 (PGE2) compound or compound that activates PGE2 signaling. Also provided are methods for regenerating muscle in a subject suffering from muscular atrophy, dystrophy, and/or injury by administering a PGE2 compound alone or in combination with isolated muscle cells. The PGE2 compound in combination with the isolated muscle cells can be administered prophylactically to prevent a muscle disease or condition.

7 Claims, 21 Drawing Sheets

Specification includes a Sequence Listing.

(56) References Cited

U.S. PATENT DOCUMENTS

| | | |
|---|---|---|
| 2020/0147103 A1 | 5/2020 | Blau et al. |
| 2022/0265677 A1 | 8/2022 | Blau et al. |

FOREIGN PATENT DOCUMENTS

| | | | | |
|---|---|---|---|---|
| WO | WO 2008/57753 | * | 12/2008 | ............ A61K 31/70 |
| WO | 2015065716 A1 | | 5/2015 | |
| WO | WO 2015/065716 | * | 5/2015 | ........... C07D 495/04 |
| WO | 2016123117 A1 | | 8/2016 | |
| WO | 2017152044 A1 | | 9/2017 | |
| WO | 2018227134 A1 | | 12/2018 | |
| WO | 2018227138 A1 | | 12/2018 | |

OTHER PUBLICATIONS

Scott et al., "Bupivacaine Injection of the Lateral Rectus Muscle to Treat Esotropia", Journal of AAPOS, vol. 13, Issue 2, 2009, pp. 119-122.

Arnold et al., "Inflammatory Monocytes Recruited after Skeletal Muscle Injury Switch into Anti-inflammatory Macrophages to Support Myogenesis," The Journal of experimental medicine, vol. 204, 2007, pp. 1057-1069.

Baracos et al., "Stimulation of Muscle Protein Degradation and Prostaglandin E2 Release by Leukocytic Pyrogen (Interleukin-1)," A Mechanism for the Increased Degradation of Muscle Proteins during Fever, vol. 308, No. 10, 1983, pp. 553-558.

Beaulieu et al., "Abnormal Prostaglandin E2 Production Blocks Myogenic Differentiation in Myotonic Dystrophy," Neurobiology of Disease, vol. 45, 2012, pp. 122-129.

"11-deoxy-16, 16-dimethyl-PGE2," PubChem, Available on Internet at:<https://pubchem.ncbi.nlm.nih.gov/compound/5283063#section=Top>, 2006, 14 pages.

"Bupivacaine Versus Lidocaine Local Anesthesia," University of British Columbia, Dec. 14, 2015, 5 pages.

Dinoprostone. Datasheet [online]. PubChem, 2004 Retrieved from Internet. Available on Internet at: URL:https://pubchem.ncbi.nlm.nih.gov/compound/5280360#section=Top. (Year: 2004) 42 pages.

Ono-AE3-208, PubChem, 2006 Available on Internet at:: https://pubchem .ncbi.nlm.nih .gov/compound/ono-ae3-208#section=Top (Year: 2006) 17 pages.

Prostaglandin E2 Sodium Salt. Datasheet. PubChem, Available Online at: https://pubchem.ncbi.nlm.nih.gov/compound/23667543, Feb. 5, 2008, 11 pages.

Sulprostone. Datasheet [online]. PubChem, 2005. CID: 5312153, Available Online at : https://pubchem.ncbi.nlm.nih.gov/compound/5312153#section=Top> (Year: 2005), pp. 1-19.

Sulprostone. Datasheet [online], Catalogue No. 3049, Tocris, 2018, Available Online at : https://www.tocris.com/products/sulprostone_3049, (Year: 2018), pp. 1-2.

Bernet et al., "p38 MAPK Signaling Underlies a Cell-Autonomous Loss of Stem Cell Self-Renewal in Skeletal Muscle of Aged Mice," Nature medicine, vol. 20, 2014, pp. 265-271.

Burkholder et al., "Relationship Between Muscle Fiber Types and Sizes and Muscle Architectural Properties in the Mouse Hindlimb," Journal of Morphology, vol. 221, 1994, pp. 177-190.

Chakkalakal et al., "The Aged Niche Disrupts Muscle Stem Cell Quiescence," Nature, vol. 490, 2012, pp. 355-360.

Chazaud et al., "Inflammation During Skeletal Muscle Regeneration and Tissue Remodeling: Application to Exercise-Induced Muscle Damage Management," Immunol Cell Biology, vol. 94, 2016, pp. 140-145.

Chenouard et al., "Objective Comparison of Particle Tracking Methods," Nature methods, vol. 11, 2014, pp. 281-289.

Cherng et al., "Intramuscular Bupivacaine Injection Dose-dependently Increases Glutamate Release and Muscle Injury in Rats," Taiwan Society of Anesthesiologists, vol. 48, No. 1, 2010, pp. 8-14.

Cosgrove et al., "Rejuvenation of the Muscle Stem Cell Population Restores Strength to Injured Aged Muscles," Nature medicine, vol. 20, 2014, pp. 255-264.

Costamagna et al., "Adult Stem Cells and Skeletal Muscle Regeneration," Current Gene Therapy, vol. 15, No. 4, 2015, pp. 348-363.

Crameri et al., "Changes in Satellite Cells in Human Skeletal Muscle after a Single Bout of High Intensity Exercise," The Journal of Physiology, vol. 558, 2004, pp. 333-340.

Darr et al., "Exercise-Induced Satellite Cell Activation in Growing and Mature Skeletal Muscle," Journal of Applied Physiology, vol. 63, 1987, pp. 1816-1821.

Debert et al., "Pharmacologic Injection Treatment of Comitant Strabismus," J AAPOS, Author manuscript, vol. 20, No. 2, Apr. 2016, pp. 1-14.

Dolkart et al., "Statins Enhance Rotator Cuff Healing by Stimulating the COX2/PGE2/EP4 Pathway," The American Journal of Sports Medicine, vol. 42, No. 12, 2014, pp. 2869-2876.

Dreyer et al., "Satellite Cell Numbers in Young and Older Men 24 Hours after Eccentric Exercise," Muscle & Nerve, vol. 33, 2006, pp. 242-253.

EP17760893.2, "Extended European Search Report," dated Aug. 2, 2019, 10 pages.

Ferry et al., "Effect of Prostaglandin E2 Injection on the Structural Properties of the Rat Patellar Tendon," Sports Medicine, Arthroscopy, Rehabilitation, Therapy & Technology, vol. 4, No. 2, 2012, pp. 1-9.

Gilbert, "Substrate Elasticity Regulates Skeletal Muscle Stem Cell Self-Renewal in Culture," Science, vol. 329, 2010, pp. 1078-1081.

Gupta et al., "Salts of Therapeutic Agents: Chemical, Physiocochemical, and Biological Considerations," Molecules, MDPI, vol. 23, No. 7, Jul. 14, 2018, 15 pages.

Han et al., "Persistent Diplopia after Retrobulbar Anesthesia," J Cataract Refract Surg, vol. 30, Jun. 2004, pp. 1248-1253.

Joe et al., "Muscle Injury Activates Resident Fibro/Adipogenic Progenitors that Facilitate Myogenesis," Nature Cell Biology, vol. 12, 2010, pp. 153-163.

Johnson et al., "Local Anesthetics as Antimicrobial Agents: A Review," Surgical Infections, vol. 9, No. 2, Apr. 21, 2008, pp. 205-213.

Khan et al., "Repeated Exposure of Tendon to Prostaglandin-E2 Leads to Localized Tendon Degeneration," Clin J Sport Med, vol. 15, No. 1, 2005, 27-33.

Korotkova et al., "The Skeletal Muscle Arachidonic Acid Cascade in Health and Inflammatory Disease," Nature Reviews, Rheumatology, vol. 10, 2014, pp. 295-303.

Kuang, "Niche Regulation of Muscle Satellite Cell Self-Renewal and Differentiation," Cell stem cell 2, 2007, pp. 22-31.

Mackey et al., "The Influence of Anti-Inflammatory Medication on Exercise-Induced Myogenic Precursor Cell Responses in Humans," Journal of Applied Physiology vol. 103, 2007, pp. 425-431.

Magnusson et al., "Global Linking of Cell Tracks Using the Viterbi Algorithm," IEEE Transactions on Medical Imaging, vol. 34, 2015, pp. 911-929.

Maska et al., "A Benchmark for Comparison of Cell Tracking Algorithms," Bioinformatics, vol. 30, 2014, pp. 1609-1617.

Mauro et al., "Satellite Cell of Skeletal Muscle Fibers," J Biophys Biochem Cytol, vol. 9, Feb. 1, 1961, pp. 493-495.

Miller et al., "Bupivacaine Injection Remodels Extraocular Muscles and Corrects Comitant Strabismus," Authors' Cut, 2013, pp. 1-11.

Mo et al., "Prostaglandin E2 Promotes Proliferation Of Skeletal Muscle Myoblasts Via Ep4 Receptor Activation," Cell cycle, vol. 14, 2015, pp. 1507-1516.

Mo et al., "Prostaglandin E2: From Clinical Applications to its Potential Role in Bone-Muscle Crosstalk and Myogenic Differentiation," Recent Patents on Biotechnology, vol. 6, No. 3, 2012, pp. 223-229.

Monaco et al., "Prevalence of Sarcopenia and its Association with Osteoporosis in 313 Older Women Following a Hip Fracture," Archives of Gerontology and Geriatrics, vol. 52, 2010, pp. 71-74.

Montarras et al., "Direct Isolation of Satellite Cells for Skeletal Muscle Regeneration," Science, vol. 309, 2005, pp. 2064-2067.

(56) References Cited

OTHER PUBLICATIONS

Murphy et al., "Satellite Cells, Connective Tissue Fibroblasts and their Interactions are Crucial for Muscle Regeneration," Development vol. 138, May 27, 2011, pp. 3625-3637.
North et al., "Prostaglandin E2 Regulates Vertebrate Haematopoietic Stem Cell Homeostasis," Nature, vol. 447, Jun. 21, 2007, pp. 1007-1011.
Ohno et al., "Studies on 15-Hydroxyprostaglandin Dehydrogenase with Various Prostaglandin Analogues," Journal of biochemistry, vol. 84, May 25, 1978, pp. 1485-1494.
ONO AE3 208 , "Datasheet [Online]. Tocris," Retrieved from the Internet: < https://www.tocris.com/products/ono-ae3-208_3565>, [Retrieved on Oct. 15, 2018], 2018.
Otis et al., "Stretch-induced Myoblast Proliferation is Dependent on the COX2 Pathway," Experimental Cell Research, vol. 310, No. 2, Nov. 1, 2005, pp. 417-425.
Papapetrou et al., "Genomic Safe Harbors Permit High Beta-Globin Transgene Expression in Thalassemia Induced Pluripotent Stem Cells," Nature biotechnology, vol. 29, No. 1, Jan. 2011, pp. 73-78.
Paulsen et al., "Leucocytes, Cytokines and Satellite Cells: What Role Do They Play in Muscle Damage and Regeneration Following Eccentric Exercise?", Exercise immunology review, vol. 18, 2012, pp. 42-97.
Pawlikowski , "Pervasive Satellite Cell Contribution to Uninjured Adult Muscle Fibers," Skeletal muscle, vol. 5, No. 42, 2015, 13 pages.
Prasain , "Prostaglandin Extraction and Analysis in Caenorhabditis Elegans," Journal of visualized experiments : Jove vol. 76, Jun. 23, 2013, 8 pages.
Price et al., "Inhibition of JAK-STAT Signaling Stimulates Adult Satellite Cell Function," Nature medicine, vol. 20, No. 10, 2014, pp. 1174-1181.
Ricciotti et al., "Prostaglandins and Inflammation," Arteriosclerosis, Thrombosis, and Vascular Biology vol. 31, May 2011, pp. 986-1000.
Rodemann et al., "Arachidonic Acid, Prostaglandin E2 And F2 Alpha Influence Rates of Protein Turnover in Skeletal and Cardiac Muscle," The Journal of Biological Chemistry, vol. 257, No. 4, Aug. 18, 1982, pp. 1632-1638.
Rosa et al., "Clinical Effectiveness of Lidocaine and Benzocaine for Topical Anesthesia," Anesthesia Progress, vol. 46, No. 3, 1999, pp. 97-99.
Ruiz et al., "Association Between Muscular Strength and Mortality in Men: Prospective Cohort Study," BMJ vol. 337, 2008, 9 pages.
Sacco et al., "Self-Renewal and Expansion of Single Transplanted Muscle Stem Cells," Nature, vol. 456, 2008, pp. 502-506.
Sacco et al., "Short Telomeres and Stem Cell Exhaustion Model Duchenne Muscular Dystrophy in Mdx/Mtr Mice," Cell, vol. 143, 2010, pp. 1059-1071.
Safran et al., "Mouse Reporter Strain for Noninvasive Bioluminescent Imaging of Cells that Have Undergone Cre-Mediated Recombination," Molecular Imaging, vol. 2, 2003, pp. 297-302.
Schlondorff et al., "Prostaglandins and Other Arachidonic Acid Metabolites in the Kidney," Kidney International, vol. 29, 1986, pp. 108-119.
Schneider et al., "Generation of a Conditional Allele of the Mouse Prostaglandin EP4 Receptor," Genesis, vol. 40, 2004, pp. 7-14.
Schumert et al., "Effects of 16,16-dimethyl Prostaglandin E2 and Indomethacin on Leukotriene B4 and Inflammation in Rabbit Colitis," Prostaglandins, vol. 36, Issue 4, Oct. 1988, pp. 565-577.
Scott et al., "Bupivacaine Injection of Eye Muscles to Treat Strabismus," Br J Ophthalmol, vol. 91, 2007, pp. 146-148.
Shen et al., "Inhibited Skeletal Muscle Healing In Cyclooxygenase-2 Gene-Deficient Mice: The Role Of PGE2 And PGF2alpha," Journal of Applied Physiology, vol. 101, No. 4, Jun. 15, 2006, pp. 1215-1221.
Shi, "Muscle Stem Cells in Development, Regeneration, and Disease," Genes & Development, vol. 20, 2006, pp. 1692-1708.

Smethurst et al., "Levels of Prostaglandin E and Prostaglandin F in Samples of Commercial Serum Used for Tissue Culture," Prostaglandins, vol. 13, 1977, pp. 719-722.
Sousa et al., "Geriatric Muscle Stem Cells Switch Reversible Quiescence into Senescence," Nature, vol. 506, 2014, pp. 316-321.
Thomas et al., "Vaginal Prostaglandin (PGE2 and PGF2a) for Induction of Labour at Term," The Cochrane Database of Systematic Reviews, vol. 6, 2014, pp. 1-398.
Tidball et al., "Mechanisms of Muscle Injury, Repair, and Regeneration," Comprehensive Physiology, 2011, pp. 2029-2062.
Tierney et al., "STAT3 Signaling Controls Satellite Cell Expansion and Skeletal Muscle Repair," Nature medicine, vol. 20, 2014, pp. 1182-1186.
Ulmsten et al., "Intracervical Application of Prostaglandin Gel for Induction of Term Labor," Obstetrics & Gynecology, vol. 59, No. 3, Mar. 1982, pp. 336-339.
Zhang et al., "Inhibition of the Prostaglandin-Degrading Enzyme 15-PGDH Potentiates Tissue Regeneration," Science, vol. 348, No. 6240, 2015, 10 pages.
Ziboh et al., "Effects of Prostaglandin E2 on Rat Skin: Inhibition of Sterol Ester Biosynthesis and Clearing of Scaly Lesions in Essential Fatty Acid Deficiency," Journal of Lipid Research, vol. 13, 1972, pp. 458-467.
U.S. Appl. No. 15/498,293, "Non-Final Office Action," dated Jul. 19, 2017, 10 pages.
U.S. Appl. No. 15/498,293, "Notice of Allowance," dated Jan. 12, 2018, 8 pages.
U.S. Appl. No. 16/148,976, "Non-Final Office Action," dated May 15, 2019, 15 pages.
PCT/US2017/020650, "International Preliminary Report on Patentability," dated Sep. 13, 2018, 11 pages.
PCT/US2017/020650, "International Search Report and Written Opinion," dated Jun. 19, 2017, 14 pages.
PCT/US2018/036727, "International Search Report and Written Opinion," dated Oct. 19, 2018, 13 pages.
PCT/US2018/036727, "Invitation to Pay Add'l Fees and Partial Search Report," dated Aug. 24, 2018, 2 pages.
PCT/US2018/036731, "International Search Report and Written Opinion," dated Sep. 7, 2018, 9 pages.
U.S. Appl. No. 15/916,779, "Final Office Action," dated Oct. 18, 2018, 14 pages.
U.S. Appl. No. 15/916,779, "First Action Interview Office Action Summary," dated Jul. 27, 2018, 5 pages.
U.S. Appl. No. 15/916,779, "First Action Interview Pilot Program Pre-Interview Communication," dated Jun. 19, 2018, 4 pages.
U.S. Appl. No. 15/916,779, "Non-Final Office Action," dated May 7, 2019, 15 pages.
U.S. Appl. No. 15/891,278, "Corrected Notice of Allowability," dated Oct. 8, 2019, 3 pages.
U.S. Appl. No. 15/891,278, "Corrected Notice of Allowability," dated Sep. 17, 2019, 3 pages.
U.S. Appl. No. 15/891,278, "Final Office Action," dated Oct. 16, 2018, 9 pages.
U.S. Appl. No. 15/891,278, "First Action Interview Office Action Summary," dated Jul. 27, 2018, 5 pages.
U.S. Appl. No. 15/891,278, "First Action Interview Pilot Program Pre-Interview Communication," dated Jun. 19, 2018, 4 pages.
U.S. Appl. No. 15/891,278, "Non-Final Office Action," dated Apr. 24, 2019, 6 pages.
U.S. Appl. No. 15/891,278, "Notice of Allowance," dated Jun. 10, 2019, 6 pages.
U.S. Appl. No. 16/148,976, "Final Office Action," dated Nov. 4, 2019, 16 pages.
U.S. Appl. No. 15/916,779, "Final Office Action," dated Oct. 24, 2019, 8 pages.
U.S. Appl. No. 16/148,976, "Non-Final Office Action," dated Jul. 9, 2020, 18 pages.
U.S. Appl. No. 16/148,976, "Final Office Action," dated Feb. 12, 2021, 26 pages.
PCT/US2018/036727, "International Preliminary Report on Patentability," dated Dec. 19, 2019, 17 pages.
PCT/US2018/036731, "International Preliminary Report on Patentability," dated Dec. 19, 2019, 7 pages.

(56) References Cited

OTHER PUBLICATIONS

Carlson et al., "A Histological Study of Local Anesthetic-Induced Muscle Degeneration and Regeneration in the Monkey," Journal of Orthopaedic Research, vol. 8, 1990, pp. 485-494.
Miller et al., Ophthalmology, vol. 120, 2013, pp. 2733-2740.
Murray, Middle East Afr. J. Ophthalmol., vol. 22(3), 2015, pp. 312-319.
Dingfelder et al., "The Thermogenic Activity of Exogenous E and F Prostaglandins in Humans," Acta Obstet. Gynecol. Scand., vol. 57, 1978, pp. 35-40.
EP18813514.9, "Partial Supplementary European Search Report," dated Feb. 10, 2021, 11 pages.
Palla et al., "Inhibition of prostaglandin-degrading enzyme 15-PGDH rejuvenates aged muscle mass and strength," Science, 371, eabc8059, Jan. 29, 2021, 13 pages.
U.S. Appl. No. 17/399,490, Non-Final Office Action, dated Apr. 29, 2022, 6 pages.
Kim, Y. et al., "Clinical Report of Oriental Medicine Treatment with Bee Venom Therapy of Progressive Muscle Atrophy 1 Patient," J. of Korean Institute of Herbal-Acupuncture, 3(1):119-140, 2000, English Abstract.
U.S. Appl. No. 17/399,490, Non-Final Office Action, dated Aug. 16, 2022, 9 pages.
Loi et al., "Steady-State Pharmacokinetics and Dose Proportionality of Troglitazone and Its Metabolites," J. Clin. Pharmacol., 39-920-926, 1999.
U.S. Appl. No. 17/399,490, Notice of Allowance, dated Feb. 16, 2023, 21 pages.

\* cited by examiner

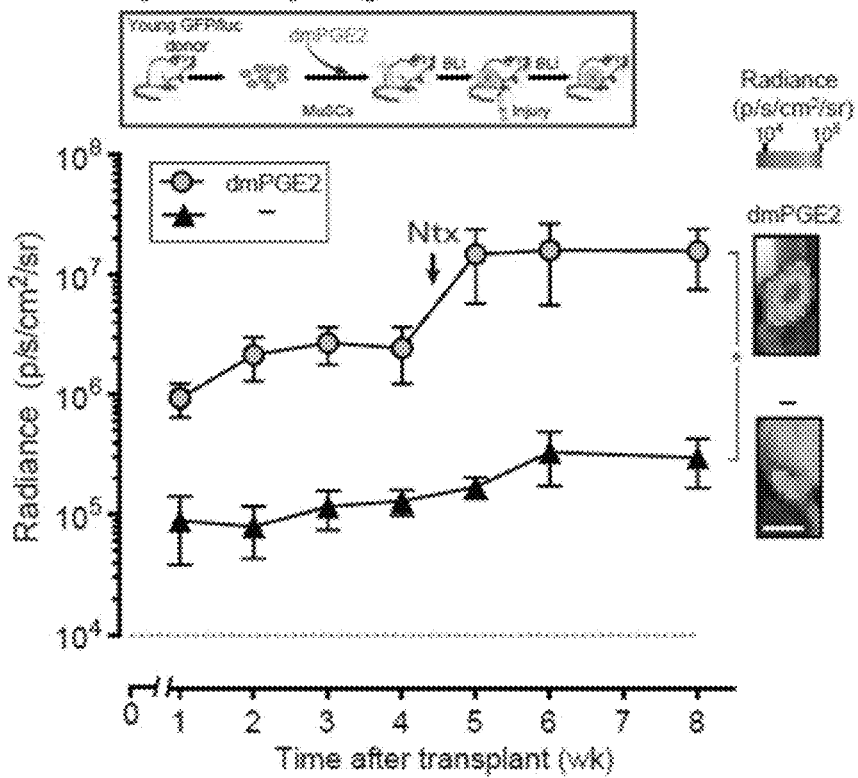
FIG. 3C Coinjection of young MuSCs + dmPGE2
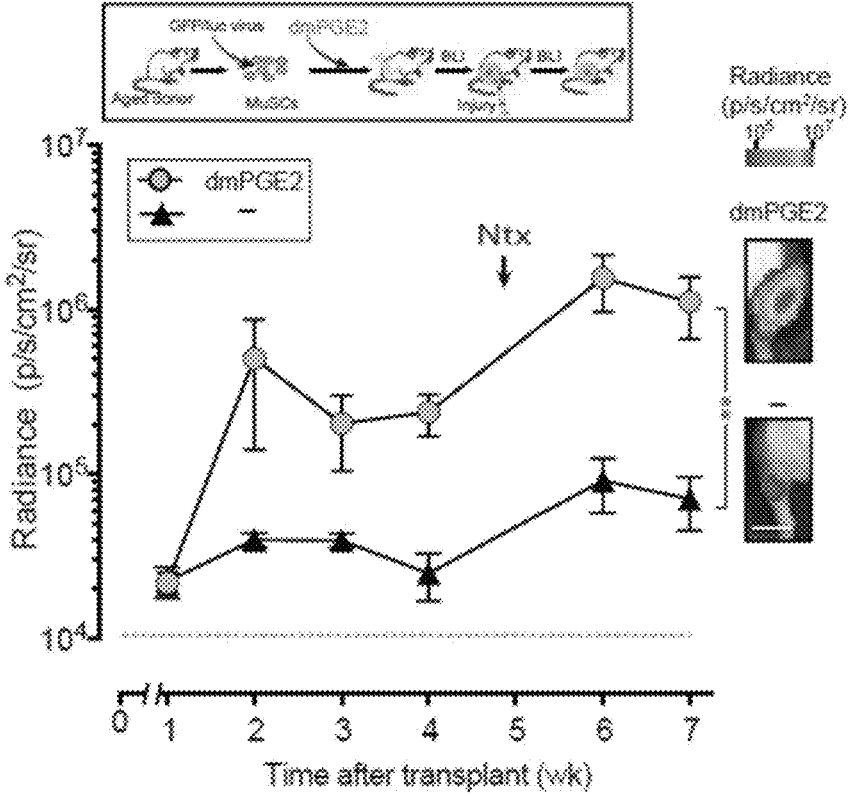
FIG. 3D Coinjection of aged MuSCs + dmPGE2

Injection of dmPGE2 only (young mice)

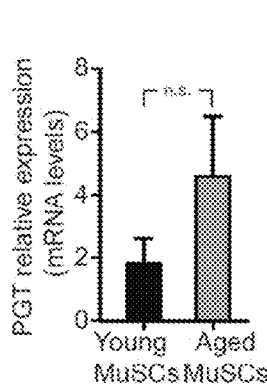 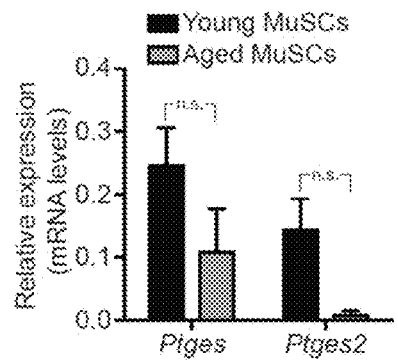
FIG. 7A    FIG. 7B
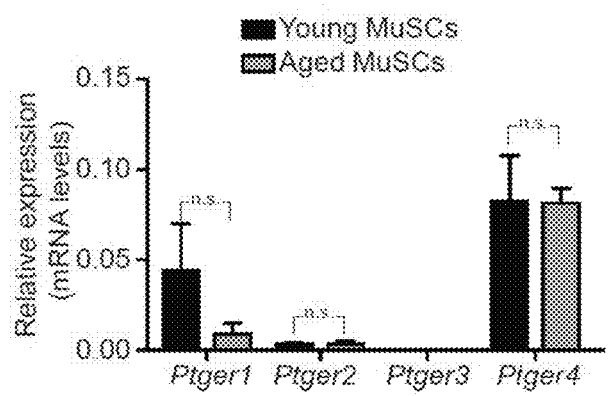 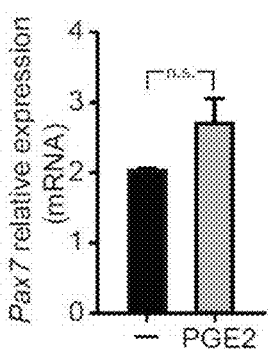
FIG. 7C    FIG. 7D
FIG. 7E
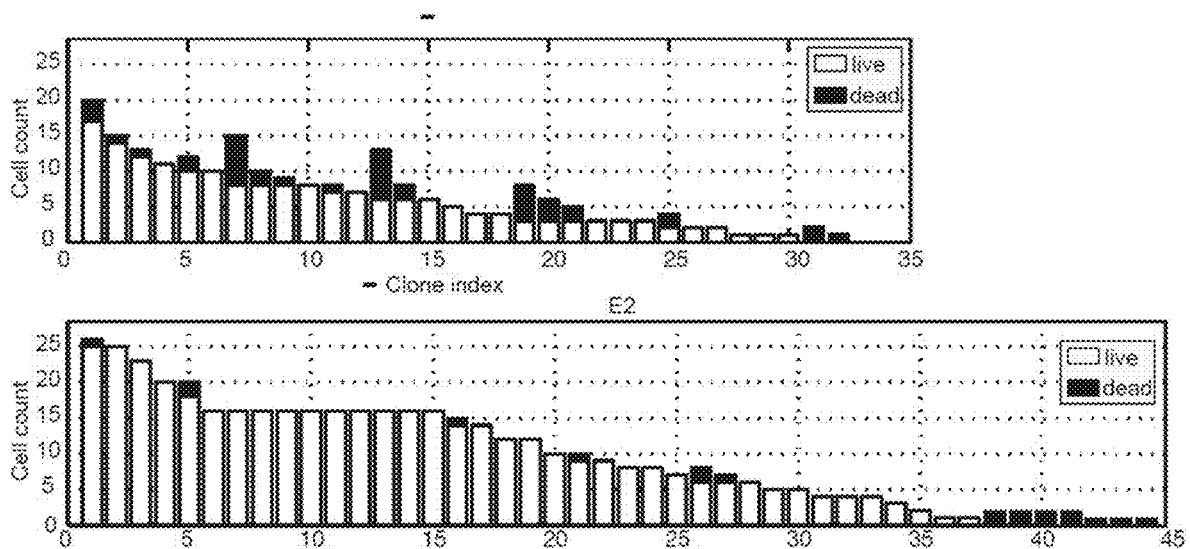

Immunofluorescent staining of myofibers in TA cross-section

Myofiber segmentation for quantification of cross sectional area (CSA)

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic Gapdh forward primer

<400> SEQUENCE: 1
ttcaccacca tggagaaggc              20

<210> SEQ ID NO 2
<211> LENGTH: 18
<212> TYPE: DNA
<213> ORGANISM: Artificial Sequence
<220> FEATURE:
<223> OTHER INFORMATION: Synthetic Gapdh reverse primer

<400> SEQUENCE: 2 ccctttggc tccaccct                 18

<210> SEQ ID NO 3
<211> LENGTH: 20
<212> TYPE: DNA
<213> ORGANISM: Artificial Sequence
<220> FEATURE:
<223> OTHER INFORMATION: Synthetic Hpgd forward primer

<400> SEQUENCE: 3
tccagtgtga tgtggctgac              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Hpgd reverse primer

<400> SEQUENCE: 4
attgttcacg cctgcattgt              20

<210> SEQ ID NO 5
<211> LENGTH: 19
<212> TYPE: DNA
<213> ORGANISM: Artificial Sequence
<220> FEATURE:
<223> OTHER INFORMATION: Synthetic Ptges forward primer

<400> SEQUENCE: 5
gctgtcatca caggccaga               19

<210> SEQ ID NO 6
<211> LENGTH: 20
<212> TYPE: DNA
<213> ORGANISM: Artificial Sequence

```
<220> FEATURE:
<223> OTHER INFORMATION: Synthetic Ptges reverse  primer

<400> SEQUENCE: 6
ctccacatct gggtcactcc                                            20

<210> SEQ ID NO 7
<211> LENGTH: 20
<212> TYPE: DNA
<213> ORGANISM: Artificial Sequence
<220> FEATURE:
<223> OTHER INFORMATION: Synthetic Ptges2 forward  primer

<400> SEQUENCE: 7
ctcctacagg aaagtgccca                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic Ptges2 reverse  primer

<400> SEQUENCE: 8
accaggtagg tcttgagggc                                            20

<210> SEQ ID NO 9
<211> LENGTH: 19
<212> TYPE: DNA
<213> ORGANISM: Artificial Sequence
<220> FEATURE:
<223> OTHER INFORMATION: Synthetic Ptger1 forward  primer

<400> SEQUENCE: 9
gtggtgtcgt gcatctgct                                             19

<210> SEQ ID NO 10
<211> LENGTH: 20
<212> TYPE: DNA
<213> ORGANISM: Artificial Sequence
<220> FEATURE:
<223> OTHER INFORMATION: Synthetic Ptger1 reverse  primer

<400> SEQUENCE: 10
ccgctgcagg gagttagagt                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic Ptger2 forward primer

<400> SEQUENCE: 11
accttcgcca tatgctcctt                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic Ptger2 reverse  primer

<400> SEQUENCE: 12
ggaccggtgg cctaagtatg                                            20
```

COMPOSITIONS AND METHODS FOR MUSCLE REGENERATION USING PROSTAGLANDIN E2

CROSS-REFERENCES TO RELATED APPLICATIONS

The present application is a continuation of U.S. Ser. No. 15/891,278 filed Feb. 7, 2018 (allowed); which is a continuation of U.S. Ser. No. 15/498,293 filed Apr. 26, 2017, now U.S. Pat. No. 9,918,994 issued on Mar. 20, 2018; which is a continuation of PCT/US2017/020650 filed Mar. 3, 2017; which claims priority to U.S. Provisional Application Nos. 62/303,979 filed Mar. 4, 2016 and 62/348,116 filed Jun. 9, 2016; the full disclosures which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. AG020961, awarded by the National Institutes of Health. The government has certain rights in the invention.

REFERENCE TO A SEQUENCE LISTING

The instant application contains a Sequence Listing which has been filed electronically in ASCII format and is hereby incorporated by reference in its entirety. Said ASCII copy, created on Aug. 21, 2019, is named 079445-1153470_SL.txt and is 2,985 bytes in size.

BACKGROUND OF THE INVENTION

In skeletal muscles, aging leads to progressively impaired regeneration and loss of muscle mass, strength and function. Loss of muscle function is a major public health problem that often leads to severe loss of mobility and impaired quality of life in the ever-increasing aged population. A major determinant of muscle functional decline is the impaired ability of skeletal muscle stem cells (MuSCs) to regenerate muscle after acute injury or damage in the course of aging. There is also a need to augment muscle regeneration in muscles that have undergone damage, injury, and/or atrophy due to, for example, postoperative immobilization or disuse, cancer and HIV cachexia, muscular dystrophies, acute injury, and aging. Resident MuSCs are rare but essential to the maintenance and repair of muscle, e.g., skeletal muscle, smooth muscle and cardiac muscle throughout adulthood. With aging, the number of functional stem cells declines and thus, the need to enhance the numbers and function of MuSCs increases.

Prostaglandin E2 (PGE2), also known as dinoprostone, has been employed in various clinical settings including to induce labor in women and to augment hematopoietic stem cell transplantation. PGE2 can be used as an anticoagulant and antithrombotic agent. PGE2's role as a lipid mediator that can resolve inflammation is also well known. Nonsteroidal anti-inflammatory drugs (NSAIDs), inhibitors of COX-1 and/or COX-2, suppress inflammation by inhibiting prostanoids, mainly via PGE2 biosynthesis.

PGE2 is synthesized from arachidonic acid by a cyclooxygenase (COX) and prostaglandin E synthase enzymes. Levels of PGE2 are physiologically regulated by the PGE2 degrading enzyme, 15-hydroxyprostaglandin dehydrogenase (15-PGDH). 15-PGDH catalyzes the inactivating conversion of the PGE2 15-OH to a 15-keto group.

There remains a need in the art for effective treatments for regenerating or rejuvenating damaged, impaired, dysfunctional, and/or atrophied muscle in a subject in need thereof. The present invention satisfies this need and provides advantages as well.

BRIEF SUMMARY OF THE INVENTION

In one aspect of the present invention, provided herein is a method for stimulating the proliferation of a population of isolated muscle stem cells. The method includes culturing the population of isolated muscle cells with a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof.

In a second aspect of the present invention, provided herein is a composition comprising a population of isolated muscle cells and a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof.

In a third aspect of the present invention, provided herein is a kit comprising the composition comprising a population of isolated muscle cells and a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and an instruction manual.

In a fourth aspect, provided herein is a method for regenerating a population of muscle cells in a subject having a condition or disease associated with muscle damage, injury, or atrophy. The method includes administering to the subject a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, to increase the population of muscle cells and/or to enhance muscle function in the subject.

In a fifth aspect, provided herein is a method for preventing or treating a condition or disease associated with muscle damage, injury or atrophy in a subject in need thereof. The method includes administering to the subject (i) a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, and (ii) a population of isolated muscle cells, to prevent or treat the condition or disease associated with muscle damage, injury, or atrophy.

Other objects, features, and advantages of the present invention will be apparent to one of skill in the art from the following detailed description and figures.

BRIEF DESCRIPTION OF THE DRAWINGS

FIG. 1A: PGE2 levels after young tibialis anterior (TA) muscle injury (notexin, NTX); controls are uninjured contralateral TAs assayed by ELISA; (n=4 mice per timepoint).

FIG. 1B: Expression of PGE2 synthesizing enzymes (Ptges2 and Ptges) by MuSCs after notexin injury by RT-qPCR, (n=3 mice per timepoint).

FIG. 1C: Increase in MuSC numbers after 24 hr treatment with vehicle (−) or PGE2 (10 ng/ml), and subsequent culture on hydrogel until day 7 (acute treatment); (n=12 mice in 4 independent experiments).

FIG. 1D: Increase in MuSC numbers after transient 24 hr treatment with vehicle (−) or PGE2 (10 ng/ml) in absence or presence of EP4 antagonist (ONO-AE3-208, 1 µM); (n=9 mice assayed in 3 independent experiments).

FIGS. 1E-1G: Proliferation of EP4 null MuSCs. EP4$^{f/f}$ (null) MuSCs were transduced with a lentiviral vector encoding GFP/luciferase and treated with lentiviral vector encoding Cre (+Cre) or without (−Cre; empty vector) to delete EP4 alelles. Subsequently MuSCs were treated with vehicle (−) or PGE2 (10 ng/ml) for 24 hr and cultured on hydrogels for three days.

FIG. 1E: Scheme depicting EP4-null MuSC analysis.

FIG. 1F: EP4 null MuSC numbers; (n=6 mice in 2 independent experiments).

FIG. 1G: Representative image. Bar=40 µm GFP, green; mCherry, red.

FIG. 1H: MuSC numbers after culture in charcoal stripped medium treated with vehicle (−) or PGE2 (10 ng/ml) every two days for 7 days on hydrogels; (n=3 mice with 3 technical replicates). *P<0.05, P<0.001, *P<0.0005 ****P<0.0001. ANOVA test with Bonferroni correction for multiple comparisons (FIGS. 1A, 1B, ID, and IF); paired t-test (FIG. 1C); Mann-Whitney test (FIG. 1H). Means+s.e.m. n.s., non-significant.

FIG. 2A: PGE2 levels after aged TA injury (notexin, NTX); controls are uninjured contralateral TAs assayed by ELISA; (n=4 mice per timepoint).

FIG. 2B: PGE2 levels in TAs of uninjured young (n=7 mice) and aged (n=5 mice) mice assayed by ELISA.

FIG. 2C: Scheme showing PGE2 catabolism via degrading enzyme 15-PGDH to its inactive PGE metabolite, 13,14-dihydro-15-keto PGE2 (PGEM).

FIG. 2D: Levels of PGEM quantified by mass spectrometry; (n=4 mice per age group).

FIG. 2E: Expression of PGE2 degrading enzyme 15-PGDH (Hpgd); (n=3 mice with 2 technical replicates).

FIG. 2F: Increase in aged MuSC numbers after acute 24 hr treatment with vehicle (−), PGE2 (10 ng/ml) or the 15-PGDH inhibitor, SW033291 (1 µM; SW) assayed at day 7; (n=15 mice in 5 independent experiments).

FIG. 2G: Aged MuSC numbers after culture in charcoal stripped medium treated with vehicle (−) or PGE2 (10 ng/ml) every two days for 7 days on hydrogels; (n=3 mice with 3 technical replicates).

FIG. 2H: Scheme depicting PGE2 effects on MuSCs. PGE2 acts through the EP4 receptor/cAMP (cyclic AMP) signaling pathway to promote proliferation. In aged MuSCs, following intracellular transport by PGT (Prostaglandin transporter), PGE2 catabolism is mediated by 15-PGDH to the inactive form, PGEM.

FIG. 2I: Trajectories from a clone of aged MuSCs tracked by time-lapse microscopy for 48 h in a microwell for control (left) and after acute treatment with PGE2 (right). The trajectory of the original cell and each of its newborn progeny are represented by a different color.

FIG. 2J: Change in aged MuSC live cell counts (numbers) in clones tracked by time-lapse microscopy for control (left, n=32 clones) and after acute treatment with PGE2 (right, n=45 clones). The proportion of live cells in each generation (G1-G6) at all timepoints is shown as cell number normalized to a starting population of 100 single MuSCs. The percent increase in live cell count was 4.0% (control) and 5.4% (PGE2-treated) (top panels). Change in aged MuSC dead cell counts (numbers) in clones tracked by time-lapse microscopy for control (left) and after acute treatment with PGE2 (right). The proportion of dead cells in each generation (G1-G6) at all timepoints is shown as cell number normalized to a starting population of 100 single MuSCs. The percent increase in dead cell count was 1.0% (control) and 0.1% (PGE2-treated) (bottom panels). *P<0.05, P<0.001, *P<0.0005. ANOVA test with Bonferroni correction for multiple comparisons (FIGS. 2A and 2F); Mann-Whitney test (FIGS. 2B, 2D, 2E, and 2G). Means±s.e.m. n.s., non-significant.

FIGS. 3A-3D show that acute PGE2 treatment promotes MuSC engraftment and regeneration in vivo.

FIG. 3A: Engraftment of cultured GFP/luc-labeled young MuSCs (250 cells) isolated from transgenic mice after acute treatment with vehicle (−) or PGE2 as described in FIG. 1C. Transplant scheme (top). Non-invasive bioluminescence imaging (BLI) signal measured as radiance for each TA; (n=5 mice per condition) (bottom).

FIG. 3B: Engraftment of GFP/luc-labeled EP4$^{f/f}$ MuSCs (1,000 cells) treated with Cre (+Cre) or without (−Cre; empty vector) in culture to delete EP4 alelles. EP4i MuSCs were transduced with a lentiviral vector encoding GFP/luciferase for BLI. Transplant scheme (top). BLI signals post-transplant (n=5 mice per condition (bottom).

FIG. 3C: Engraftment of freshly sorted GFP/luc-labeled young MuSCs (250 cells) coinjected with vehicle (−) or dmPGE2. Transplant scheme (top). BLI signals post-transplant; (n=4 and n=5 mice for vehicle and dmPGE2 treated, respectively).

FIG. 3D: Engraftment of GFP/luc-labeled aged MuSCs (250 cells) coinjected with vehicle (−) or dmPGE2; (n=3 mice per condition) (bottom). Aged MuSCs were transduced with a lentiviral vector encoding GFP/luciferase for BLI. Transplant scheme (top). BLI signals post-transplant expressed as average radiance (p s$^{-1}$ cm$^{-2}$ sr$^{-1}$). Representative BLI images for each condition. Bar=5 mm (FIGS. 3A-3D). Data are representative of two independent experiments. * P<0.05, P<0.001 and *P<0.0005. ANOVA test for group comparisons and significant difference for endpoints by Fisher's test. Means+s.e.m.

(FIGS. 4A-4D) TA muscles of young mice were injected with vehicle (−) or dmPGE2 48 hr post-cardiotoxin (CTX) injury; (n=3 mice per condition).

FIG. 4A: Scheme of experimental procedure (top). Representative TA cross-section (bottom) with nuclei (DAPI; blue), LAMININ (green) and PAX7 (red) staining 14 days after cardiotoxin injury. Arrowheads indicate PAX7$^+$ MuSCs. Bar-40 µm.

FIG. 4B: Increase in endogenous MuSCs by immunofluorescence of PAX7 expressing satellite cells per 100 fibers in cross-sections of TAs from young mice.

FIG. 4C: Myofiber cross-sectional areas (CSA) in vehicle (−, open white bar) and dmPGE2 treated (filled blue bar) young TAs quantified using the Baxter Algorithms for Myofiber Analysis.

FIG. 4D: Distribution of small (<1,000 µm² CSA) and large (>1,000 µm² CSA) myofibers.

FIG. 4E: Scheme of experimental procedure.

FIG. 4F: BLI (n=3 mice per condition).

FIG. 4G: Representative BLI image. Bar=5 mm. Aged.

FIG. 4H: Scheme of experimental procedure (top). Representative TA cross-section (bottom) with nuclei (DAPI; blue), LAMININ (green) and PAX7 (red) staining 14 days after cardiotoxin injury. Arrowheads indicate PAX7$^+$ muscle stem cells. Bar=40 µm.

FIG. 4I: Increase in endogenous MuSCs as in FIG. 4B for aged mice.

FIG. 4J: Myofiber cross-sectional area (CSA) as in FIG. 4C for aged TAs.

FIG. 4K: Distribution of CSA as in FIG. 4D for aged TAs. (FIGS. 4L-4P) Increase in strength in aged mice measured in vivo as muscle contractile force after downhill treadmill run. Mice were subject to a 20° downhill treadmill run for 2 consecutive weeks and force was assayed at week 5. During the first week, medial and lateral gastrocnemius (GA) of aged mice were injected either with vehicle (−) or dmPGE2. n=10 or 8 biological replicates for vehicle (−) treated or dmPGE2 treated, respectively, with 5 technical replicates each.

FIG. 4L: Experimental scheme. Representative twitch force (FIG. 4M) and tetanic force (FIG. 4N). Specific muscle twitch forces (FIG. 4O) and specific muscle tetanic force (FIG. 4P) were calculated by normalizing force to physiological cross sectional areas (PCSA). Paired t-test (FIGS. 4B, 4D, 4I and 4K); ANOVA test for group comparison and significant difference for the endpoint by Fisher's test (FIG. 4F); Mann-Whitney test (FIGS. 4O and 4P). *P<0.05, P<0.001 and **P<0.0001. Means+s.e.m.

FIG. 5A: PGE2 levels day 3 after cryoinjury for tibialis anterior (TA) hindlimb muscles of young mice compared to contralateral uninjured controls as assayed by ELISA; (n=4 mice per time point per condition).

FIG. 5B: Representative image of dividing muscle stem cells (MuSCs) labelled with EdU (red) during 1 hr after treatment with PGE2 (10 ng/ml) for 24 h (d0 to d1) or vehicle (−), and stained for MYOGENIN (green). Bar represents 40 m.

FIG. 5C: Percentage of dividing MuSCs labeled with EDU as in (b); (n=6 mice with 3 technical replicates in two independent experiments).

FIG. 5D: Increase in proliferation measured by the metabolic viability assay VisionBlue after treatment with vehicle (−) or indicated doses of PGE2 (1-200 ng/ml); (n=6 mice with 3 technical replicates in two independent experiments).

FIG. 5E: Expression of prostaglandin receptors (Ptger 1-4) by MuSCs after 24 hr treatment with vehicle (−) or PGE2; (n=3 mice with 2 technical replicates).

FIG. 5F: Increase in cAMP levels in MuSCs after 1 hr PGE2 treatment relative to untreated controls (−); (n=6 mice with 3 technical replicates assayed in 2 independent experiments).

FIGS. 5G-5H: Expression of Pax7 (FIG. 5G) and Myogenin (FIG. 5H) by MuSCs after 24 hr treatment with vehicle (−) or PGE2; (n=3 mice with 2 technical replicates).

FIGS. 5I-5J: EP4$^{f/f}$ MuSCs were transduced with a lentiviral vector encoding GFP/luciferase and treated with lentiviral vector encoding Cre (+Cre) or without (−Cre; empty vector) to delete EP4 alelles. Bar graphs show percentage of +Cre MuSCs (FIG. 5I) and GFP/Luc MuSCs (FIG. 5J).

FIG. 5K: Representative image of MuSCs in hydrogel culture after 7 days in myoblast medium containing charcoal stripped fetal bovine supplemented with vehicle (−) or PGE2 (10 ng/ml) every two days. Bar represents 40 µm. *P<0.05, P<0.001, *P<0.0005. Paired t-test (FIGS. 5A, 5E, 5G, and 5H); Mann-Whitney test (FIG. 5C). Means+s.e.m. n.s., non-significant.

FIG. 6A: Chemical structures, chemical formula, exact mass and molecular weight of analyzed prostaglandins (PGE2, PGF2α and PGD2) and PGE2 metabolites (15-keto PGE2 and 13,14-dihydro-15-keto PGE2). The internal standards PGF2α-D9 and PGE2-D9 were added to all composite standards.

FIG. 6B: Calibration lines for liquid chromatography-electrospray ionization-tandem mass spectrometry (LC-ESI-MS/MS) analysis were prepared by diluting stock solutions to final concentrations of 0.1 ng/ml to 500 ng/ml. Standard curve equations and correlation coefficients are shown for each standard.

FIG. 6C: Representative chromatogram. The separate peaks show excellent chromatographic resolution of the analyzed prostaglandins and their metabolites. cps, counts per second.

FIGS. 7A-7G show that aged MuSCs increase proliferation and cell survival in response to PGE2 treatment. FIGS. 7A-7C: mRNA levels measured by qRT-PCR were normalized to Gapdh for young and aged MuSCs; (n=3 mice with 2 technical replicates).

FIG. 7A: Prostaglandin transporter (PGT) encoded by the Slco2a1 gene.

FIG. 7B: PGE2 synthesizing enzymes, Ptges and Ptges2.

FIG. 7C: EP1-4 receptors encoded by the genes Ptger1-4.

FIG. 7D: Pax7 mRNA levels in MuSCs after 24 hr treatment with vehicle (−) or PGE2 treatment; (n=3 mice with 2 technical replicates).

FIG. 7E: Single aged MuSC clones tracked by time-lapse microscopy after acute treatment with vehicle (−; top) or PGE2 (bottom). For each clone the resulting number of live (open bar) and dead (black bar) cells after 48 h timelapse tracking is shown.

FIG. 7F: Proliferation curve of tracked live aged MuSCs assessed by time-lapse microscopy for vehicle (−) or transient PGE2 treatment during 48 h.

FIG. 7G: Flow cytometry analysis of apoptotic Annexin V$^+$ on aged MuSCs after 24 hr treatment with vehicle (−) or PGE2 and analyzed 7 days later after growth on hydrogels; (n=9 mice in 3 independent experiments). Mann-Whitney test (FIGS. 7A-7D) and paired t-test (FIG. 7G) at α=0.05. Means+s.e.m. n.s., non-significant.

FIG. 8A: Representative cross-sectional images of tibialis anterior myofibers of young mice treated in vivo with vehicle (−) or PGE2 48 hr post-cardiotoxin (CTX) injury. Images show staining with LAMININ, green and DAPI, blue.

FIG. 8B: The corresponding segmentation images from FIG. 8A analyzed by the Baxter Algorithms for Myofiber Analysis to determine the cross sectional area (CSA) of transverse sections of myofibers (bottom) at day 14 post-injury. Bar represents 40 µm.

FIG. 9A: Experimental scheme.

FIG. 9B: Expression of Ptger4 (EP4 receptor) in sorted MuSCs ($\alpha^{7+}$ CD34$^{+}$ lin$^{-}$) from control or EP4 KO mice post-injury.

FIG. 9C: Representative TA cross-section. DAPI, blue; Embryonic Myosin Heavy Chain (eMyHC), red. Bar=40 µm.

FIG. 9D: Percentage of eMyHC$^{+}$ fibers.

FIG. 9E: Myofiber cross-sectional areas (CSA) in control and Pax7-specific EP4 knockout TAs.

FIG. 9F: Muscle twitch forces and (FIG. 9G) muscle tetanic force at day 14 post-notexin injury. Mann-Whitney test (FIGS. 9B, 9C, 9F, and 9G); ANOVA test for group comparison and significant difference for each bin by Fisher's test (FIG. 9E). * $P<0.05$, * $P<0.0005$, and ** $P<0.0001$. Means+s.e.m.

FIG. 10A: Experimental scheme.

FIG. 10B: BLI; (n=3 mice per condition).

FIG. 10C: Muscle twitch forces at day 14 post-notexin injury (n=8 for vehicle-treated and 10 for NSAID-treated). ANOVA test for group comparison and significant difference for the endpoint by Fisher's test (FIG. 10B). Mann-Whitney test (FIG. 10C). * $P<0.05$,  $P<0.001$, * $P<0.0005$, and **** $P<0.0001$. Means+s.e.m

DETAILED DESCRIPTION OF THE INVENTION

I. Introduction

Figure 1A:
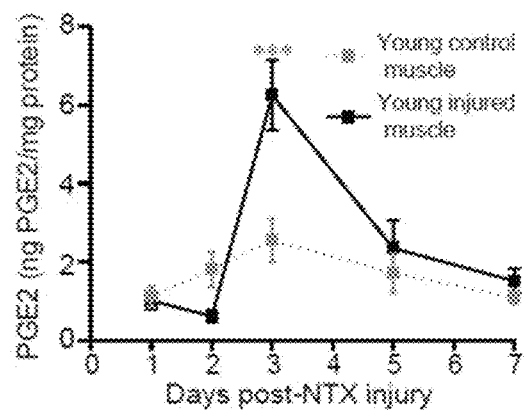
FIGS. 1A-1H show that transient PGE2 treatment promotes young MuSC proliferation in vitro.

The present invention is based, in part, on the discovery that prostaglandin E2 (PGE2) can improve muscle cell proliferation and function. PGE2 alone or in combination with isolated muscle cells can be used to repair muscle damage due to injury, atrophy, or disease. In fact, PGE2-treated muscle cells exhibit enhanced muscle regeneration and improved muscle function upon administration. As such, provided herein are novel therapeutic methods, compositions, and kits to promote muscle regeneration and rejuvenation of damaged, injured, or atrophied muscle.

II. General

Practicing this invention utilizes routine techniques in the field of molecular biology. Basic texts disclosing the general methods of use in this invention include Sambrook and Russell, *Molecular Cloning. A Laboratory Manual* (3rd ed. 2001); Kriegler, *Gene Transfer and Expression: A Laboratory Manual* (1990); *and Current Protocols in Molecular Biology* (Ausubel et al., eds., 1994)).

For nucleic acids, sizes are given in either kilobases (kb), base pairs (bp), or nucleotides (nt). Sizes of single-stranded DNA and/or RNA can be given in nucleotides. These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

III. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "prostaglandin E2" or "PGE2" refers to prostaglandin that can be synthesized via arachidonic acid via cyclooxygenase (COX) enzymes and terminal prostaglandin E synthases (PGES). PGE2 plays a role in a number of biological functions including vasodilation, inflammation, and modulation of sleep/wake cycles.

The term "prostaglandin E2 receptor agonist" or "PGE2 receptor agonist" refers to a chemical compound, small molecule, polypeptide, biological product, etc. that can bind to and activate any PGE2 receptor, thereby stimulating the PGE2 signaling pathway.

The term "compound that attenuates PGE2 catabolism" refers to a chemical compound, small molecule, polypeptide, biological product, etc. that can reduce or decrease the breakdown of PGE2.

The term "compound that neutralizes PGE2 inhibition" refers to a chemical compound, small molecule, polypeptide, biological product, etc. that can block or impede an inhibitor of PGE2 synthesis, activity, secretion, function, and the like.

The term "derivative," in the context of a compound, includes but is not limited to, amide, ether, ester, amino, carboxyl, acetyl, and/or alcohol derivatives of a given compound.

The term "embryonic stem cell-derived muscle cell" or "ESC-derived muscle cell" refers to a muscle cell that is derived from or differentiated from an embryonic stem cell.

The term "induced pluripotent stem cell-derived muscle cell" or "iPSC-derived muscle cell" refers to a muscle cell that is derived from or differentiated from an induced pluripotent stem cell.

The term "isolated," in the context of cells, refers to a single cell of interest or a population of cells of interest, at least partially isolated and/or purified from other cell types or other cellular material with which it naturally occurs in the tissue of origin (e.g., muscle tissue). A population of muscle cells is "isolated" when it is at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98% and, in certain cases, at least about 99% free of cells that are not muscle cells. Purity can be measured by any appropriate method, for example, by fluorescence-activated cell sorting.

The term "autologous" refers to any material (e.g., a cell) derived from the same individual to whom it is later to be re-introduced into the individual.

The term "allogeneic" refers to any material (e.g., a cell) derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "treating" or "treatment" refers to any one of the following: ameliorating one or more symptoms of disease; preventing the manifestation of such symptoms before they occur; slowing down or completely preventing the progression of the disease (as may be evident by longer periods between reoccurrence episodes, slowing down or prevention of the deterioration of symptoms, etc.); enhancing the onset of a remission period; slowing down the irreversible damage caused in the progressive-chronic stage of the disease (both in the primary and secondary stages); delaying the onset of said progressive stage; or any combination thereof.

The term "administer," "administering," or "administration" refers to the methods that may be used to enable delivery of agents or compositions such as the compounds and cells described herein to a desired site of biological action. These methods include, but are not limited to, parenteral administration (e.g., intravenous, subcutaneous, intraperitoneal, intramuscular, intra-arterial, intravascular, intracardiac, intrathecal, intranasal, intradermal, intravitreal, and the like), transmucosal injection, oral administration, administration as a suppository, and topical administration. One skilled in the art will know of additional methods for administering a therapeutically effective amount of the compounds and/or cells described herein for preventing or relieving one or more symptoms associated with a disease or condition.

The term "therapeutically effective amount" or "therapeutically effective dose" or "effective amount" refers to an amount of a compound, therapeutic agent (e.g., cells), and/or pharmaceutical drug that is sufficient to bring about a beneficial or desired clinical effect. A therapeutically effective amount or dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment). Therapeutically effective amounts of a pharmaceutical compound or compositions, as described herein, can be estimated initially from cell culture and animal models. For example, $IC_{50}$ values determined in cell culture methods can serve as a starting point in animal models, while $IC_{50}$ values determined in animal models can be used to find a therapeutically effective dose in humans.

The term "pharmaceutically acceptable carrier" refers to refers to a carrier or a diluent that does not cause significant irritation to an organism and does not abrogate the biological activity and properties of the administered compound.

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets.

The term "acute exposure," in the context of administration of a compound, refers to a temporary or brief application of a compound to a subject, e.g., human subject, or cells. In some embodiments, an acute exposure includes a single administration of a compound over the course of treatment or over an extended period of time.

The term "intermittent exposure," in the context of administration of a compound, refers to a repeated application of a compound to a subject, e.g., human subject, or cells, wherein a desired period of time lapses between applications.

The term "acute regimen," in the context of administration of a compound, refers to a temporary or brief application of a compound to a subject, e.g., human subject, or to a repeated application of a compound to a subject, e.g., human subject, wherein a desired period of time (e.g., 1 day) lapses between applications. In some embodiments, an acute regimen includes an acute exposure (e.g., a single dose) of a compound to a subject over the course of treatment or over an extended period of time. In other embodiments, an acute regimen includes intermittent exposure (e.g., repeated doses) of a compound to a subject in which a desired period of time lapses between each exposure.

The term "continuous exposure," in the context of administration of a compound, refers to a repeated, chronic application of a compound to a subject, e.g., human subject, or cells, over an extended period of time.

The term "chronic regimen," in the context of administration of a compound, refers to a repeated, chronic application of a compound to a subject, e.g., human subject, over an extended period of time such that the amount or level of the compound is substantially constant over a selected time period. In some embodiments, a chronic regimen includes a continuous exposure of a compound to a subject over an extended period of time.

IV. Detailed Description of the Embodiments

In one aspect, provided herein is a method for stimulating the proliferation, expansion, and/or engraftment of a population of isolated muscle cells by culturing the population of isolated muscle cells with a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof. In some embodiments, the population of isolated muscle cells is substantially purified or purified (e.g., separated from non-muscle cells or other cells that are not of interest). In some instances, the population of isolated muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof. In particular embodiments, the population of isolated muscle cells comprises muscle stem cells, satellite cells, myocytes, myoblasts, myotubes, myofibers, or a combination thereof.

The population of isolated muscle cells can be obtained from a subject. In other embodiments, the isolated muscles cells are from a cell line, e.g., a primary cell line. In some instances, the subject has a condition or disease associated with muscle damage, injury, or atrophy. The condition or disease associated with muscle damage, injury, or atrophy can be selected from the group consisting of acute muscle injury, tear, or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

In some embodiments, the PGE2 derivative comprises 16,16-dimethyl prostaglandin E2. In other embodiments, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1), which transports PGE2 inside the cells for catabolism by 15-PGDH.

In some embodiments, the step of culturing the population of isolated muscle cells with the compound comprises acute, intermittent, or continuous exposure of the population of isolated muscle cells to the compound. The compound may be exposed to the isolated cells once in an acute manner. In other cases, the compound may be exposed to the isolated cells at more than one time point such that time elapses between exposures. In yet other cases, the compound may be exposed to the isolated cells continuously such that the level of compound in direct contact with the cells does not fall below a pre-selected amount.

In particular embodiments, provided herein is a method for promoting muscle cell engraftment in a subject. The method includes culturing or contacting a population of isolated muscle cells with an effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, to promote engraftment of the muscle cells in the subject; and administering the cultured or contacted muscle cells to the subject.

In another aspect, provided herein is a composition comprising a population of isolated muscle cells and a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof. In some embodiments, the population of isolated muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof. In some instances, the population of isolated muscle cells comprises muscle stem cells, satellite cells, myocytes, myoblasts, myotubes, myofibers, or a combination thereof. The composition can also include a pharmaceutically acceptable carrier.

In yet another aspect, provided herein is a kit comprising any of the compositions disclosed herein, and an instruction manual.

In another aspect, provided herein is a method for regenerating a population of muscle cells in a subject having a condition or disease associated with muscle damage, injury, or atrophy. The method includes administering to the subject a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, to increase the population of muscle cells in the subject and/or to enhance muscle function in the subject.

In a related aspect, provided herein is a method for stimulating the proliferation and/or expansion of a population of muscle cells in a subject having a condition or disease associated with muscle damage, injury, or atrophy. The method includes administering to the subject a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, to increase the population of muscle cells in the subject and/or to enhance muscle function in the subject.

In some embodiments, the population of muscle cells comprises an endogenous population of muscle cells. In other embodiments, the population of muscle cells comprises a population of isolated muscle cells that has been administered (e.g., injected or transplanted) to the subject. In yet other embodiments, the population of muscle cells comprises both an endogenous population of muscle cells and a population of isolated muscle cells that has been administered to the subject.

In some embodiments, the condition or disease associated with muscle damage, injury, or atrophy is selected from the group consisting of acute muscle injury or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

In some embodiments, the population of muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof. In some cases, the population of muscle cells comprises muscle stem cells, satellite cells, myocytes, myoblasts, myotubes, myofibers, or a combination thereof.

In some embodiments, the PGE2 derivative comprises 16,16-dimethyl prostaglandin E2.

In some embodiments, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1).

In some embodiments, the step of administering the compound comprises oral, intraperitoneal, intramuscular, intra-arterial, intradermal, subcutaneous, intravenous, or intracardiac administration. In some cases, the compound is administered in accordance with an acute regimen. In certain instances, the acute regimen comprises acute exposure (e.g., a single dose) of the compound to the subject. In other instances, the acute regimen comprises intermittent exposure (e.g., repeated doses) of the compound to the subject. As a non-limiting example, an acute PGE2 regimen can comprise a series of intermittent (e.g., daily) doses of PGE2 over a desired period of time (e.g., over the course of 2, 3, 4, 5, 6, or 7 days).

In other embodiments, the step of administering further comprises administering a population of isolated muscle cells to the subject. The population of isolated muscle cells can be autologous to the subject. The population of isolated muscle cells can be allogeneic to the subject. In some instances, the population of isolated muscle cells is substantially purified or purified. In other instances, the population of isolated muscle cells is cultured with the compound prior to being administered to the subject. The step of culturing the population of isolated muscle cells with the compound can include acute, intermittent, or continuous exposure of the population of isolated muscle cells to the compound. Administering the population of isolated muscle cells can comprise injecting or transplanting the cells into the subject. The population of isolated muscle cells and the compound can be administered to the subject concomitantly. Alternatively, the population of isolated muscle cells and the compound can be administered to the subject sequentially.

In another aspect, provided herein is a method for preventing or treating a condition or disease associated with muscle damage, injury or atrophy in a subject in need thereof. The method includes administering to the subject (i) a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, and (ii) a population of isolated muscle cells, to prevent or treat the condition or disease associated with muscle damage, injury, or atrophy.

In a related aspect, provided herein is a method for stimulating the proliferation and/or expansion of a population of muscle cells in a subject having a condition or disease associated with muscle damage, injury, or atrophy by administering to the subject (i) a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, and (ii) a population of isolated muscle cells. In some embodiments, the population of muscle cells comprises an endogenous population of muscle cells. In other embodiments, the population of muscle cells comprises the population of isolated muscle cells that has been administered (e.g., injected or transplanted) to the subject. In yet other embodiments, the population of muscle cells comprises both an endogenous population of muscle cells and the population of isolated muscle cells that has been administered to the subject. In certain embodiments, the therapeutically effective amount of the compound comprises an amount that is sufficient to increase the population of endogenous muscle cells in the subject and/or to increase the population of isolated muscle cells that has been administered to the subject and/or to enhance muscle function in the subject.

In some embodiments, the PGE2 derivative comprises 16,16-dimethyl prostaglandin E2. In some instances, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1).

In some embodiments, the population of muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof. In some cases, the population of muscle cells comprises muscle stem cells, satellite cells, myocytes, myoblasts, myotubes, myofibers, or a combination thereof. The population of isolated muscle cells can be substantially purified or purified.

In some embodiments, the population of isolated muscle cells is cultured with the compound prior to being administered to the subject. In some cases, culturing the population of isolated muscle cells with the compound comprises acute, intermittent, or continuous exposure of the population of isolated muscle cells to the compound.

In some embodiments, the population of isolated muscle cells is autologous to the subject. In other embodiments, the population of isolated muscle cells is allogeneic to the subject.

Administration of the compound can be oral, intraperitoneal, intramuscular, intra-arterial, intradermal, subcutaneous, intravenous, or intracardiac administration. In some cases, the compound is administered in accordance with an acute regimen. In certain instances, the acute regimen comprises acute exposure (e.g., a single dose) of the compound to the subject. In other instances, the acute regimen comprises intermittent exposure (e.g., repeated doses) of the compound to the subject. As a non-limiting example, an acute PGE2 regimen can comprise a series of intermittent (e.g., daily) doses of PGE2 over a desired period of time (e.g., over the course of 2, 3, 4, 5, 6, or 7 days). Administration of the population of isolated muscle cells can include injecting or transplanting the cells into the subject. The compound and the population of isolated muscle cells can be administered to the subject concomitantly. Optionally, the compound and the population of isolated muscle cells can be administered to the subject sequentially.

In some embodiments, the subject is suspected of having or at risk for developing the condition or disease associated with muscle damage, injury, or atrophy. In some cases, the condition or disease associated with muscle damage, injury or atrophy is selected from the group consisting of acute muscle injury or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

A. Methods for Stimulating the Proliferation or Engraftment of Muscle Cells

Provided herein are in vitro or ex vivo methods for stimulating or promoting the proliferation and/or engraftment of isolated muscle cells. The methods include culturing or contacting a population of isolated muscle cells with prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, or a combination thereof. The compound can be added to any culture media used to maintain or propagate the cells.

The compound can be any small molecule, prodrug, biological product, and the like that can mimic, activate, or stimulate PGE2 signaling. In some cases, the compound is PGE2 (i.e., dinoprostone), a synthetic PGE2 derivative (e.g., 16,16-dimethyl prostaglandin E2; dmPGE2), a synthetic PGE2 analog, a synthetic PGE2 variant, or a muscle-specific PGE2 variant. In other cases, the compound is a PGE2 prodrug such as a prodrug of PGE2 that can be metabolized into a pharmacologically active PGE2 drug when exposed to muscle cells or in close proximity to muscle cells. In yet other cases, the compound can be an agonist of any one of the PGE2 receptors including PGE2 receptor 1, PGE2 receptor 2, PGE2 receptor 3, and PGE2 receptor 4. The agonist can specifically bind to or activate one or more PGE2 receptors. In some cases, the compound can be a compound that attenuates, impedes, inhibits or decreases PGE2 catabolism such as a compound or neutralizing (blocking) antibody that inactivates or blocks an enzyme that degrades or metabolizes PGE2, e.g., 15-hydroxyprostaglandin dehydrogenase (15-PGDH). In other cases, the compound blocks, hinders or opposes inhibition of PGE2 and/or PGE2 synthesis, activity, and/or secretion.

In some embodiments, the compounds described herein can trigger proliferation of muscle cells including quiescent muscle cells. The population of isolated muscle cells can be a pure or substantially pure population of muscle cells such that at least about 90% of the muscle cells are a single type of muscle cell. In other embodiments, the population is a mixture of muscle cells wherein less than about 90% of the cells are of one type of cell. In some instances, the muscle cells include skeletal muscle cells, smooth muscle cells, and/or cardiac muscle cells harvested from a subject. In other instances, the muscle cells are generated or differentiated from embryonic stem cells, e.g., human embryonic stem cells or induced pluripotent stem cells, e.g., human induced pluripotent stem cells. In yet other instances, the muscle cells are dedifferentiated muscle cells. In some embodiments, the population of isolated muscle cells comprises muscle stem cells, satellite cells, myocytes, myoblasts, myotubes, myofibers, or a combination thereof. For instance, the isolated muscle cells can be a pure or substantially pure population of muscle stem cells. Alternatively, the isolated muscle cells can be a pure or substantially pure population of satellite cells. In other instances, the isolated muscle cells can a heterogeneous mixture of muscle stem cells, satellite cells, myocytes, myoblasts, myotubes, myofibers, or any combination thereof. As such, the mixture can include muscle stem cells and satellite cells, and optionally, myocytes.

In some embodiments, the muscle cells or the induced pluripotent stem cells are derived from a subject with a condition or disease associated with muscle damage, injury, or atrophy. In some embodiments, the condition or disease associated with muscle damage, injury, or atrophy is acute muscle injury, tear or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia or any combination thereof.

In particular embodiments, ex vivo methods for promoting muscle cell engraftment in a subject are provided. The methods include culturing or contacting a population of isolated muscle cells with an effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, to promote engraftment of the muscle cells in the subject. The methods also include administering the cultured or contacted muscle cells to the subject. In some instances, the population of isolated muscle cells is autologous to the subject. In other instances, the population of isolated muscle cells is allogeneic to the subject. In some embodiments, the subject is a human. In some embodiments, the subject has a condition or disease associated with muscle damage, injury, or atrophy. In some embodiments, the methods further include administering to the subject a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier. The subject can be administered the compound before, simultaneously with, and/or after the cultured or contacted muscle cells are administered to the subject. In some instances, the population of isolated muscle cells is cultured or contacted with the same compound that is administered to the subject. In other instances, the population of isolated muscle cells is cultured or contacted with a compound that is different from the compound administered to the subject.

The muscle cells can be obtained from any muscle of the body including, but not limited to, musculi pectoralis complex, latissimus dorsi, teres major and subscapularis, brachioradialis, biceps, brachialis, pronator quadratus, pronator teres, flexor carpi radialis, flexor carpi ulnaris, flexor digitorum superficialis, flexor digitorum profundus, flexor pollicis brevis, opponens pollicis, adductor pollicis, flexor pollicis brevis, iliopsoas, psoas, rectus abdominis, rectus femoris, gluteus maximus, gluteus medius, medial hamstrings, gastrocnemius, lateral hamstring, quadriceps mechanism, adductor longus, adductor brevis, adductor magnus, gastrocnemius medial, gastrocnemius lateral, soleus, tibialis posterior, tibialis anterior, flexor digitorum longus, flexor digitorum brevis, flexor hallucis longus, extensor hallucis longus, hand muscles, arm muscles, foot muscles, leg muscles, chest muscles, stomach muscles, back muscles, buttock muscles, shoulder muscles, head and neck muscles, and the like.

In some embodiments, the muscle cells are obtained from a particular muscle, expanded according to the method disclosed herein, and then transplanted back to the same muscle, or alternatively, transplanted to a different muscle. In some cases, the source of the muscle cells and the transplantation site is the same muscle of a subject. In other cases, the source of the muscle cells and the transplantation site are different muscles of a subject. In other cases, the source of the muscle cells and the transplantation site is the same type of muscle from different subjects. In yet other cases, the source of the muscle cells and the transplantation site are different types of muscle from different subjects.

The compounds disclosed herein can be cultured with isolated muscle cells acutely, intermittently or continuously. In some embodiments, the compound is exposed to the cells in a single dose for a duration of time. In other embodiments, the compound is exposed to the cells in at least two or more doses such that a period of time, e.g., a day, two days, a week or more, passes between dosings. In some embodiments, the compound is chronically or continuously exposed to the cells, e.g., without a change in the compound concentration or in the effect on the cells, over a duration of time.

B. Methods for Regenerating Damaged Muscle Cells in a Subject

The methods provided herein can be used to regenerate or rejuvenate muscle in a subject, such as a human subject. Regeneration of muscle includes forming new muscle fibers from muscle stem cells, satellite cells, muscle progenitor cells, and any combination thereof. The methods are also useful for enhancing or augment muscle repair and/or maintenance.

The PGE2 compounds of the present invention can be administered to a subject experiencing muscle degeneration or atrophy. Muscle atrophy can include loss of muscle mass and/or strength. It can affect any muscle of a subject. In some cases, the subject in need of the compositions, methods, and kits provided herein is exhibiting or experiencing muscle loss due to, e.g., age, inactivity, injury, disease, and any combination thereof.

In some embodiments, compounds can activate muscle cell proliferation, differentiation, and/or fusion of muscle cells. In some cases, the muscle tissue is regenerated. In other cases, muscle function (e.g., muscle mass, muscle strength, and/or muscle contraction) is restored or enhanced. In some cases, muscle weakness and atrophy are ameliorated.

The damaged muscle can be any muscle of the body, including but not limited to, musculi pectoralis complex, latissimus dorsi, teres major and subscapularis, brachioradialis, biceps, brachialis, pronator quadratus, pronator teres, flexor carpi radialis, flexor carpi ulnaris, flexor digitorum superficialis, flexor digitorum profundus, flexor pollicis brevis, opponens pollicis, adductor pollicis, flexor pollicis brevis, iliopsoas, psoas, rectus abdominis, rectus femoris, gluteus maximus, gluteus medius, medial hamstrings, gastrocnemius, lateral hamstring, quadriceps mechanism, adductor longus, adductor brevis, adductor magnus, gastrocnemius medial, gastrocnemius lateral, soleus, tibialis posterior, tibialis anterior, flexor digitorum longus, flexor digitorum brevis, flexor hallucis longus, extensor hallucis longus, hand muscles, arm muscles, foot muscles, leg muscles, chest muscles, stomach muscles, back muscles, buttock muscles, shoulder muscles, head and neck muscles, facial muscles, oculopharyngeal muscles, and the like.

Subjects in need of muscle regeneration may have musculoskeletal injuries (e.g., fractures, strains, sprains, acute injuries, overuse injuries, and the like), post-trauma damages to limbs or face, athletic injuries, post-fractures in the aged, soft tissue hand injuries, muscle atrophy (e.g., loss of muscle mass), Duchenne muscular dystrophy (DMD), Becker muscular dystrophy, Fukuyama congenital muscular dystrophy (FCMD), limb-girdle muscular dystrophy (LGMD), congenital muscular dystrophy, facioscapulohumeral muscular dystrophy (FHMD), myotonic muscular dystrophy, oculopharyngeal muscular dystrophy, distal muscular dystrophy, Emery-Dreifuss muscular dystrophy, myotonia congenita, myotonic dystrophy, other muscular dystrophies, muscle wasting disease, such as cachexia due to cancer, end stage renal disease (ESRD), acquired immune deficiency syndrome (AIDS), or chronic obstructive pulmonary disease (COPD), post-surgical muscle weakness, post-traumatic muscle weakness, sarcopenia, inactivity (e.g., muscle disuse or immobility), urethral sphincter deficiency, urethral sphincter deficiency, neuromuscular disease, and the like.

Non-limiting examples of neuromuscular diseases include, but are not limited to, acid maltase deficiency, amyotrophic lateral sclerosis, Andersen-Tawil syndrome, Becker muscular dystrophy, Becker myotonia congenita, Bethlem myopathy, bulbospinal muscular atrophy, carnitine deficiency, carnitine palmityl transferase deficiency, central core disease, centronuclear myopathy, Charcot-Marie-Tooth disease, congenital muscular dystrophy, congenital myasthenic syndromes, congenital myotonic dystrophy, Cori disease, Debrancher enzyme deficiency, Dejerine-Sottas disease, dermatomyositis, distal muscular dystrophy, Duchenne muscular dystrophy, dystrophia myotonica, Emery-Dreifuss muscular dystrophy, endocrine myopathies, Eulenberg disease, facioscapulohumeral muscular dystrophy, tibial distal myopathy, Friedreich's ataxia, Fukuyama congenital muscular dystrophy, glycogenosis type 10, glycogenosis type 11, glycogenosis type 2, glycogenosis type 3, glycogenosis type 5, glycogenosis type 7, glycogenosis type 9, Gowers-Laing distal myopathy, hereditary inclusion-body myositis, hyperthyroid myopathy, hypothyroid myopathy, inclusion-body myositis, inherited myopathies, integrin-deficient congenital muscular dystrophy, spinal-bulbar muscular atrophy, spinal muscular atrophy, lactate dehydrogenase deficiency, Lambert-Eaton myasthenic syndrome, McArdel disease, merosin-deficient congenital muscular dystrophy, metabolic diseases of muscle, mitochondrial myopathy, Miyoshi distal myopathy, motor neuron disease, muscle-eye-brain disease, myasthenia gravis, myoadenylate deaminase deficiency, myofibrillar myopathy, myophosphorylase deficiency, myotonia congenital, myotonic muscular dystrophy, myotubular myopathy, nemaline myopathy, Nonaka distal myopathy, oculopharyngeal muscular dystrophy, paramyotonia congenital, Pearson syndrome, periodic paralysis, phosphofructokinase deficiency, phosphoglycerate kinase deficiency, phosphoglycerate mutase deficiency, phosphorylase deficiency, polymyositis, Pompe disease, progressive external ophthalmoplegia, spinal muscular atrophy, Ullrich congenital muscular dystrophy, Welander distal myopathy, ZASP-related myopathy, and the like.

Muscle atrophy (e.g., muscle wasting) can be caused by or associated with, for example, normal aging (e.g., sarcopenia), genetic abnormalities (e.g., mutations or single nucleotide polymorphisms), poor nourishment, poor circulation, loss of hormonal support, disuse of the muscle due to lack of exercise (e.g., bedrest, immobilization of a limb in a cast, etc.), aging, damage to the nerve innervating the muscle, poliomyelitis, amyotrophic lateral sclerosis (ALS or Lou Gehrig's disease), heart failure, liver disease, diabetes, obesity, metabolic syndrome, demyelinating diseases (e.g., multiple sclerosis, Charcot-Marie-Tooth disease, Pelizaeus-Merzbacher disease, encephalomyelitis, neuromyelitis optica, adrenoleukodystrophy, and Guillian-Barre syndrome), denervation, fatigue, exercise-induced muscle fatigue, frailty, neuromuscular disease, weakness, chronic pain, and the like.

In some aspects, provided herein are methods for regenerating muscle in a subject in need thereof by administering to the subject a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, to increase the population of muscle cells and/or to enhance muscle function in the subject. The population of muscle cells in the subject can include skeletal muscle cells, smooth muscle cells, cardiac muscle cells, embryonic stem cell-derived muscle cells, induced pluripotent stem cell-derived muscle cells, dedifferentiated muscle cells, or any combinations thereof. Additionally, the muscle cells in the subject can be muscle stem cells, satellite cells, myocytes, myoblasts, myotubes, myofibers, or any combination thereof. The compound can be administered to the subject by oral, intraperitoneal, intramuscular, intra-arterial, intradermal, subcutaneous, intravenous, or intracardiac administration. In some cases, the compound is administered directly to the dysfunctional, injured, damaged and/or atrophied muscle. The compound can be administered in accordance with an acute regimen (e.g., single or intermittent dosing) or a chronic regimen (e.g., continuous dosing).

In some embodiments, the subject is also administered a population of isolated (or isolated and purified) muscle cells that are either autologous or allogeneic to the subject. The cells can be isolated and/or purified by any method known to those of skill in the art. The cells can be a homogenous or heterogeneous population of muscle cells.

In some embodiments, the cells are stimulated to proliferate by culturing the cells with the PGE2 compound prior to administering them to the subject. The cells can be acutely, intermittently or continuously exposed to the compound during in vitro culturing. In some cases, the population of muscle cells increases by at least about 1%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 500%, at least about 1000%, or more after culturing with the PGE2 compound.

To regenerate or repair muscle in the subject, the compound of the present invention and the isolated muscle cells are administered to the subject concomitantly. In some embodiments, the compound and the cultured muscle cells are administered to the subject concomitantly. In other embodiments, the compound and the isolated muscle cells are administered to the subject sequentially. In yet other embodiments, the compound and the cultured muscle cells are administered to the subject sequentially.

The methods described herein can be used to increase the number of muscle fibers by at least about 1%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 500%, at least about 1000%, or more. In some embodiments, the methods can increase the growth of a damaged, injured, atrophied, or degenerated muscle.

C. Methods for Preventing or Treating a Condition or Disease Affecting Muscle

The methods provided herein can be used to prevent or treat a condition or disease associated with muscle damage, injury, or atrophy in a subject in need thereof. The method can provide prophylactic treatment to a subject who is likely to experience muscle damage, injury or atrophy. In some embodiments, the subject can have a condition or disease with possible secondary symptoms that affect muscle. In other embodiments, the subject has undergone a surgical or therapeutic intervention to treat the muscle condition or disease, and the method disclosed here is used to prevent or inhibit recurrence or relapse. In some embodiments, the subject has any one of the conditions or diseases described herein that affects muscle.

As used herein, the term "treatment" or "treating" encompasses administration of compounds and/or cells in an appropriate form prior to the onset of disease symptoms and/or after clinical manifestations, or other manifestations of the condition or disease to reduce disease severity, halt disease progression, or eliminate the disease. The term "prevention of" or "preventing" a disease includes prolonging or delaying the onset of symptoms of the condition or disease, preferably in a subject with increased susceptibility to the condition or disease.

The method includes administering to the subject (i) a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, and (ii) a population of isolated muscle cells, to prevent or treat the condition or disease associated with muscle damage, injury, or atrophy. The muscle cells can be autologous or allogeneic to the subject.

The compound can be administered orally, intraperitoneally, intramuscularly, intra-arterially, intradermally, subcutaneously, intravenously, or by intracardiac injection. The compound can be administered in accordance with an acute regimen (e.g., single or intermittent dosing) or a chronic regimen (e.g., continuous dosing). The isolated muscle cells can be administered by injection or transplantation. In some embodiments, the compound and the cells are administered together or concomitantly. In other embodiments, the compound and the cells are administered sequentially. In some cases, the compound is administered before the cells. In other cases, the cells are administered before the compound.

The isolated muscle cells can be substantially purified or purified prior to injection or transplantation into the subject. The cells can also be expanded or stimulated to proliferate in culture prior to administration. As described herein, isolated muscle cells including skeletal muscle cells, smooth muscle cells, cardiac muscle cells, embryonic stem cell-derived muscle cells, induced pluripotent stem cell-derived muscle cells, dedifferentiated muscle cells, muscle stem cells, satellite cells, myoblasts, myocytes, myotubes, myofibers, and any combination thereof can be cultured with the compounds of the present invention. By exposing the compound to the cells acutely, intermittently or continuously, the muscle cells proliferate and increase in number. The expanded cells can be transplanted into a subject experiencing muscle damage, injury or atrophy.

D. Prostaglandin E2 (PGE2) Compounds

In some embodiments, the compound of the present invention is selected from the group consisting of PGE2, a PGE2 prodrug, a PGE2 receptor agonist, a compound that attenuates PGE2 catabolism, a compound that neutralizes PGE2 inhibition, a derivative thereof, an analog thereof, and a combination thereof. In some cases, a compound that attenuates PGE2 catabolism can be a compound, a neutralizing peptide, or a neutralizing antibody that inactivates or blocks 15-hydroxyprostaglandin dehydrogenase (15-PGDH) or inactivates or blocks a prostaglandin transporter, which transports PGE2 inside cells for catabolism by 15-PGDH. The prostaglandin transporter is also known as 2310021C19Rik, MATR1, Matrin F/Q, OATP2A1, PGT, PHOAR2, SLC21A2, solute carrier organic anion transporter family member 2A1, and SLCO2A1.

The PGE2 receptor agonist can be a small molecule compound, an activating antibody that specifically binds to a PGE2 receptor, and the like. In some embodiments, the compound is a PGE2 derivative or analog. In some embodiments, the compound is a PGE2 prodrug. A prodrug of PGE2 can be metabolized into a pharmacologically active PGE2 drug, for example, at the site of administration or muscle regeneration, or when the prodrug is exposed to muscle cells.

In particular embodiments, the compound is a PGE2 derivative or analog that contains one or more modifications to PGE2 that increase its stability, activity, resistance to degradation, transport into muscle cells (e.g., promote cellular uptake), and/or retention in muscle cells (e.g., reduce secretion from muscle cells after uptake).

Without limitation, examples of PGE2 derivatives and analogs include 2,2-difluoro-16-phenoxy-PGE2 compounds, 2-decarboxy-2-hydroxymethyl-16-fluoro-PGE2 compounds, 2-decarboxy-2-hydroxymethyl-1-deoxy-PGE2 compounds, 19(R)-hydroxy PGE2, 16,16-dimethyl PGE2, 16,16-dimethyl PGE2 p-(p-acetamidobenzamido) phenyl ester, 11-deoxy-16,16-dimethyl PGE2, 9-deoxy-9-methylene-16,16-dimethyl PGE2, 9-deoxy-9-methylene PGE2, butaprost, sulprostone, enprostil, PGE2 serinol amide, PGE2 methyl ester, 16-phenyl tetranor PGE2, 5-trans-PGE2, 15(S)-15-methyl PGE2, and 15(R)-15-methyl PGE2. Additional PGE2 derivatives and analogs are set forth, e.g., in U.S. Pat. No. 5,409,911.

Additional non-limiting examples of PGE2 derivatives and analogs include hydantoin derivatives of PGE2, the more stable PGE2 analogs described in Zhao et al. (*Bioorganic & Medicinal Chemistry Letters*, 17:6572-5 (2007)) in which the hydroxy cyclopentanone ring is replaced by heterocyclic rings and the unsaturated alpha-alkenyl chain is substituted with a phenethyl chain, the PGE2 analogs described in Ungrin et al. (*Mol. Pharmacol.*, 59:1446-56 (2001)), the 13-dehydro derivatives of PGE2 described in Tanami et al. (*Bioorg. Med. Chem. Lett.*, 8:1507-10 (1998)), and the substituted cyclopentanes described in U.S. Pat. Nos. 8,546,603 and 8,158,676.

In some embodiments, the compound is an agonist of a PGE2 receptor, e.g., EP1 receptor, EP2 receptor, EP3 receptor, and EP4 receptor. Non-limiting examples of PGE2 receptor agonists include ONO-DI-004, ONO-AEI-259, ONO-AE-248, ONO-AE1-329, ONO-4819CD (Ono Pharmaceutical Co., Japan), L-902688 (Cayman Chemical), CAY10598 (Cayman Chemical), and CP-533536 (Pfizer). Additional PGE2 receptor agonists are described, e.g., in U.S. Pat. Nos. 6,410,591; 6,610,719; 6,747,037; 7,696,235; 7,662,839; 7,652,063; 7,622,475; and 7,608,637.

E. Isolated Muscle Cells

Muscle (myogenic) cells of the present invention include, but are not limited to, muscle stem cells, skeletal muscle stem cells, smooth muscle stem cells, cardiac muscle stem cells, muscle satellite cells, myogenic precursor cells, myogenic cells, myocytes, myoblasts, myotubes, postmitotic myotubes, multinucleated myofibers, and postmitotic muscle fibers. In some embodiments, the isolated muscle cells encompass muscle stem cells. In other embodiments, the isolated muscle cells include muscle satellite cells. The muscle cells can be derived from a stem cell such as a bone marrow-derived stem cell, or a pluripotent stem cell such as an embryonic stem cell or an induced pluripotent stem cell. In some embodiments, the isolated muscle cells include dedifferentiated muscle cells. In other embodiments, the muscle cells have been genetically modified to, in some cases, correct disease-associated gene mutations.

Satellite cells are small mononuclear progenitor cells that can reside within muscle tissue. These cells can be induced to proliferate and differentiate into muscle cells, and in some instances, fuse to muscle fibers. During muscle damage or injury, quiescent satellite cells (e.g., satellite cells that are not differentiating or undergoing cell division at present) and muscle stem cells can be activated to proliferate, and/or migrate out of the muscle stem cell niche. The satellite cells and muscle stem cells can also differentiate into myocytes, myoblasts, or other muscle cell types.

Methods and protocols for generating muscle cells from embryonic stem cells are described, e.g., in Hwang et al., *PLoS One*, 2013, 8(8):e72023; and Darabi et al., *Cell Stem Cell*, 2012, 10(5):610-9. Methods and protocols for generating muscle cells from induced pluripotent stem cells are described, e.g., in Darabi et al., *Cell Stem Cell*, 2012, 10(5):610-9; Tan et al., *PLoS One*, 2011; and Mizuno et al., *FASEB J.*, 2010, 24(7):2245-2253.

In some embodiments, muscle cells are obtained by biopsy from a muscle such as a mature or adult muscle, e.g., quadriceps, gluteus maximus, bicep, triceps, or any muscle from an individual. The muscle can be a skeletal muscle, smooth muscle, or cardiac muscle. Detailed descriptions of methods of isolating smooth muscle stem cells can be found, e.g., in U.S. Pat. No. 8,747,838, and U.S. Patent App. Publ. No. 20070224167. Methods of isolating muscle cells of interest such as muscle stem cells or satellite cells from muscle tissue are described in detail, for example, in Blanco-Bose et al., *Exp. Cell Res.*, 2001, 26592:212-220.

Methods for purifying a population of muscle cells of interest, e.g., muscle stem cells, muscle satellite cells, myocytes, myoblasts, myotubes, and/or myofibers include selecting, isolating or enriching for a cell having a specific cell surface marker or a specific polypeptide that is expressed on the cell surface of the muscle cell of interest. Useful cell surface markers are described in, e.g., Fukada et al., *Front. Physiol.*, 2013, 4:317. Cell sorting methods such as flow cytometry, e.g., fluorescence-activated cell sorting (FACS); magnetic bead cell separation, e.g., magnetic-activated cell sorting (MACS), and other antibody-based cell sorting methods can be performed to isolate or separate the muscle cells of interest from other cell types.

The isolated population of muscle cells of interest can be expanded or multiplied using conventional culture-based methods. Methods for culture muscle cells are found in, e.g., U.S. Pat. No. 5,324,656. In some cases, the cells are cultured on a scaffold or gel such as a hydrogel.

F. Methods of Administration

The compounds of the present invention can be administered locally at or near a site of injury in the subject or systemically. In some embodiments, the compounds can be administered, for example, intraperitoneally, intramuscularly, intra-arterially, orally, intravenously, intracranially, intrathecally, intraspinally, intralesionally, intranasally, subcutaneously, intracerebroventricularly, topically, and/or by inhalation. The compound may be administered simultaneously or sequentially with the muscle cells of interest. When the compound is administered simultaneously with the cells, both the compound and cells can be administered in the same composition. When administered separately, the compound can be provided in a pharmaceutically acceptable carrier. In some embodiments, the compound is administered before or after the administration of the cells.

In some embodiments, the compound is administered in accordance with an acute regimen. In certain instances, the compound is administered to the subject once. In other instances, the compound is administered at one time point, and administered again at a second time point. In yet other instances, the compound is administered to the subject repeatedly (e.g., once or twice daily) as intermittent doses over a short period of time (e.g., 2 days, 3 days, 4 days, 5 days, 6 days, a week, 2 weeks, 3 weeks, 4 weeks, a month, or more). In some cases, the time between compound administrations is about 1 day, 2 days, 3 days, 4 days, 5 days, 6 days, a week, 2 weeks, 3 weeks, 4 weeks, a month, or more. In other embodiments, the compound is administered continuously or chronically in accordance with a chronic regimen over a desired period of time. For instance, the compound can be administered such that the amount or level of the compound is substantially constant over a selected time period.

Administration of the isolated muscle cells into a subject can be accomplished by methods generally used in the art. In some embodiments, administration is by transplantation or injection such as intramuscular injection. The number of cells introduced will take into consideration factors such as sex, age, weight, the types of disease or disorder, stage of the disorder, the percentage of the desired cells in the cell population (e.g., purity of cell population), and the cell number needed to produce the desired result. Generally, for administering the cells for therapeutic purposes, the cells are given at a pharmacologically effective dose. By "pharmacologically effective amount" or "pharmacologically effective dose" is an amount sufficient to produce the desired physiological effect or amount capable of achieving the desired result, particularly for treating the condition or disease, including reducing or eliminating one or more symptoms or manifestations of the condition or disease. Pharmacologically effective doses will also apply to therapeutic compounds used in combination with the cells, as described herein.

Cells can be administered in one injection, or through successive injections over a defined time period sufficient to generate a therapeutic effect. Different populations of muscle cells may be injected when treatment involves successive injections. A pharmaceutically acceptable carrier, as further described below, may be used for injection of the cells into the subject. These will typically comprise, for example, buffered saline (e.g., phosphate buffered saline) or unsupplemented basal cell culture medium, or medium as known in the art.

Any number of muscles of the body may be directly injected with the compound and/or cells of the present invention, such as, for example, the biceps muscle; the triceps muscle; the brachioradialus muscle; the brachialis muscle (brachialis anticus); the superficial compartment wrist flexors; the deltoid muscle; the biceps femoris, the gracilis, the semitendinosus and the semimembranosus muscles of the hamstrings; the rectus femoris, vastus lateralis, vastus medialis and vastus intermedius muscles of the quadriceps; the gastrocnemius (lateral and medial), tibialis anterior, and the soleus muscles of the calves; the pectoralis major and the pectoralis minor muscles of the chest; the latissimus dorsi muscle of the upper back; the rhomboids (major and minor); the trapezius muscles that span the neck, shoulders and back; the rectus abdominis muscles of the abdomen; and the gluteus maximus, gluteus medius and gluteus minimus muscles of the buttocks.

G. Pharmaceutical Compositions

The pharmaceutical compositions of the compounds and cells of the present invention may comprise a pharmaceutically acceptable carrier. In certain aspects, pharmaceutically acceptable carriers are determined in part by the particular composition being administered, as well as by the particular method used to administer the composition. Accordingly, there is a wide variety of suitable formulations of pharmaceutical compositions of the present invention (see e.g., REMINGTON'S PHARMACEUTICAL SCIENCES, 18TH ED., Mack Publishing Co., Easton, PA (1990)).

As used herein, "pharmaceutically acceptable carrier" comprises any of standard pharmaceutically accepted carriers known to those of ordinary skill in the art in formulating pharmaceutical compositions. Thus, the cells or compounds, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

The pharmaceutical compositions of the invention are administered in a manner compatible with the dosage formulation, and in such amount as will be therapeutically effective. The quantity to be administered depends on a variety of factors including, e.g., the age, body weight, physical activity, and diet of the individual, the condition or disease to be treated, and the stage or severity of the condition or disease. In certain embodiments, the size of the dose may also be determined by the existence, nature, and extent of any adverse side effects that accompany the administration of a therapeutic agent(s) in a particular individual.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose of the compound may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for humans and other mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the therapeutic compound.

Methods for preparing such dosage forms are known to those skilled in the art (see. e.g., REMINGTON'S PHARMACEUTICAL SCIENCES, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

H. Kits

Other embodiments of the compositions described herein are kits comprising a population of isolated muscle cells and a compound selected from the group consisting of prostaglandin E2 (PGE2), a PGE2 prodrug, a PGE2 receptor agonist, a compound that attenuates PGE2 catabolism (e.g., 15-hydroxyprostaglandin dehydrogenase (15-PGDH) inhibitor or prostaglandin transporter (PTG or SLCO2A1) inhibitor), a compound that neutralizes PGE2 inhibition, a derivative thereof, an analog thereof, and a combination thereof. The kit typically contains containers which may be formed from a variety of materials such as glass or plastic, and can include for example, bottles, vials, syringes, and test tubes. A label typically accompanies the kit, and includes any writing or recorded material, which may be electronic or computer readable form providing instructions or other information for use of the kit contents.

V. Examples

The following examples are offered to illustrate, but not to limit, the claimed invention.

Example 1: Acute Prostaglandin E2 Delivery Augments Skeletal Muscle Regeneration and Strength in Aged Mice This example illustrates that PGE2 signaling is required for muscle stem cell function during regeneration.

The elderly suffer from progressive skeletal muscle wasting and regenerative failure that decreases mobility and quality of life[1,2]. Crucial to muscle regeneration are adult muscle stem cells (MuSCs) that reside in niches in muscle tissues, poised to respond to damage and repair skeletal muscles throughout life[3-8]. During aging, the proportion of functional MuSCs markedly decreases, hindering muscle regeneration[9-3]. To date, no therapeutic agents are in clinical use that target MuSCs to combat this regenerative decline. Here, we identify a natural immunomodulator, prostaglandin E2 (PGE2), as a potent regulator of MuSC function essential to muscle regeneration. We found that the PGE2 receptor, EP4, is essential for MuSC proliferation in vitro and engraftment in vivo in mice. In MuSCs of aged mice, the PGE2 pathway is dysregulated due to a cell intrinsic molecular defect, elevated prostaglandin degrading enzyme (15-PGDH) that renders PGE2 inactive. This defect is overcome by transient acute exposure of MuSCs to a stable degradation-resistant PGE2, 16,16-dimethyl PGE2 (dmPGE2), concomitant with MuSC transplantation into injured muscles. Notably, a single intramuscular injection of dmPGE2 alone suffices to accelerate regeneration, evident by an early increase in endogenous MuSC numbers and myofiber sizes following injury. Furthermore, aged mouse muscle force generating capacity was increased in response to exercise-induced regeneration and an acute dmPGE2 treatment regimen. Our findings reveal a novel therapeutic indication for PGE2 as a potent inducer of muscle regeneration and strength.

Figure 1B:
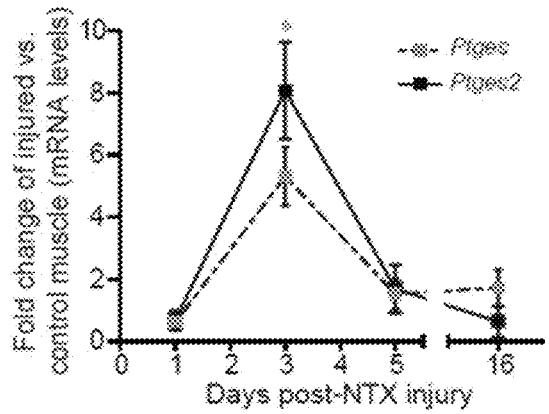
Figure 1C:
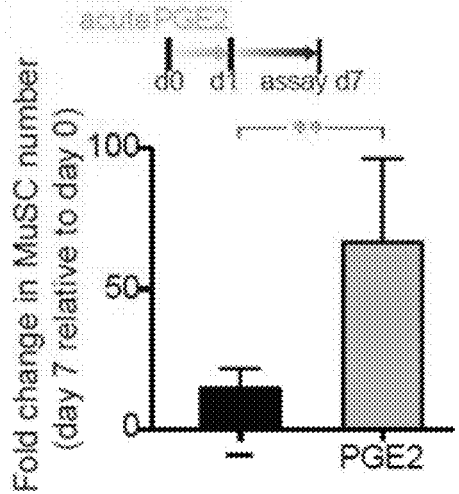
Figure 5A:
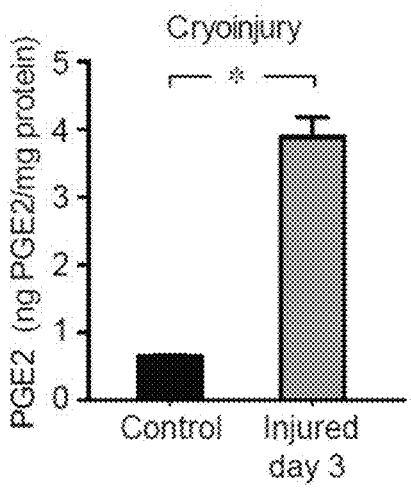
FIGS. 5A-5K show that PGE2 promotes MuSC expansion.
Figure 5B:
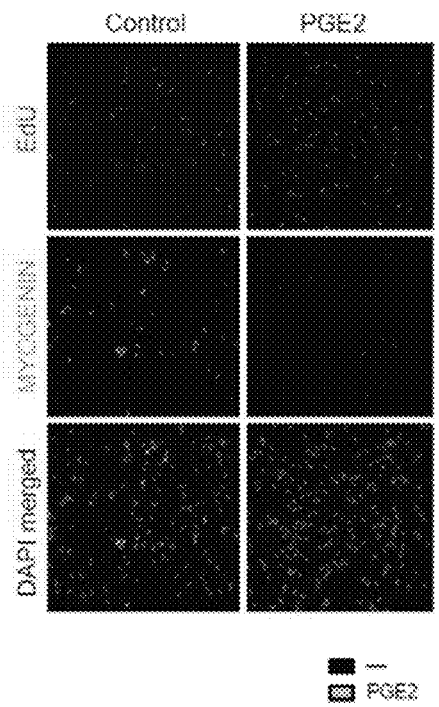
Figure 5C:
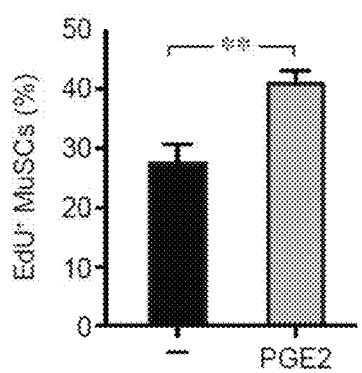
Figure 5D:
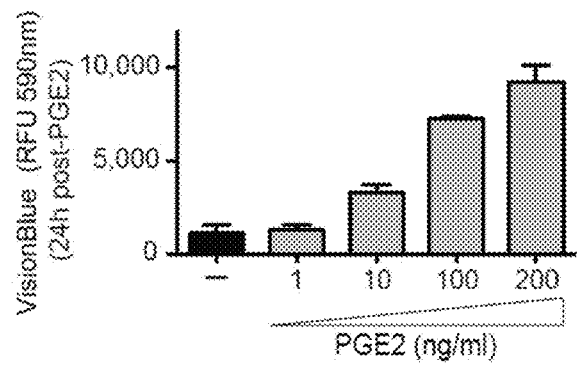

To counter the decline in muscle regenerative potential we sought therapeutic agents that target MuSCs, also known as satellite cells, a stem cell population dedicated to muscle regeneration[3-8]. Since a transient inflammatory and fibroadipogenic response plays a crucial role in muscle regeneration[14-17], we sought to identify inflammatory modulators induced by injury that could overcome the age-related decline in MuSC function. An analysis of our transcriptome database revealed that the Ptger4 receptor for PGE2, a natural and potent lipid mediator during acute inflammation[18], was expressed at high levels on freshly isolated MuSCs. In muscle tissue lysates, we detected a surge in levels of PGE2 three days after injury to young (2-4 mo) mouse muscles by standard injury paradigms entailing notexin injection or cryoinjury (FIG. 1A and FIG. 5A), and a concomitant upregulation of its synthesizing enzymes, Ptges and Ptges2 (FIG. 1B). This early and transient time window coincides with the well-documented kinetics of MuSC expansion and inflammatory cytokine accumulation post injury[8,15,16]. To determine if PGE2 treatment enhanced MuSC behavior, we FACS-purified MuSCs from hindlimb muscles from young mice (2-4 mo)[6] and plated them on hydrogels of 12 kpa stiffness to maintain stem cell function[19]. We found that PGE2 (10 ng/ml) increased cell division assayed by EDU incorporation (FIGS. 1B-ID) and that an acute 1-day exposure to PGE2 induced a 6-fold increase in the number of MuSCs relative to controls one week later (FIG. 1C).

Figure 1D:
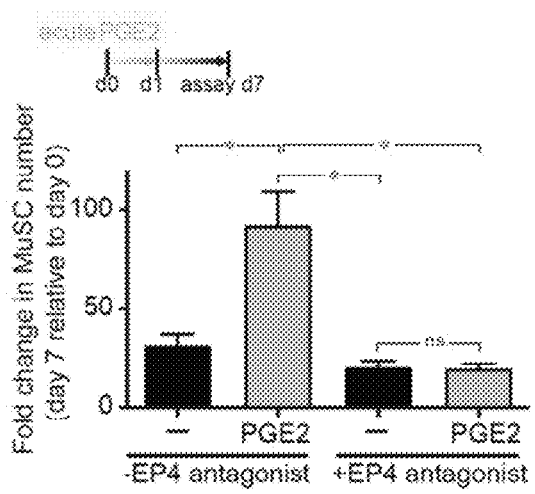
Figure 1E:
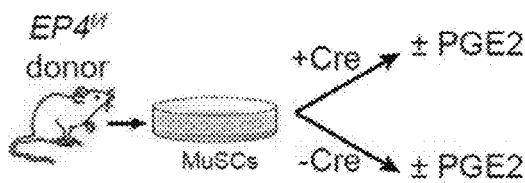
Figure 1F:
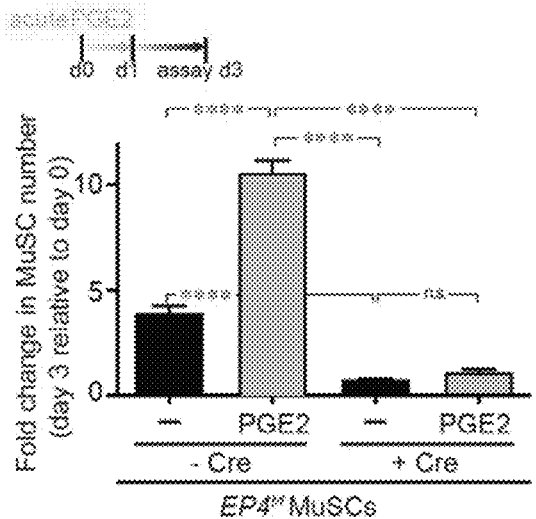
Figure 1G:
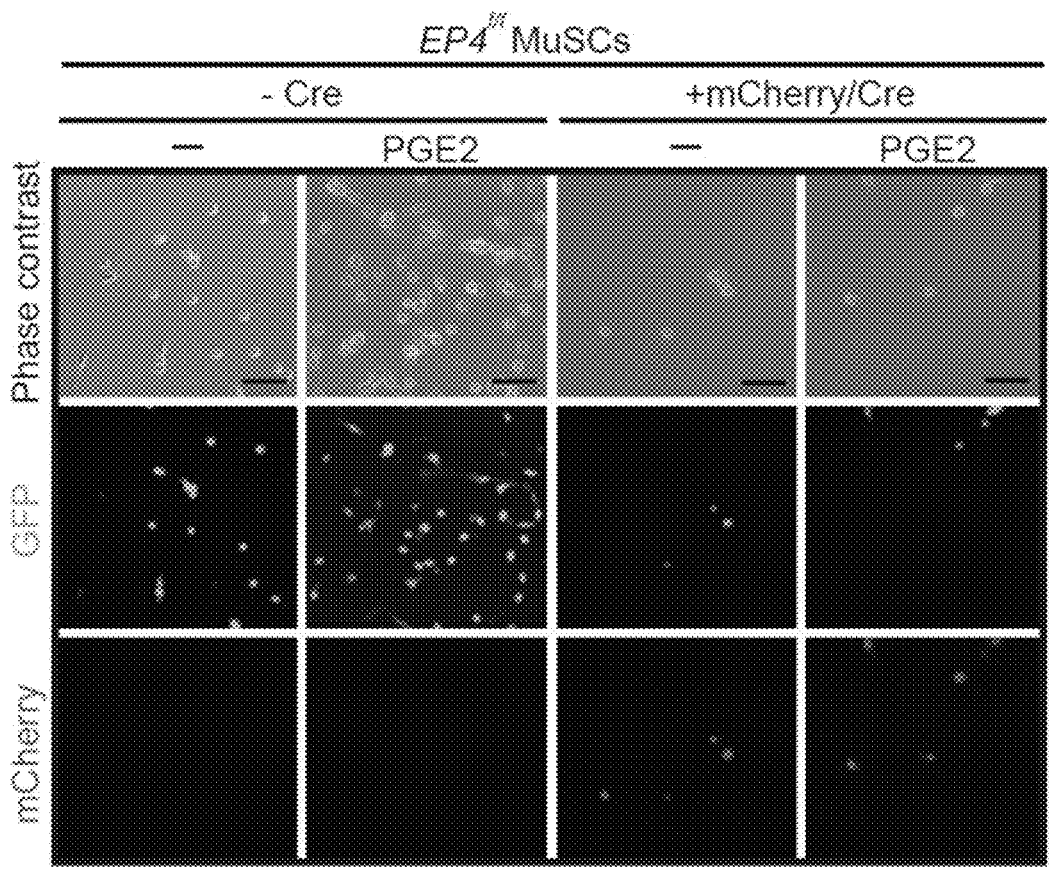
Figure 1H:
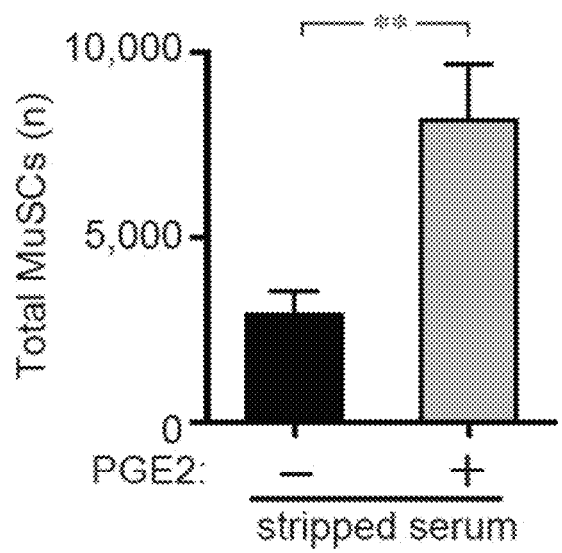
Figure 5E:
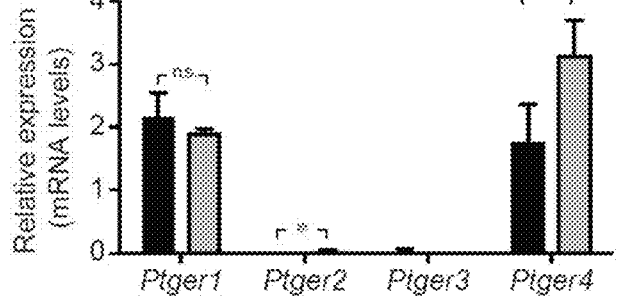
Figure 5F:
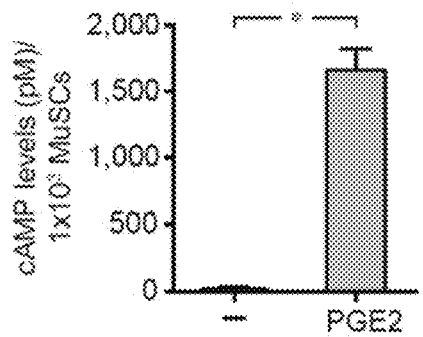
Figure 5G:
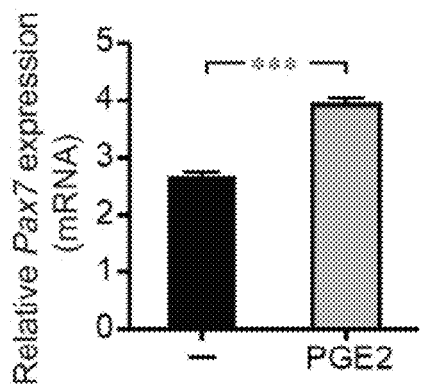
Figure 5H:
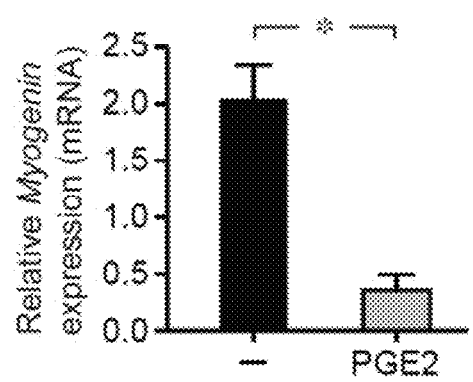
Figure 5I:
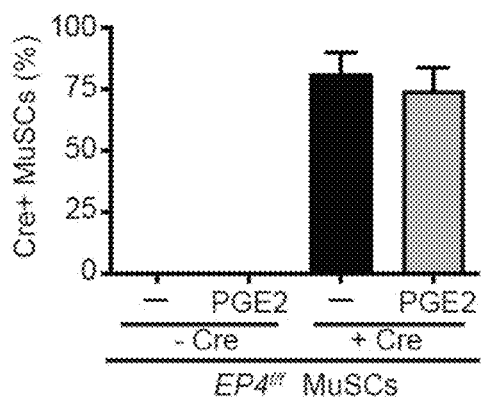
Figure 5J:
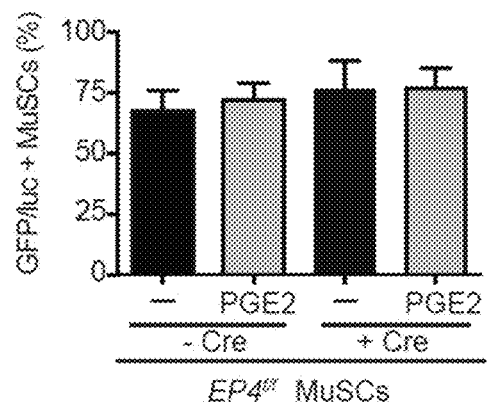
Figure 5K:
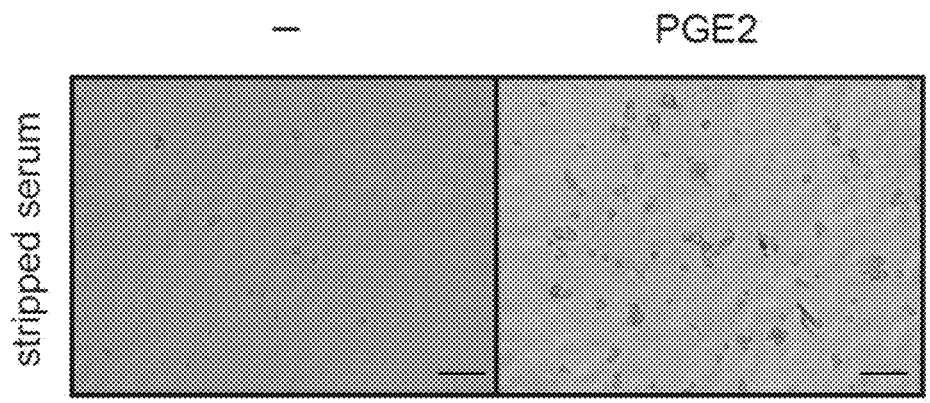
Figure 6A:
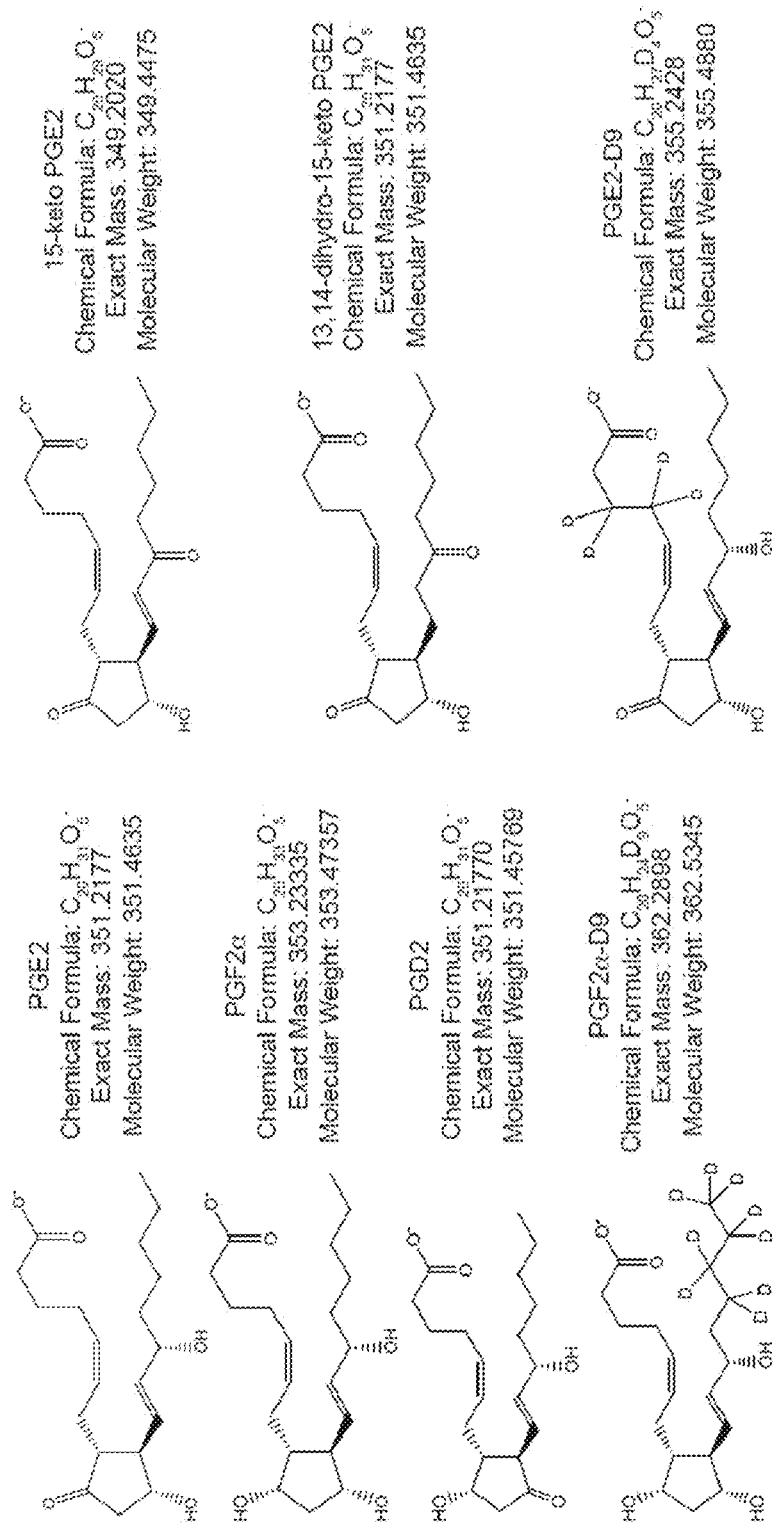
FIGS. 6A-6C show mass spectrometry analysis of young and aged muscle to detect prostaglandins and PGE2 metabolites.
Figure 6B:
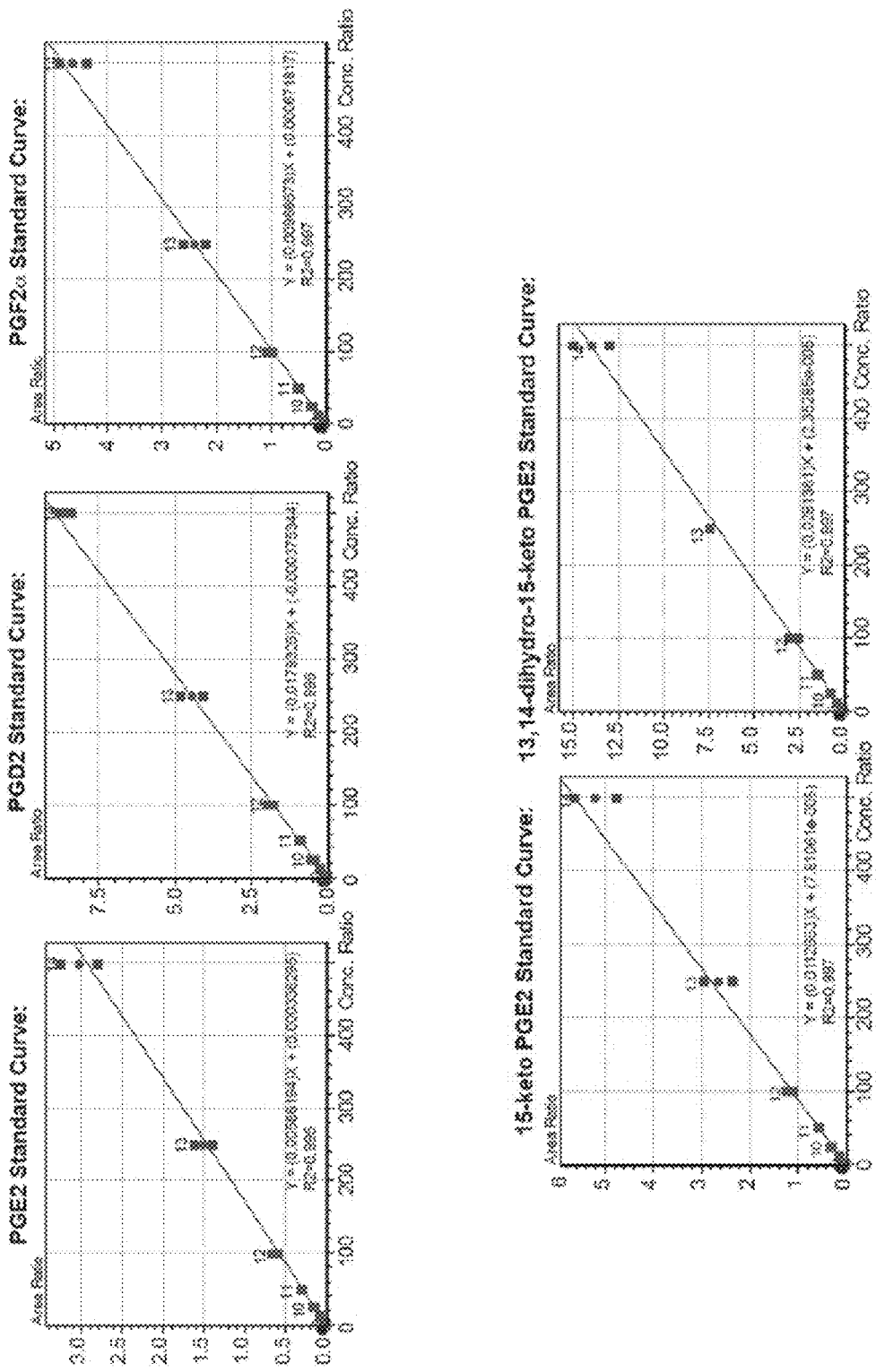
Figure 6C:
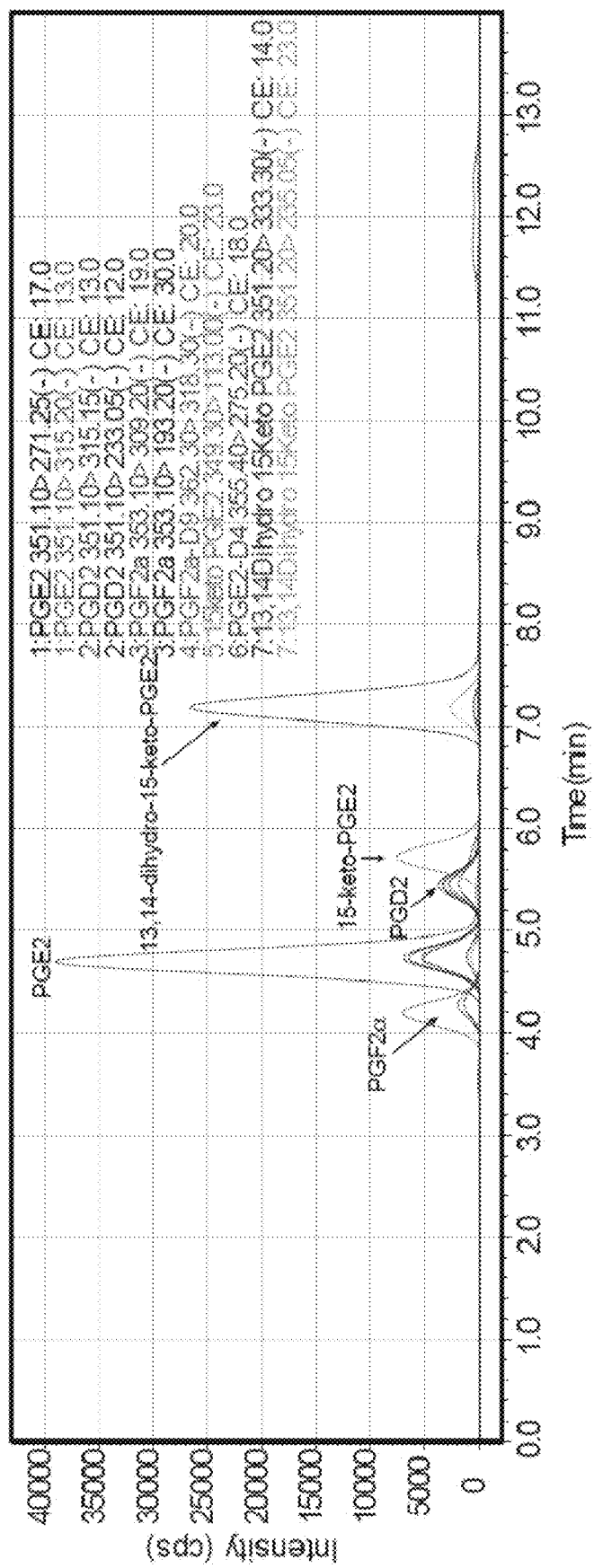

PGE2 is known to signal through four G-protein coupled receptors (Ptger1-4; EP1-4)[18,20], but the expression of these receptors in MuSCs has not previously been described. An analysis of the transcript levels of the different receptors (Ptger1-4) revealed that the only receptors upregulated after PGE2 treatment of MuSCs are Ptger1 and Ptger4 (FIG. 5E). PGE2 stimulated MuSCs had elevated intracellular cAMP[18,20] confirming that PGE2 signals through EP4 to promote proliferation and a stem cell transcriptional state (FIGS. 5F-5H). In the presence of an EP4 antagonist, ONO-AE3-208, proliferation induced by PGE2 was blunted (FIG. 1D). However, the specificity of PGE2 for EP4 was most clearly shown in MuSCs lacking the receptor following cre-mediated conditional ablation (FIGS. 1E-1G and FIGS. 5I-5J). Indeed, even in the presence of growth factor-rich media, these EP4-null MuSCs failed to proliferate. Finally, we found that MuSCs growth arrested by exposure to medium with charcoal stripped serum[21], divided upon addition of PGE2 (FIG. 1H and FIG. 5K). Thus, PGE2/EP4 stands out as necessary and sufficient for MuSC proliferation.

Figure 2A:
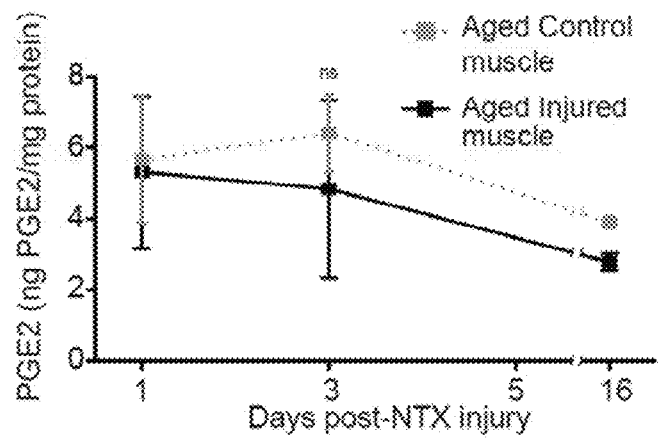
FIGS. 2A-2J show an aberrant response of aged MuSCs to PGE2.
Figure 2B:
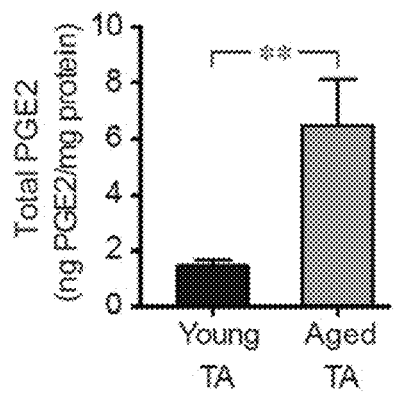
Figure 2C:
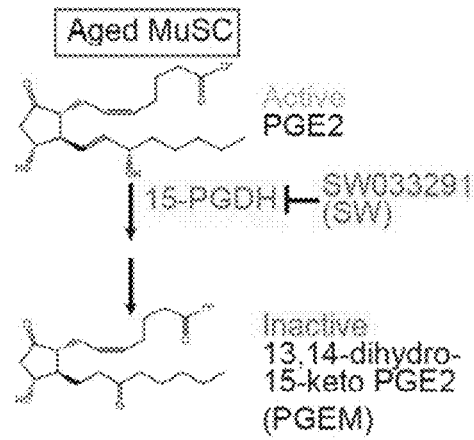
Figure 2D:
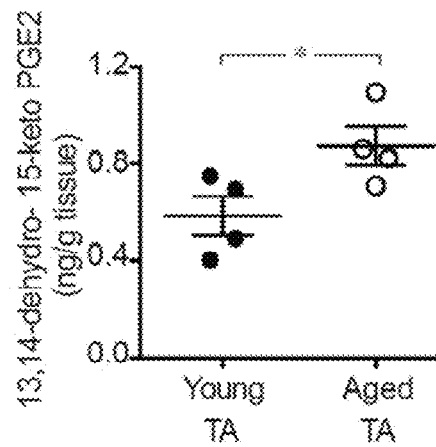
Figure 2E:
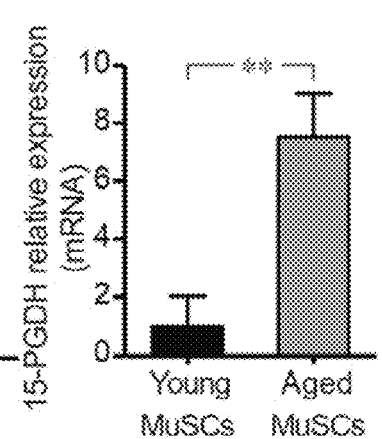
Figure 2F:
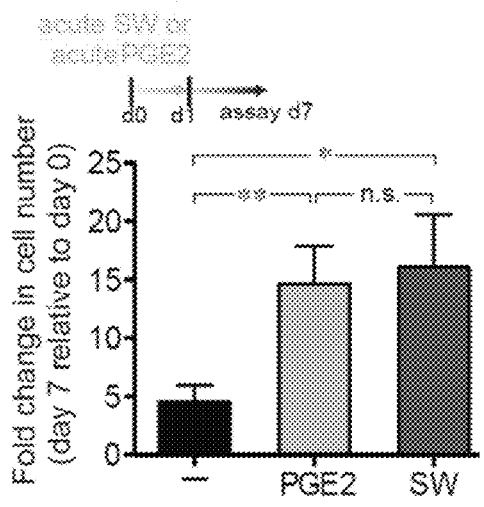
Figure 2G:
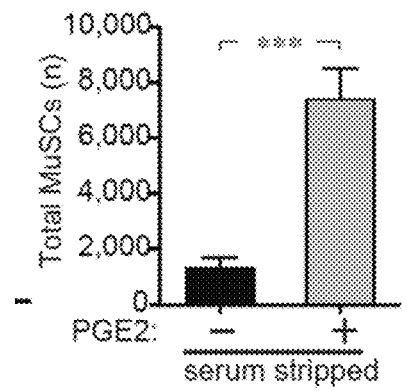
Figure 2H:
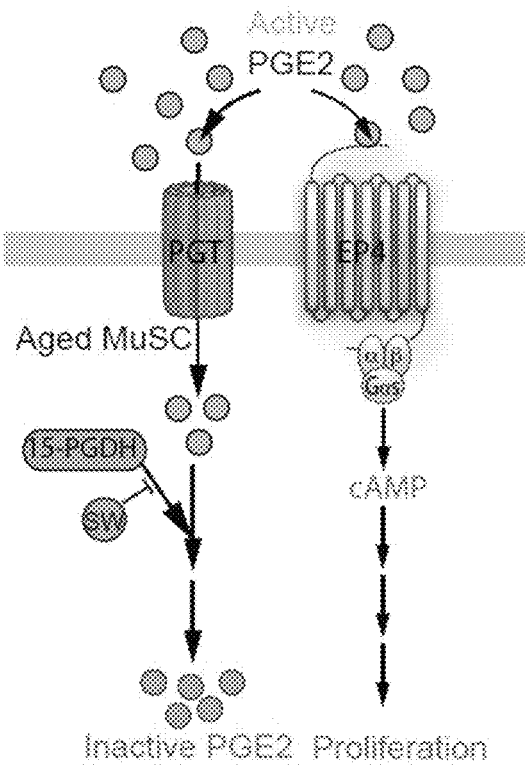
Figure 7F:
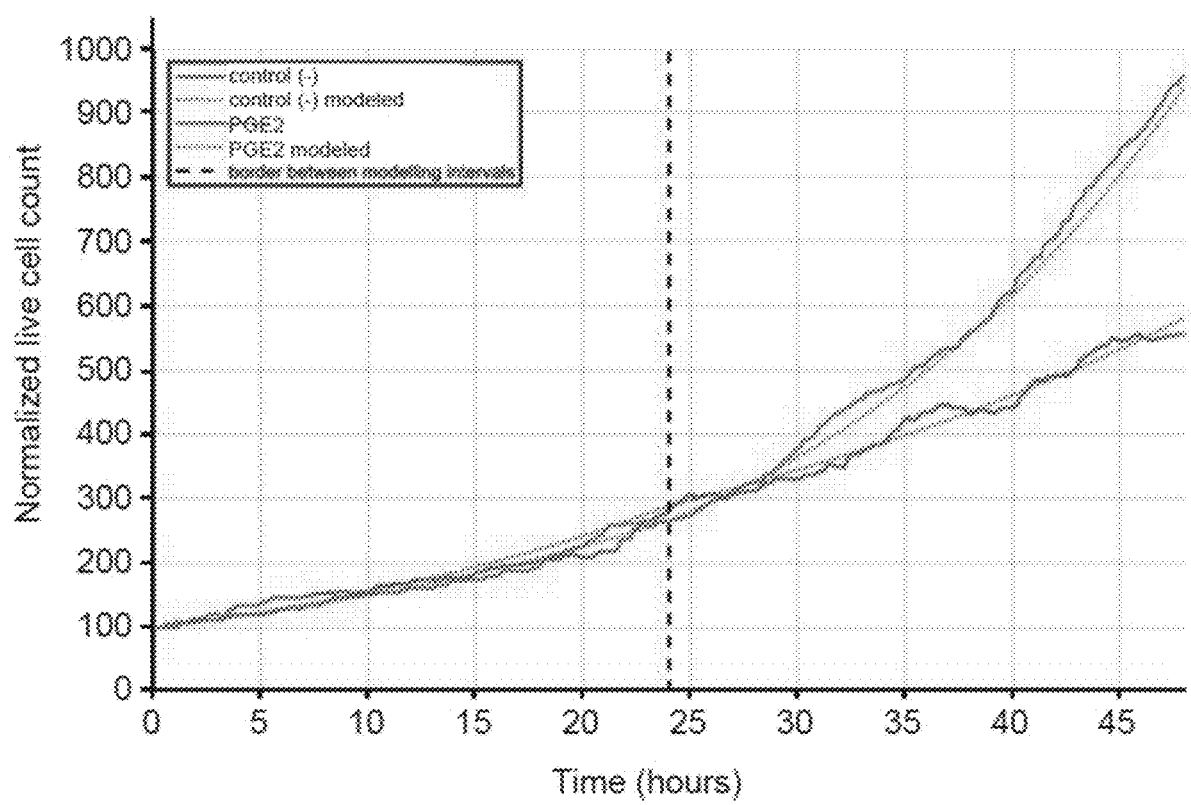
Figure 7G:
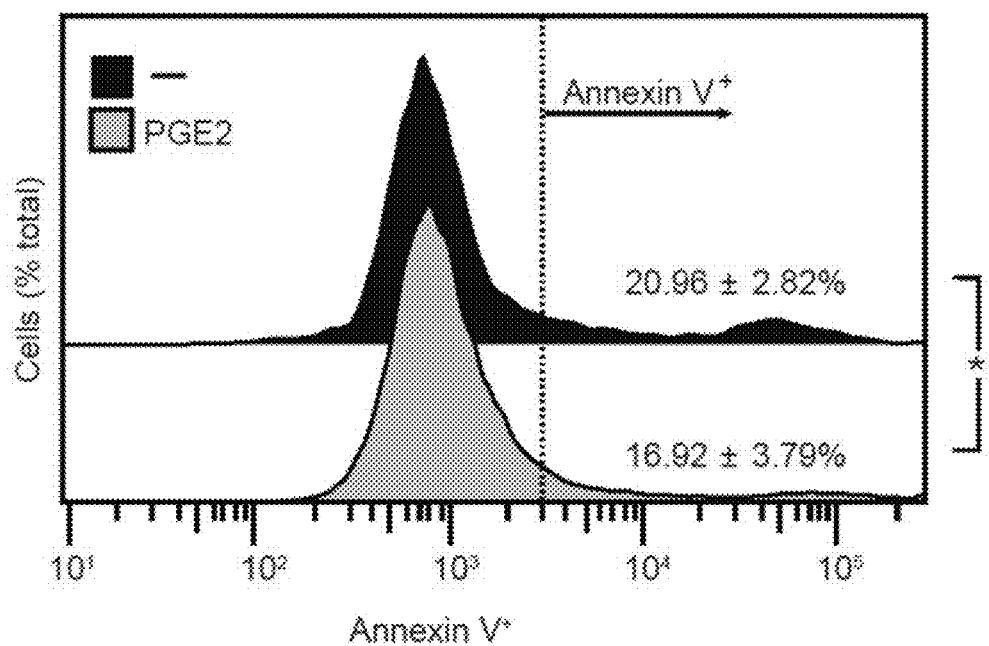
Figure 8A:
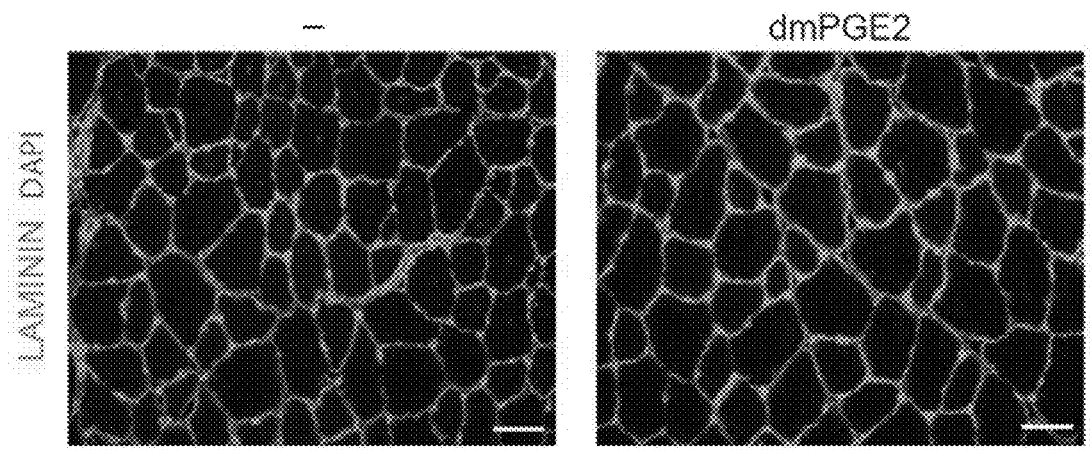
FIGS. 8A-8B show Baxter Algorithms for Myofiber Analysis of muscle cross-sectional area.
Figure 8B:
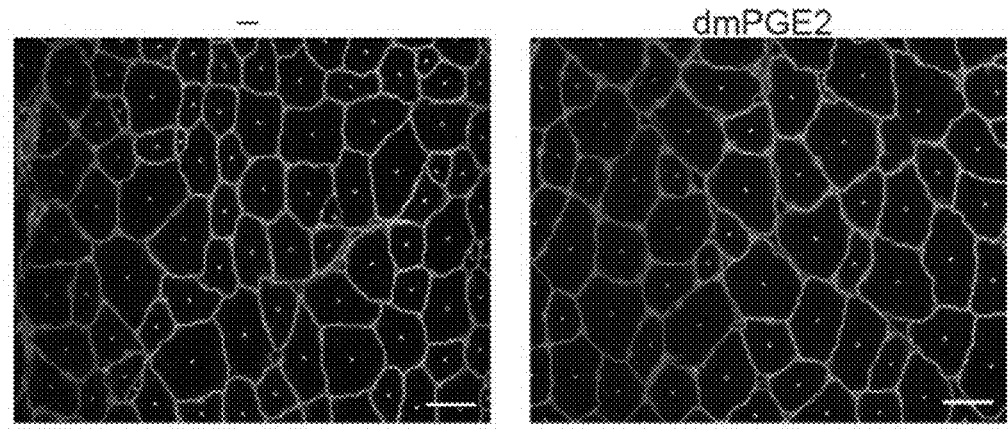

We sought to determine if PGE2 could ameliorate the muscle regenerative defects previously reported for aged MuSCs[9-13]. By contrast with young mouse muscles (2-4 mo), notexin damage to aged muscles (18-20 mo) did not lead to an increase in PGE2 synthesis. Instead, steady state PGE2 levels in aged muscle remained unchanged post injury (FIG. 2A) and were significantly higher than in young limb tibialis anterior (TA) muscles (FIG. 2B). We hypothesized that the PGE2 in aged muscle might be dysfunctional due to a catabolic defect. Indeed, when we analyzed the PGE2 present in young and aged TA muscle tissues by mass spectrometry, we found that the relative amount of the inactive form, 13,14-dihydro-15-keto PGE2 (PGEM), was significantly increased in the aged (FIGS. 2C-2D and FIGS. 6A-6C). This proved to be due to a concomitant 7-fold increase in levels of mRNA encoding the PGE2 degrading enzyme (15-PGDH), the initial step in the conversion of PGE2 to its inactive form (FIG. 2E). In contrast, the relative levels of the prostaglandin transporter (PGT), PGE2 synthesizing enzymes, and EP4 receptor did not differ between young and aged MuSCs (FIGS. 7A-7C). Additionally, when aged MuSCs were exposed to a 1-day pulse of PGE2 or to an inhibitor of 15-PGDH (SW033291)[22], the effects of 15-PGDH were overcome and the characteristic increase in proliferation and maintenance of Pax7 expression was observed (FIG. 2F and FIG. 7D). Like young, aged MuSCs failed to proliferate in medium comprised of charcoal stripped serum, but were rescued by addition of PGE2 alone (FIG. 2G). We surmised that in aged MuSCs the PGE2 pathway is dysregulated due to a cell intrinsic molecular defect, elevated 15-PGDH that can be surmounted in culture by acute exposure to PGE2 or SW (FIG. 2H).

Figure 2I:
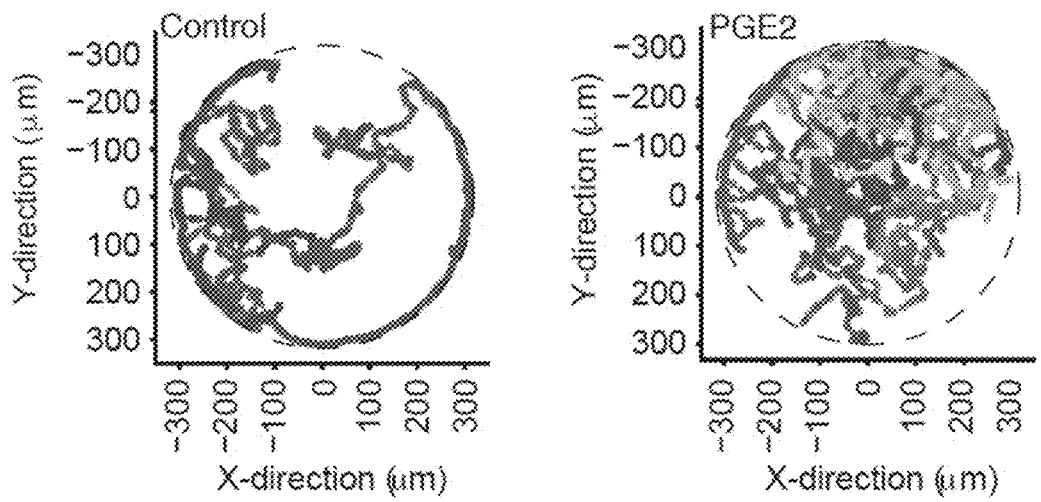
Figure 2J:
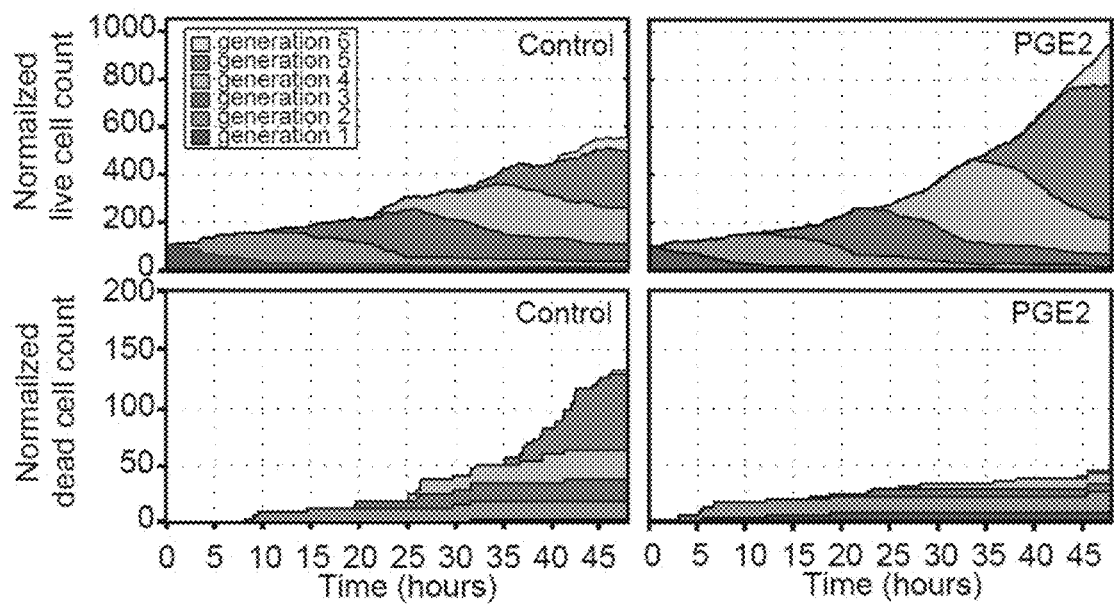

Since aged MuSCs are heterogeneous[10], we sought to determine the effect of PGE2 at the single cell level. Clonal analysis can reveal differences that are masked by analysis of the population as a whole. Accordingly, we performed long-term time-lapse microscopy in hydrogel 'microwells' of single aged MuSCs transiently exposed to PGE2 for 1 day and untreated control MuSCs. Data were collected over a 48 h time period and then analyzed using our previously described Baxter Algorithms for Cell Tracking and Lineage Reconstruction[10,19,23]. We observed a remarkable increase in cumulative cell numbers in response to PGE2, spanning 6 generations for the most robust clones (FIGS. 2I-2J). The numbers of cells per clone following PGE2 treatment were significantly augmented due to a marked increase in proliferation (FIGS. 2I-2J and FIGS. 7E-7F) that was accompanied by a profound reduction in cell death (FIG. 2J and FIGS. 7E-7G). These synergistic effects led to the observed increases in aged MuSC numbers in response to PGE2.

Figure 3A:
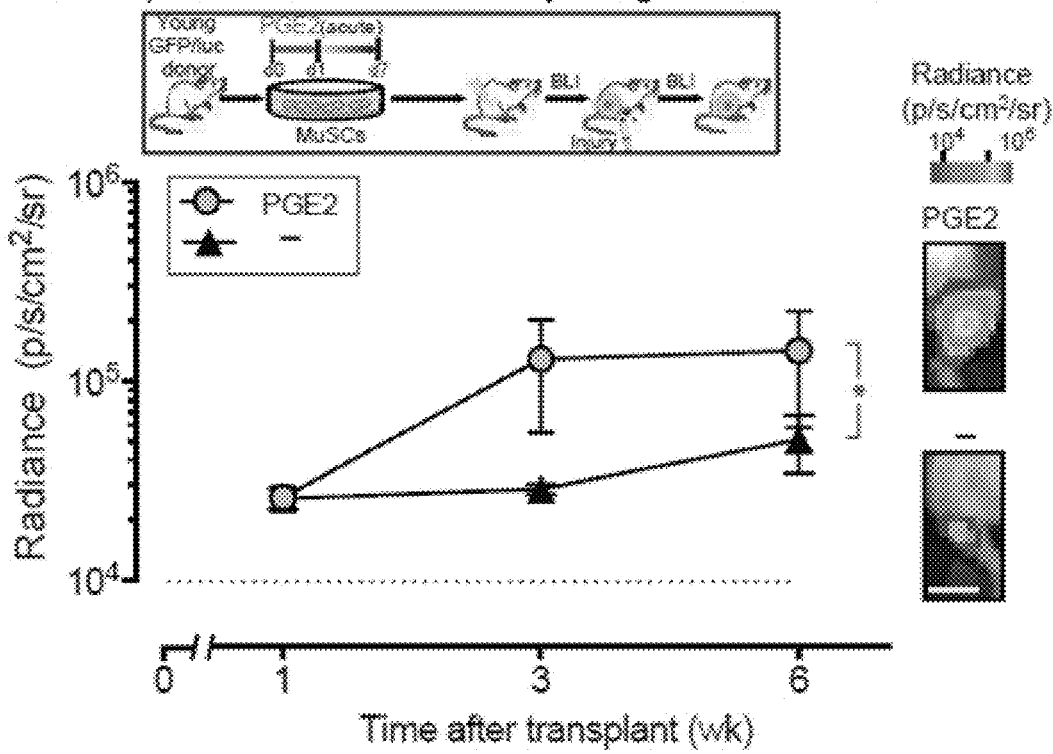
Figure 3B:
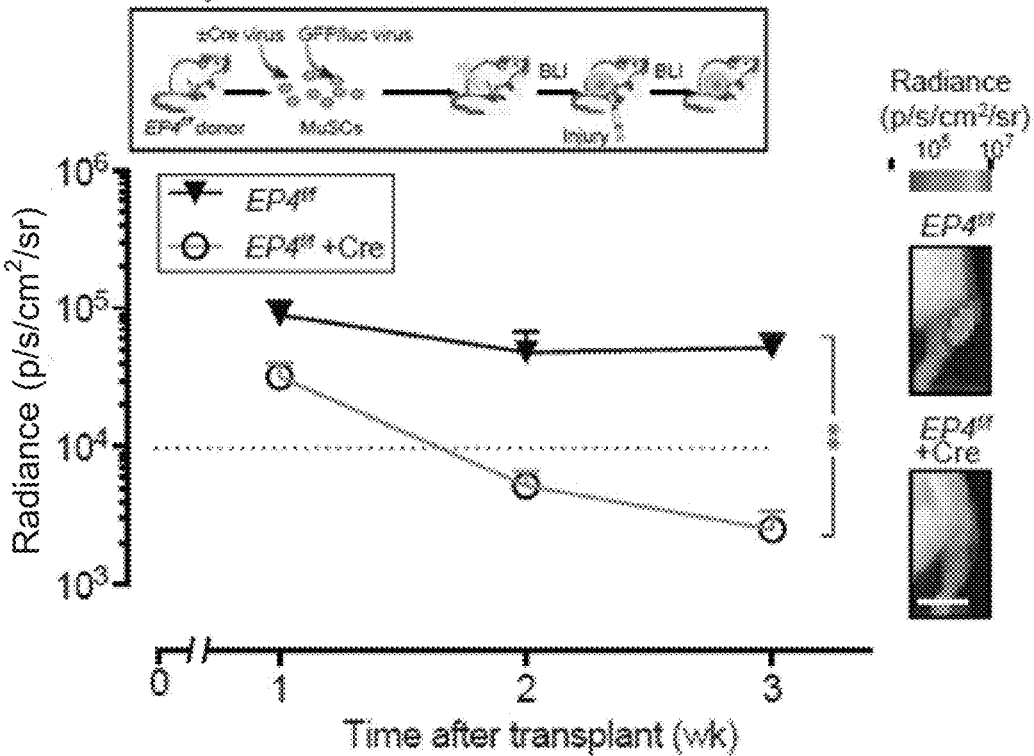

To test whether transient treatment of young MuSCs with PGE2 augments regeneration, we transplanted cultured PGE2 treated MuSCs into injured hindlimb muscles of mice. To monitor the dynamics of regeneration over time in a quantitative manner in vivo, we capitalized on a sensitive and quantitative bioluminescence imaging (BLI) assay we previously developed for monitoring MuSC function post-transplantation[6,10,19]. MuSCs were isolated from young transgenic mice (2-4 mo) expressing GFP and luciferase (GFP/Luc mice), exposed to an acute 1-day PGE2 treatment, harvested and transplanted on day 7. Equivalent numbers of dmPGE2 treated and control MuSCs (250 cells) were transplanted into injured hindlimbs of young (2-4 mo) NOD-SCID mice. Following acute treatment with PGE2, young MuSC regenerative capacity was enhanced by an order of magnitude when assessed by BLI (FIG. 3A). In contrast, following transplantation of 4-fold greater numbers of cultured MuSCs that lacked the EP4 receptor due to conditional ablation (FIG. 3B), the BLI signal that was initially detected progressively declined to levels below the threshold of significance (FIG. 3B).

Figure 9A:
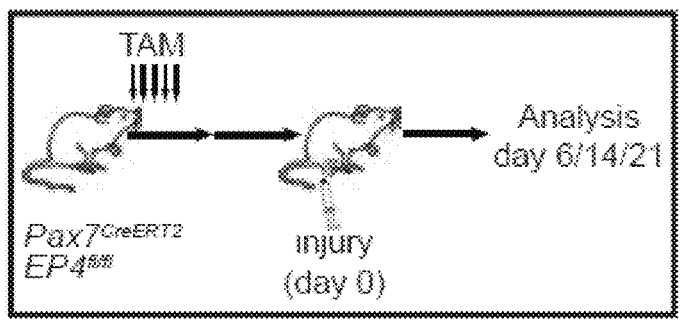
FIGS. 9A-9G show that deletion of PGE2 receptor EP4 in MuSCs decreases regeneration and force of skeletal muscle after injury. Tibialis anteriors (TAs) of Pax7-specific EP4 conditional knockout mice (Pax7$^{CreERT2}$;EP4$^{fl/fl}$) treated with tamoxifen were assayed at 6 (FIGS. 9C-9D), 21 (FIGS. 9B and 9E), and 14 (FIGS. 9F and 9G) days post-notexin injury; (n=3 mice per condition).
Figure 9B:
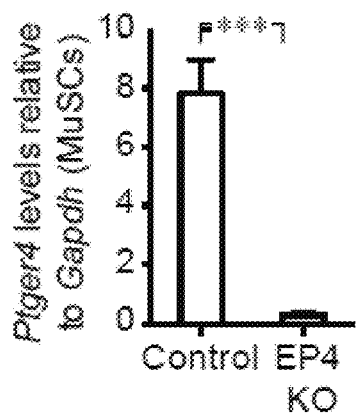
Figure 9C:
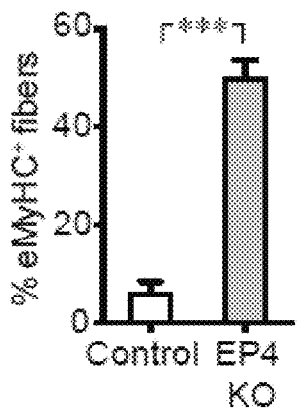
Figure 9D:
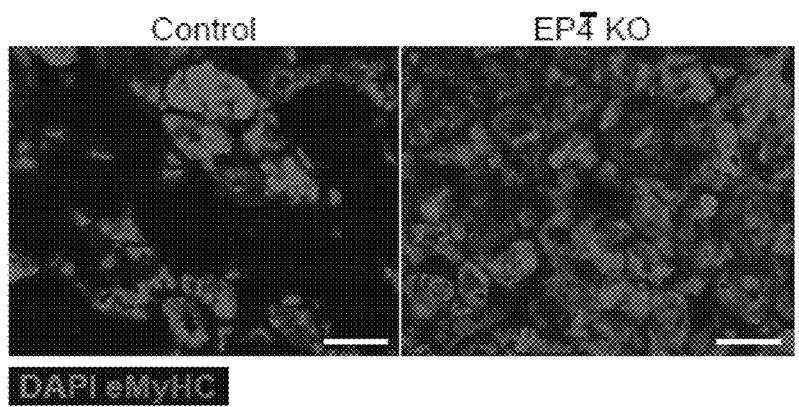
Figure 9E:
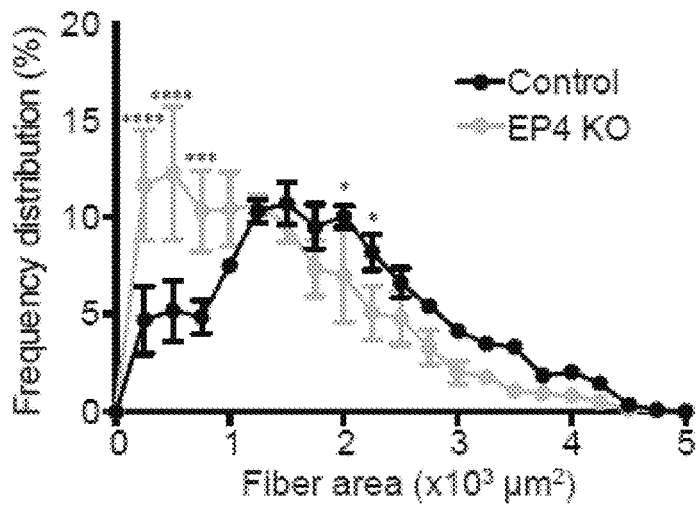
Figure 9F:
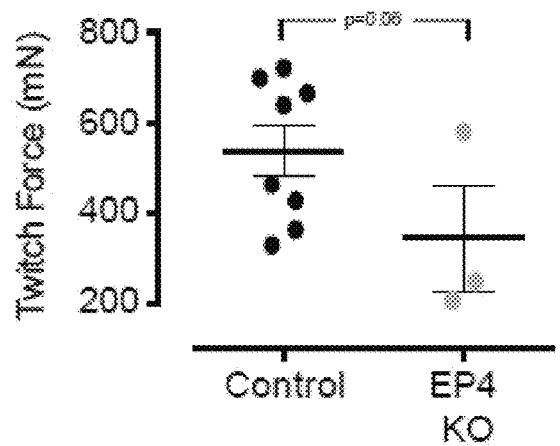
Figure 9G:
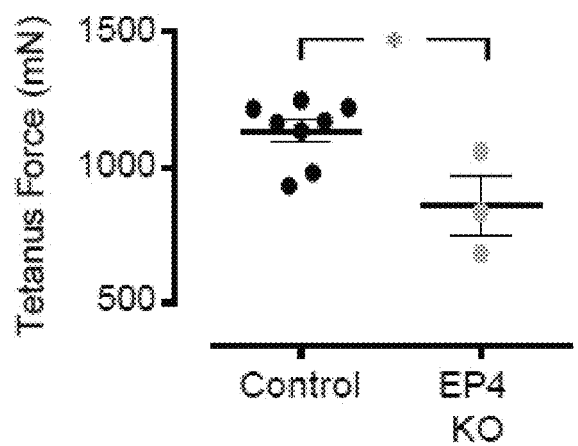

Furthermore, when notexin injury was performed in the mouse model of muscle stem cell specific deletion of EP4 (Pax7$^{CreET2}$;ErEP4$^{fl/fl}$) (FIGS. 9A-9B), muscle regeneration was impaired as observed by the elevated number of embryonic myosin heavy chain (eMHC) positive fibers (FIGS. 9C-9D). This was accompanied by the reduction in cross-sectional area of the mouse fibers in the Pax7$^{CreERT2}$;EP4$^{fl/f}$ group, assessed at the end of the regeneration time point (day 21) (FIG. 9E). A significant reduction in force output (tetanus) was also detected at day 14 post-injury (FIGS. 9F-9G). Thus, PGE2 signaling via the EP4 receptor is required for MuSC regeneration in vivo.

To test if direct injection of PGE2 without culture could be effective in promoting regeneration in vivo, we coinjected PGE2 together with freshly isolated MuSCs. For all subsequent in vivo injection experiments, we used a modified, more stable form of PGE2, 16,16-dimethyl PGE2 (dmPGE2)[24]. We hypothesized that for the aged MuSC experiments, the delivery of the modified 15-PGDH-resistant dmPGE2 was particularly important, as 15-PGDH is significantly elevated in aged MuSCs (FIG. 2E)[24]. Using dmPGE2, we observed significantly enhanced engraftment of young and aged MuSCs relative to controls that was further increased in response to notexin injury, a well-accepted stringent test of stem cell function (FIGS. 3C-3D). Thus, the delivery of dmPGE2 together with MuSC cell populations suffices to augment regeneration.

Figure 4A:
FIGS. 4A-4P show that intramuscular injection of PGE2 alone promotes MuSC expansion, improves regeneration, and increases force. Young.
Figure 4A:
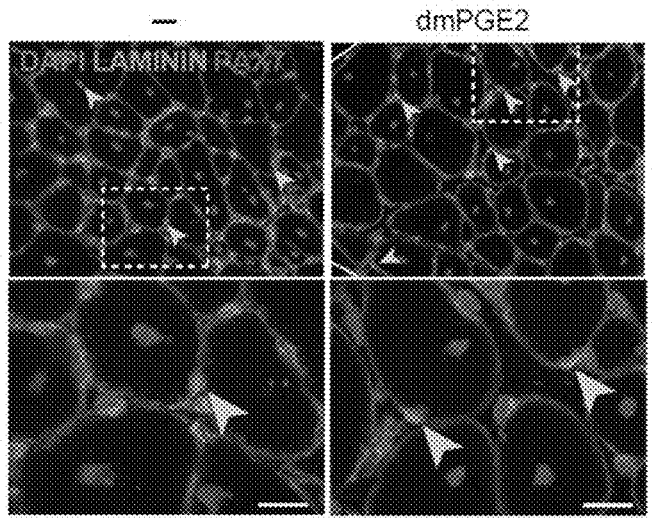
Figure 4B:
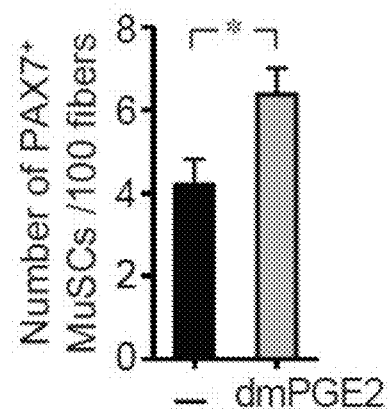
Figure 4C:
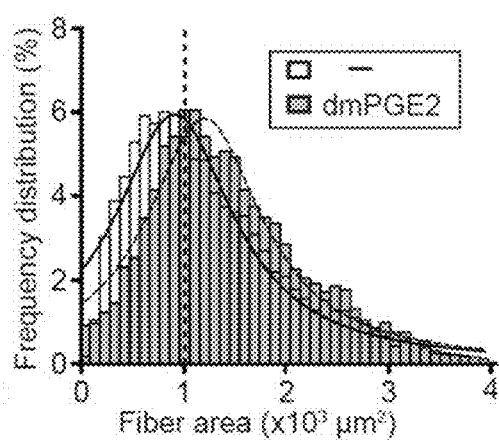
Figure 4D:
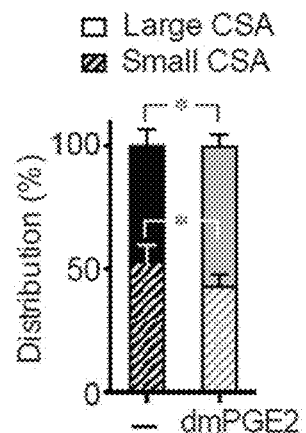
Figure 4E:
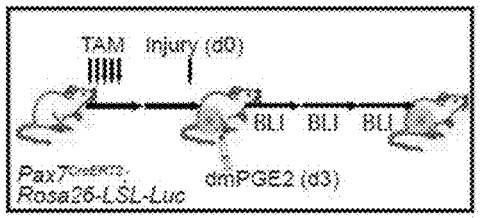
(FIGS. 4E-4G) Increase in endogenous MuSCs assayed by Pax7-luciferase. Pax7$^{CreERT2}$; Rosa26-LSL-Luc mice were treated intraperitoneally with tamoxifen (TAM), TAs subjected to cardiotoxin (CTX) injury, injected with vehicle (−) or dmPGE2 3 days later and monitored by BLI; (n=3 mice per condition).
Figure 4F:
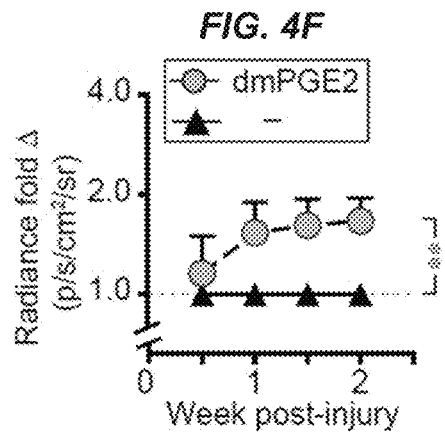
Figure 4G:
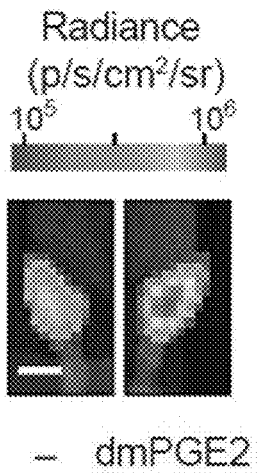

We postulated that delivery of PGE2 alone could stimulate muscle regeneration. To test this, muscles of young mice were injured with cardiotoxin and three days later a bolus of dmPGE2 was injected into the hindlimb muscles of young mice. We observed an increase (60+15%) in endogenous PAX7-expressing MuSCs in the classic satellite cell niche beneath the basal lamina and atop myofibers fourteen days post injury (FIGS. 4A-4B), whereas dmPGE2 had no effect in the absence of injury. Further, at this early time point, the distribution of myofibers shifted toward larger sizes, assessed as cross-sectional area using the Baxter Algorithms for Myofiber Analysis, suggesting that regeneration is accelerated by PGE2 (FIGS. 4C-4D and FIGS. 8A-8B). In addition, we tracked the response to injury and dmPGE2 of endogenous MuSCs by luciferase expression using a transgenic mouse model, Pax7$^{creERT2}$; Rosa26-LSL-Luc (FIG. 4E). The BLI data were in agreement with the histological data (FIGS. 4F-4G).

Figure 4H:
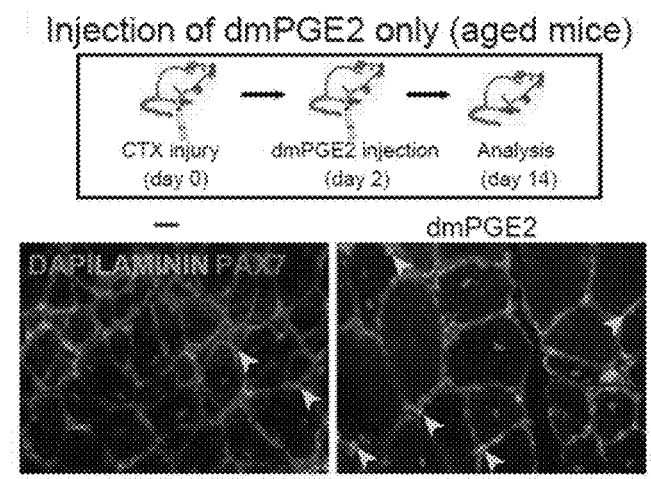
(FIGS. 4H-4K) TAs of aged mice were treated in vivo with vehicle (−) or dmPGE2 treatment 48 hr post-cardiotoxin (CTX) injury; (n=3 mice per condition).
Figure 4I:
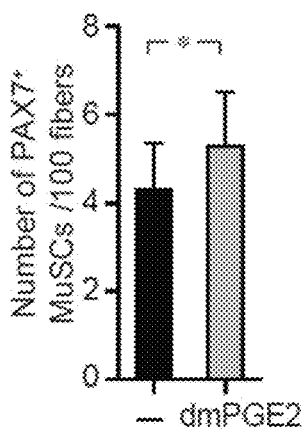
Figure 4J:
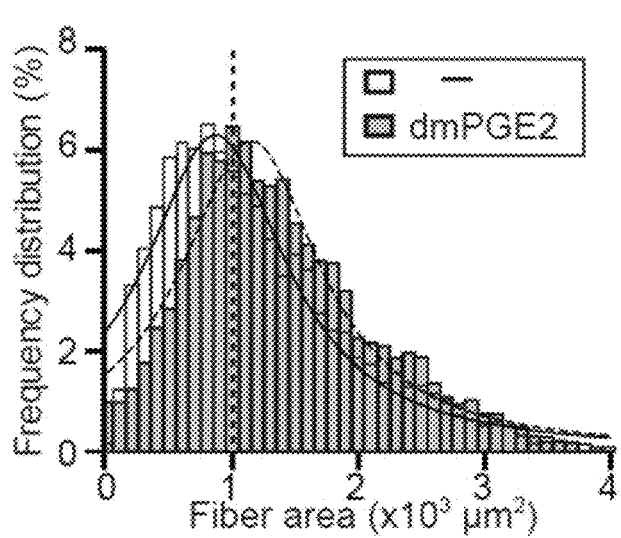
Figure 4K:
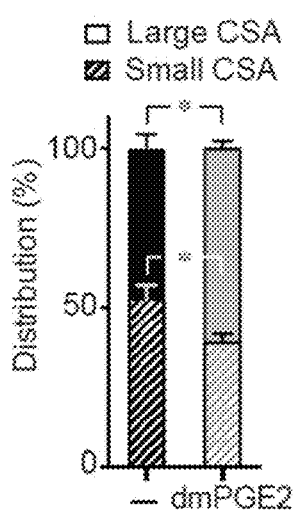
Figure 10A:
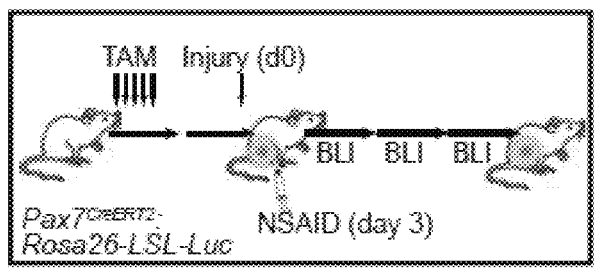
FIGS. 10A-10C show that blockage of endogenous PGE2 signaling in muscle at an early timepoint of regeneration reduces regeneration and force. Endogenous MuSCs assayed in Pax7$^{CreERT2}$; Rosa26-LSL-Luc mice treated with tamoxifen (TAM) by non-invasive bioluminescence imaging (BLI) after injection with vehicle (-) or NSAID (Indomethacin) post-cardiotoxin injury into the Tibialis anterior (TA); (n=3 mice per condition).
Figure 10B:
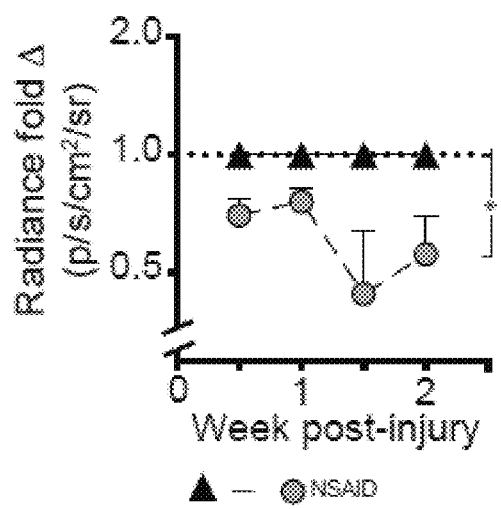
Figure 10C:
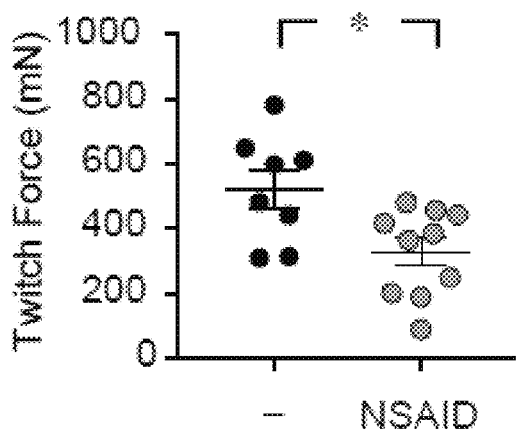

We tested the effects of injecting indomethacin, a non-steroidal anti-inflammatory drug (NSAID) and an inhibitor of COX2 which reduces PGE2 synthesis, on muscle regeneration. Upon indomethacin injection into the hindlimb muscles of the same Pax7$^{creERT2}$;Rosa26-LSL-Luc mouse model three days post-cardiotoxin injury, we observed a significant decrease in luciferase activity indicative of an impairment in muscle stem cell activation and regeneration (FIGS. 10A-10B). Injection of indomethacin into cardiotoxin-injured muscles also led to a significant loss in Twitch force as compared to the control group assessed at day 14 post-injury (FIG. 10C). In aged mice, we also detected a substantial increase (24±2%) in the number of endogenous MuSCs (FIGS. 4H-4I), and a concomitant increase in myofiber sizes (FIGS. 4J-4K) fourteen days post-injury after a single dmPGE2 injection. Thus, exposure solely to dmPGE2 impacts the magnitude and time course of the endogenous repair.

Figure 4L:
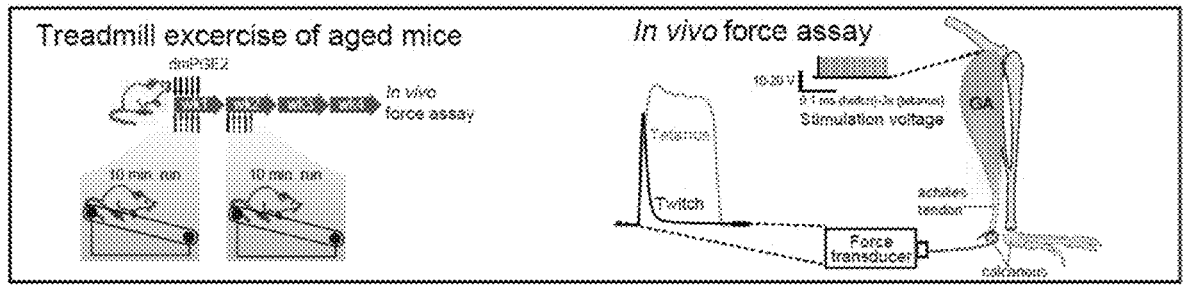

As the ultimate test, we determined if dmPGE2 enhanced regeneration could lead to increased muscle strength after a natural injury induced by downhill treadmill-running. In this scenario, damage was caused by a daily 10 min run on a downhill treadmill 20 degree decline[25]. During week one, aged mice in the treatment group ran for 5 days in succession and were injected daily with dmPGE2 after exercise. During week two, aged mice in the treatment group ran for 5 consecutive days but received no additional treatment (FIG. 4L). The specific twitch and tetanic force were compared for dmPGE2 treated and untreated gastrocnemius mouse muscles (GA) and both were significantly increased (FIGS. 4M-4P). Thus, an acute exposure to dmPGE2 concurrent with exercise-induced injury can confer a significant increase in aged muscle strength.

We have discovered a new indication for PGE2 in skeletal muscle regeneration. Prior studies of PGE2 effects on skeletal muscle have shown that it alters the proliferation, fusion, protein degradation, and differentiation of myoblasts in tissue culture[26-30]. Thus, these studies differ from ours as myoblasts are progenitors that have lost stem cell function. Satellite cells (MuSCs) are crucial to development and regeneration[3-8,31] and their numbers are increased by running or other high intensity exercise in young and aged mice and humans[15,32-36]. Non-steroidal anti-inflammatory agents have been reported to attenuate the exercise-induced increase in MuSCs[15,32-36]. Our data provide novel evidence that the beneficial effects of the early transient wave of inflammation that characterizes efficacious muscle regeneration[15] is due in part to PGE2 and its receptor EP4, which are essential and sufficient for MuSC proliferation and engraftment. For hematopoietic, liver, and colon tissues, delivery of the inhibitor of 15-PGDH, SW033291, was recently shown to enhance regeneration[22]. Notably, PGE2 and its analogues have safely been used in human patients for decades, for instance to induce labor[37] and to promote hematopoietic stem cell transplantation[38] paving the way for its clinical use in restoring muscles post-injury. In summary, our findings show that an acute PGE2 regimen suffices to rapidly and robustly enhance regeneration of exercise-induced damage and overcome age-associated limitations leading to increased strength.

References

1 Di Monaco, M., Vallero, F., Di Monaco, R. & Tappero, R. Prevalence of sarcopenia and its association with osteoporosis in 313 older women following a hip fracture. *Archives of Gerontology and Geriatrics* 52, 71-74 (2010).
2 Ruiz, J. R. et al. Association between muscular strength and mortality in men: prospective cohort study. *Bmj* 337, a439, doi: 10.1136/bmj.a439 (2008).
3 Chakkalakal, J. V., Jones, K. M., Basson, M. A. & Brack, A. S. The aged niche disrupts muscle stem cell quiescence. *Nature* 490, 355-360, doi: 10.1038/nature11438 (2012).
4 Mauro, A. Satellite cell of skeletal muscle fibers. *J Biophys Biochem Cytol* 9, 493-495 (1961).
Montarras, D. et al. Direct isolation of satellite cells for skeletal muscle regeneration. *Science* 309, 2064-2067, doi: 10.1126/science. 1114758 (2005).
6 Sacco, A., Doyonnas, R., Kraft, P., Vitorovic, S. & Blau, H. M. Self-renewal and expansion of single transplanted muscle stem cells. *Nature* 456, 502-506, doi: 10.1038/nature07384 (2008).
7 Kuang, S., Gillespie, M. A. & Rudnicki, M. A. Niche regulation of muscle satellite cell self-renewal and differentiation. *Cell stem cell* 2, 22-31, doi: 10.1016/j.stem.2007.12.012 (2008).
8 Shi, X. & Garry, D. J. Muscle stem cells in development, regeneration, and disease. *Genes & development* 20, 1692-1708, doi: 10.1101/gad. 1419406 (2006).
9 Bernet, J. D. et al. p38 MAPK signaling underlies a cell-autonomous loss of stem cell self-renewal in skeletal muscle of aged mice. *Nature medicine* 20, 265-271, doi:10.1038/nm.3465 (2014).
Cosgrove, B. D. et al. Rejuvenation of the muscle stem cell population restores strength to injured aged muscles. *Nature medicine* 20, 255-264, doi: 10.1038/nm.3464 (2014).
11 Price, F. D. et al. Inhibition of JAK-STAT signaling stimulates adult satellite cell function. *Nature medicine* 20, 1174-1181, doi:10.1038/nm.3655 (2014).
12 Sousa-Victor, P. et al. Geriatric muscle stem cells switch reversible quiescence into senescence. *Nature* 506, 316-321, doi: 10.1038/nature13013 (2014).
13 Tierney, M. T. et al. STAT3 signaling controls satellite cell expansion and skeletal muscle repair. *Nature medicine* 20, 1182-1186, doi: 10.1038/nm.3656 (2014).
14 Arnold, L. et al. Inflammatory monocytes recruited after skeletal muscle injury switch into antiinflammatory macrophages to support myogenesis. *The Journal of experimental medicine* 204, 1057-1069, doi: 10.1084/jem.20070075 (2007).
Chazaud, B. Inflammation during skeletal muscle regeneration and tissue remodeling: application to exercise-induced muscle damage management. *Immunol Cell Biol* 94, 140-145, doi: 10.1038/icb.2015.97 (2016).
16 Joe, A. W. et al. Muscle injury activates resident fibro/adipogenic progenitors that facilitate myogenesis. *Nature cell biology* 12, 153-163, doi: 10.1038/ncb2015 (2010).
17 Tidball, J. G. Mechanisms of muscle injury, repair, and regeneration. *Compr Physiol* 1, 2029-2062, doi: 10.1002/cphy.c100092 (2011).
18 Ricciotti, E. & FitzGerald, G. A. Prostaglandins and Inflammation. *Arteriosclerosis, Thrombosis, and Vascular Biology* 31, 986-1000 (2011).

19 Gilbert, P. M. et al. Substrate elasticity regulates skeletal muscle stem cell self-renewal in culture. *Science* 329, 1078-1081, doi: 10.1126/science. 1191035 (2010).

20 Korotkova, M. & Lundberg, I. E. The skeletal muscle arachidonic acid cascade in health and inflammatory disease. *Nature reviews. Rheumatology* 10, 295-303, doi: 10.1038/nrrheum.2014.2 (2014).

21 Smethurst, M. & Williams, D. C. Levels of prostaglandin E and prostaglandin F in samples of commercial serum used for tissue culture. *Prostaglandins* 13, 719-722 (1977).

22 Zhang, Y. et al. Inhibition of the prostaglandin-degrading enzyme 15-PGDH potentiates tissue regeneration. *Science* 348, aaa2340 (2015).

23 Magnusson, K. E., Jalden, J., Gilbert, P. M. & Blau, H. M. Global linking of cell tracks using the Viterbi algorithm. *IEEE transactions on medical imaging* 34, 911-929, doi:10.1109/TMI.2014.2370951 (2015).

24 Ohno, H., Morikawa, Y. & Hirata, F. Studies on 15-hydroxyprostaglandin dehydrogenase with various prostaglandin analogues. *Journal of biochemistry* 84, 1485-1494 (1978).

25 Sacco, A. et al. Short telomeres and stem cell exhaustion model Duchenne muscular dystrophy in mdx/mTR mice. *Cell* 143, 1059-1071, doi:10.1016/j.cell.2010.11.039 (2010).

26 Baracos, V., Rodemann, H. P., Dinarello, C. A. & Goldberg, A. L. Stimulation of muscle protein degradation and prostaglandin E2 release by leukocytic pyrogen (interleukin-1). A mechanism for the increased degradation of muscle proteins during fever. *The New England journal of medicine* 308, 553-558, doi: 10.1056/NEJM198303103081002 (1983).

27 Beaulieu, D. et al. Abnormal prostaglandin E2 production blocks myogenic differentiation in myotonic dystrophy. *Neurobiology of disease* 45, 122-129, doi:10.1016/j.nbd.2011.06.014 (2012).

28 Mo, C., Romero-Suarez, S., Bonewald, L., Johnson, M. & Brotto, M. Prostaglandin E2: from clinical applications to its potential role in bone-muscle crosstalk and myogenic differentiation. *Recent patents on biotechnology* 6, 223-229 (2012).

29 Mo, C. et al. Prostaglandin E2 promotes proliferation of skeletal muscle myoblasts via EP4 receptor activation. *Cell cycle* 14, 1507-1516, doi:10.1080/15384101.2015.1026520 (2015).

Rodemann, H. P. & Goldberg, A. L. Arachidonic acid, prostaglandin E2 and F2 alpha influence rates of protein turnover in skeletal and cardiac muscle. *J Biol Chem* 257, 1632-1638 (1982).

31 Pawlikowski, B., Pulliam, C., Betta, N. D., Kardon, G. & Olwin, B. B. Pervasive satellite cell contribution to uninjured adult muscle fibers. *Skeletal muscle* 5, 42, doi: 10.1186/s13395-015-0067-1 (2015).

32 Crameri, R. M. et al. Changes in satellite cells in human skeletal muscle after a single bout of high intensity exercise. *The Journal of physiology* 558, 333-340, doi: 10.1113/jphysiol.2004.061846 (2004).

33 Darr, K. C. & Schultz, E. Exercise-induced satellite cell activation in growing and mature skeletal muscle. *Journal of applied physiology* 63, 1816-1821 (1987).

34 Dreyer, H. C., Blanco, C. E., Sattler, F. R., Schroeder, E. T. & Wiswell, R. A. Satellite cell numbers in young and older men 24 hours after eccentric exercise. *Muscle & nerve* 33, 242-253, doi: 10.1002/mus.20461 (2006).

35 Mackey, A. L. et al. The influence of anti-inflammatory medication on exercise-induced myogenic precursor cell responses in humans. *Journal of applied physiology* 103, 425-431, doi: 10.1152/japplphysiol.00157.2007 (2007).

36 Paulsen, G., Mikkelsen, U. R., Raastad, T. & Peake, J. M. Leucocytes, cytokines and satellite cells: what role do they play in muscle damage and regeneration following eccentric exercise? *Exercise immunology review* 18, 42-97 (2012).

37 Thomas, J., Fairclough, A., Kavanagh, J. & Kelly, A. J. Vaginal prostaglandin (PGE2 and PGF2a) for induction of labour at term. *The Cochrane database of systematic reviews* 6, CD003101, doi:10.1002/14651858.CD003101.pub3 (2014).

38 North, T. E. et al. Prostaglandin E2 regulates vertebrate haematopoietic stem cell homeostasis. *Nature* 447, 1007-1011 (2007).

Methods

Mice

We performed all experiments and protocols in compliance with the institutional guidelines of Stanford University and Administrative Panel on Laboratory Animal Care (APLAC). We obtained wild-type aged C57BL/6 (18-20 mo) mice from the US National Institute on Aging (NIA) for aged muscle studies and young wild-type C57BL/6 mice from Jackson Laboratory. Double-transgenic GFP/luc mice were generated as described previously[1]. Briefly, mice expressing a firefly luciferase (luc) transgene under the regulation of the ubiquitous Actb promoter were maintained in the FVB strain. Mice expressing a green fluorescent protein (GFP) transgene under the regulation of the ubiquitous UBC promoter were maintained in the C57BL/6 strain. We used cells from GFP/luc for allogenic transplantation experiments into NOD-SCID (Jackson Laboratory) recipient mice. EP4$^{flox/flox}$ (EP4$^{f/f}$) mice were a kind gift from K. Andreasson (Stanford University)[2]. Double-transgenic Pax7$^{CreERT2}$;Rosa26-LSL-Luc were generated by crossing Pax7$^{CreERT2}$ mice obtained from Jackson Laboratory (Stock #017763)[3] and Rosa26-LSL-Luc obtained from Jackson Laboratory (Stock #005125)[4]. We validated these genotypes by appropriate PCR-based strategies. All mice from transgenic strains were of young age. Young mice were 2-4 mo. of age and aged mice were 18-20 mo of age for all strains. All mice used in these studies were females.

Muscle Stem Cell Isolation

We isolated and enriched muscle stem cells as previously described[1,5,6]. Briefly, a gentle collagenase digestion and mincing by the MACs Dissociator enabled numerous single fibers to be dissociated, followed by dispase digestion to release mononucleated cells from their niches. Subsequently, the cell mixture was depleted for hematopoietic lineage expressing and non-muscle cells (CD45$^-$/CD11b$^-$/CD31$^-$) using a magnetic bead column (Miltenyi). The remaining cell mixture was then subjected to FACS analysis to sort for MuSCs co-expressing CD34 and α7-integrin markers. We generated and analyzed flow cytometry scatter plots using FlowJo v10.0. For each sort, we pooled together MuSCs (~5,000 each) from at least three independent donor female mice.

Muscle Stem Cell Transplantation

We transplanted 250 MuSCs (FIGS. 3a, 3c and 3d) or 1,000 MuSCs (FIG. 3b) immediately following FACS isolation or after collection from cell culture directly into the tibialis anterior (TA) muscles of recipient mice as previously described[1,5,6]. For young MuSC studies, we transplanted cells from GFP/luc mice (2-4 mo of age) into hindlimb-irradiated NOD-SCID mice. For aged MuSCs studies, we transplanted cells from aged C57BL/6 mice (18-20 mo, NIH) that were transduced with a luc-IRES-GFP lentivirus (GFP/luc virus) on day 2 of culture for a period of 24 hr before transplantation, as previously described[5] (see below "Muscle stem cell culture, treatment and lentiviral infection" section for details). Prior to transplantation of muscle stem cells, we anesthetized NOD-SCID recipient mice with ketamine (2.4 mg per mouse) by intraperitoneal injection. We then irradiated hindlimbs with a single 18 Gy dose, with the rest of the body shielded in a lead jig. We performed transplantations within 2 d of irradiation.

Cultured cells were treated as indicated (vehicle or PGE2 treated 10 ng/ml) and collected from hydrogel cultures by incubation with 0.5% trypsin in PBS for 2 min at 37° C. and counted using a hemocytometer. We resuspended cells at desired cell concentrations in 0.1% gelatin/PBS and then transplanted them (250 MuSCs per TA) by intramuscular injection into the TA muscles in a 10 µl volume. For fresh MuSCs transplantation, we coinjected sorted cells with 13 nmol of 16,16-Dimethyl Prostaglandin E2 (dmPGE2) (Tocris, catalog #4027) or vehicle control (PBS). We compared cells from different conditions by transplantation into the TA muscles of contralateral legs in the same mice. One month after transplant, we injected 10 µl of notexin (10 µg ml$^{-1}$; Latoxan, France) to injure recipient muscles and to activate MuSCs in vivo. Eight weeks after transplantation, mice were euthanized and the TAs were collected for analysis.

Bioluminescence Imaging

We performed bioluminescence imaging (BLI) using a Xenogen-100 system, as previously described[1,5,6]. Briefly, we anesthetized mice using isofluorane inhalation and administered 120 µL D-luciferin (0.1 mmol kg$^{-1}$, reconstituted in PBS; Caliper LifeSciences) by intraperitoneal injection. We acquired BLI using a 60 s exposure at F-stop=1.0 at 5 minutes after luciferin injection. Digital images were recorded and analyzed using Living Image software (Caliper LifeSciences). We analyzed images with a consistent region-of-interest (ROI) placed over each hindlimb to calculate a bioluminescence signal. We calculated a bioluminescence signal in radiance (p s$^{-1}$ cm$^{-2}$ sr$^{-1}$) value of $10^4$ to define an engraftment threshold. This radiance threshold of $10^4$ is approximately equivalent to the total flux threshold in p/s reported previously. This BLI threshold corresponds to the histological detection of one or more GFP+ myofibers[1,5,6]. We performed BLI imaging every week after transplantation.

Muscle Injury

We used an injury model entailing intramuscular injection of 10 µl of notexin (10 µg ml$^{-1}$; Latoxan) or cardiotoxin (10 µM; Latoxan) into the TA muscle. For cryoinjury, an incision was made in the skin overlying the TA muscle and a copper probe, chilled in liquid nitrogen, was applied to the TA muscle for three 10 s intervals, allowing the muscle to thaw between each application of the cryoprobe. When indicated, 48 hr after injury either 16,16-Dimethyl Prostaglandin E2 (dmPGE2) (13 nmol, Tocris, catalog #4027) or vehicle control (PBS) was injected into the TA muscle. The contralateral TA was used as an internal control. We collected tissues 14 days post-injury for analysis.

For Pax7$^{CreERT2}$; Rosa26-LSL-Luc mice experiments, we treated mice with five consecutive daily intraperitoneal injections of tamoxifen to activate luciferase expression under the control of the Pax7 promoter. A week after the last tamoxifen injection, mice were subjected to intramuscular injection of 10 µl of cardiotoxin (10 µM; Latoxan), which we designated as day 0 of the assay. Three days later either 13 nmol dmPGE2 (13 nmol) or vehicle control (PBS) was injected into the TA muscle. The contralateral TA was used as an internal control. Bioluminescence was assayed at days 3, 7, 10 and 14 post-injury.

Tissue Histology

We collected and prepared recipient TA muscle tissues for histology as previously described[5,6]. We incubated transverse sections with anti-LAMININ (Millipore, clone A5, catalog #05-206, 1:200), and anti-PAX7 (Santa Cruz Biotechnology, catalog #sc-81648, 1:50) primary antibodies and then with AlexaFluor secondary Antibodies (Jackson ImmunoResearch Laboratories, 1:200). We counterstained nuclei with DAPI (Invitrogen). We acquired images with an Axio-Plan2 epifluorescent microscope (Carl Zeiss Microimaging) with Plan NeoFluar 10×/0.30NA or 20×/0.75NA objectives (Carl Zeiss) and an ORCA-ER digital camera (Hamamatsu Photonics) controlled by the SlideBook (3i) software. The images were cropped using Adobe Photoshop with consistent contrast adjustments across all images from the same experiment. The image composites were generated using Adobe Illustrator. We analyzed the number of PAX7 positive cells using the MetaMorph Image Analysis software (Molecular Devices), and the fiber area using the Baxter Algorithms for Myofiber Analysis that identified the fibers and segmented the fibers in the image to analyze the area of each fiber. For PAX7 quantification we examined serial sections spanning a depth of at least 2 mm of the TA. For fiber area at least 10 fields of LAMININ-stained myofiber cross-sections encompassing over 400 myofibers were captured for each mouse as above. Data analyses were blinded. The researchers performing the imaging acquisition and scoring were unaware of treatment condition given to sample groups analyzed.

Hydrogel Fabrication

We fabricated polyethylene glycol (PEG) hydrogels from PEG precursors, synthesized as described previously[6]. Briefly, we produced hydrogels by using the published formulation to achieve 12-kPa (Young's modulus) stiffness hydrogels in 1 mm thickness which is the optimal condition for culturing MuSCs and maintaining stem cell fate in culture[6]. We fabricated hydrogel microwell arrays of 12-kPa for clonal proliferation experiments, as described previously[6]. We cut and adhered all hydrogels to cover the surface area of 12-well or 24-well culture plates.

Muscle Stem Cell Culture, Treatment and Lentiviral Infection

Following isolation, we resuspended MuSCs in myogenic cell culture medium containing DMEM/F10 (50:50), 15% FBS, 2.5 ng ml$^{-1}$ fibroblast growth factor-2 (FGF-2 also known as bFGF) and 1% penicillin-streptomycin. We seeded MuSC suspensions at a density of 500 cells per cm$^2$ surface area. We maintained cell cultures at 37° C. in 5% $CO_2$ and changed medium daily. For PGE2, 15-PGDH inhibitor and EP4 receptor antagonist treatment studies, we added 1-200 ng/ml Prostaglandin E2 (Cayman Chemical) (unless specified in the figure legends, 10 ng/ml was the standard concentration used), and/or 1 µM EP4 antagonist (ONO-AE3-208, Cayman Chemical), or 1 µM 15-PGDH inhibitor (SW033291, Cayman Chemical) to the MuSCs cultured on collagen coated dishes for the first 24 h. The cells were then trypsinized and cells reseeded onto hydrogels for an additional 6 days of culture. All treatments were compared to their solvent (DMSO) vehicle control. For stripped serum assays, we resuspended isolated MuSCs in medium containing DMEM/F10 (50:50), 15% charcoal stripped FBS (Gibco, cat #12676011), 2.5 ng ml$^{-1}$ bFGF and 1% penicillin-streptomycin. When noted in the figure, we additionally added 1.5 µg/ml insulin (Sigma, 10516) and 0.25 µM dexamethasone (Sigma, D8893) to stripped serum cell medium. For these experiments MuSCs were cultured on hydrogels and vehicle (DMSO) or 10 ng/ml PGE2 (Cayman Chemical) was added to the cultures with every media change (every two days). Proliferation (see below) was assayed 7 days later.

We performed all MuSC culture assays and transplantations after 1 week of culture unless noted otherwise. For aged MuSCs transplant studies, we infected MuSCs with lentivirus encoding elongation factor-1α promoter-driven luc-IRES-GFP (GFP/luc virus) for 24 h in culture as described previously[3]. For EP4$^{f/f}$ MuSCs studies, we isolated MuSCs as described above (Muscle stem cell isolation), and infected all cells with the GFP/luc virus and a subset of them was coinfected with a lentivirus encoding pLM-CMV-R-Cre (mCherry/Cre virus) for 24 h in culture. pLM-CMV-R-Cre was a gift from Michel Sadelain (Addgene plasmid #27546)[7]. We transplanted aged MuSC (250 cells) or EP4$^{f/f}$ MuSCs (1,000 cells) into young (2-4 mo) 18-gy irradiated TAs of NOD-SCID recipient mice. For in vitro proliferation assays, EP4$^{f/f}$ MuSCs were plated on hydrogels post-infection and treated for 24 hr with vehicle (DMSO) or 10 ng/ml PGE2, and proliferation was assayed 3 days later. Cells were assayed for GFP and/or mCherry expression 48 h post-infection using an inverted fluorescence microscope (Carl Zeiss Microimaging). MuSCs are freshly isolated from the mice by FACS and put in culture for a maximum time period of one week, therefore *mycoplasma* contamination is not assessed.

Proliferation Assays

To assay proliferation, we used three different assays (hemocytometer, VisionBlue, and EdU). For each, we seeded MuSCs on flat hydrogels (hemocytometer and VisionBlue) or collagen-coated plates (EdU assay) at a density of 500 cells per cm² surface area. For hemocytometer cell number count, we collected cells at indicated timepoints by incubation with 0.5% trypsin in PBS for 5 min at 37° C. and quantified them using a hemocytometer at least 3 times. Additionally, we used the VisionBlue Quick Cell Viability Fluorometric Assay Kit (BioVision, catalog #K303) as a readout for cell growth in culture. Briefly, we incubated MuSCs with 10% VisionBlue in culture medium for 3 h, and measured fluorescence intensity on a fluorescence plate reader (Infinite M1000 PRO, Tecan) at Ex=530-570 nm, Em=590-620 nm. We assayed proliferation using the Click-iT EdU Alexa Fluor 555 Imaging kit (Life Technologies). Briefly, we incubated live cells with EdU (20 μM) for 1 hr prior to fixation, and stained nuclei according to the manufacturer's guidelines together with anti-MYOGENIN (Santa Cruz, catalog #sc576, 1:250) to assay differentiation. We counterstained nuclei with DAPI (Invitrogen). We acquired images with an AxioPlan2 epifluorescent microscope (Carl Zeiss Microimaging) with Plan NeoFluar 10x/0.30NA or 20x/0.75NA objectives (Carl Zeiss) and an ORCA-ER digital camera (Hamamatsu Photonics) controlled by SlideBook (3i) software. We quantified EdU positive cells using the MetaMorph Image Analysis software (Molecular Devices). Data analyses were blinded, where researchers performing cell scoring were unaware of the treatment condition given to sample groups analyzed.

Clonal Muscle Stem Cell Proliferation and Fate Analyses

We assayed clonal muscle stem cell proliferation by time-lapse microscopy as previously described[5,6]. Briefly, we treated isolated aged MuSCs with PGE2 (Cayman Chemical) or vehicle (DMSO) for 24 hr. After five days of growth on hydrogels, cells were reseeded at a density of 500 cells per cm² surface area in hydrogel microwells with 600 μm diameter. For time-lapse microscopy we monitored cell proliferation for those wells with single cells beginning 12 hr (day 0) to two days after seeding and recorded images every 3 min at 10× magnification using a PALM/AxioObserver Z1 system (Carl Zeiss MicroImaging) with a custom environmental control chamber and motorized stage. We changed medium every other day in between the acquisition time intervals. We analyzed time-lapse image sequences using the Baxter Algorithms for Cell Tracking and Lineage Reconstruction to identify and track single cells and generate lineage trees[5,6,8-10].

Viable and dead cells were distinguished in time-lapse sequences based on phase-contrast boundary and motility maintenance or loss, respectively. We found that the rates of proliferation (division) and death in the two conditions varied over time, Therefore, we estimated the rates for the first and the second 24 hour intervals separately. The values were estimated using the equations described in[6], and found in Table 1. We denote the proliferation rates in the two intervals $p_{24}$ and $p_{48}$ and the corresponding death rates $d_{24}$ and $d_{48}$. As an example, the proliferation rate in the treated condition during the second 24 hour interval is 5.38% per hour. Table 1 (below) shows that the rates of proliferation and death in the two conditions are similar in the first time interval, and that the difference in cell numbers at the end of the experiment is due to differences in both the division rates and the death rates during the second time interval. The modeled cell counts in the two time intervals are given by $$c(t) = \begin{cases} c_0 \exp((p_{24} - d_{24})t) & 0 \le t \le 24 \\ c(24) \exp((p_{48} - d_{48})(t - 24)) & 24 < t \le 48 \end{cases}$$

where $c_0$ is the number of cells at the onset. The modeled curves are plotted together with the actual cell counts in FIG. 7F.

TABLE 1

Estimated proliferation and death rates per hours.

| | $p_{24}$ | $p_{48}$ | $d_{24}$ | $d_{48}$ |
|---|---|---|---|---|
| DMSO | 0.0488 | 0.0403 | 0.0045 | 0.0112 |
| E2 | 0.0475 | 0.0538 | 0.0067 | 0.0012 |

The data analysis was blinded. The researchers performing the imaging acquisition and scoring were unaware of the treatment condition given to sample groups analyzed.

Quantitative RT-PCR

We isolated RNA from MuSCs using the RNeasy Micro Kit (Qiagen). For muscle samples, we snap froze the tissue in liquid nitrogen, homogenized the tissues using a mortar and pestle, followed by syringe and needle trituration, and then isolated RNA using Trizol (Invitrogen). We reverse-transcribed cDNA from total mRNA from each sample using the SensiFAST™ cDNA Synthesis Kit (Bioline). We subjected cDNA to RT-PCR using SYBR Green PCR Master Mix (Applied Biosystems) or TaqMan Assays (Applied Biosystems) in an ABI 7900HT Real-Time PCR System (Applied Biosystems). We cycled samples at 95° C. for 10 min and then 40 cycles at 95° C. for 15 s and 60° C. for 1 min. To quantify relative transcript levels, we used 2-ΔΔCt to compare treated and untreated samples and expressed the results relative to Gapdh. For SYBR Green qRT-PCR, we used the following primer sequences: Gapdh. forward 5'-TT-CACCACCATGGAGAAGGC-3' (SEQ ID NO: 1), reverse 5'-CCCTTTTGGCTCCACCCT-3' (SEQ ID NO: 2); Hpgd, forward 5'-TCCAGTGTGATGTGGCTGAC-3' (SEQ ID NO: 3), reverse 5'-ATTGITCACGCCTGCATTGT-3' (SEQ ID NO: 4); Ptges, forward 5'-GCTGTCAT-CACAGGCCAGA-3' (SEQ ID NO: 5), reverse 5'-CTCCA-CATCTGGGTCACTCC-3' (SEQ ID NO: 6); Ptges2, forward 5'-CTCCTACAGGAAAGTGCCCA-3' (SEQ ID NO: 7), reverse 5'-ACCAGGTAGGTCITGAGGGC-3' (SEQ ID NO: 8); Ptger1, forward 5' GTGGTGTCGTGCATCTGCT-3' (SEQ ID NO: 9), reverse, 5' CCGCTGCAGGGAGT-TAGAGT-3' (SEQ ID NO: 10), and Ptger2, forward 5'-ACCTTCGCCATATGCTCCIT-3' (SEQ ID NO: 11), reverse 5'-GGACCGGTGGCCTAAGTATG-3' (SEQ ID NO: 12). TaqMan Assays (Applied Biosystems) were used to quantify Pax7. Myogenin. Slco2a1 (PGT), Ptger3 and Ptger4 in samples according to the manufacturer instructions with the TaqMan Universal PCR Master Mix reagent kit (Applied Biosystems). Transcript levels were expressed relative to Gapdh levels. For SYBR Green qPCR, Gapdh qPCR was used to normalize input cDNA samples. For Taqman qPCR, multiplex qPCR enabled target signals (FAM) to be normalized individually by their internal Gapdh signals (VIC).

PGE2 Elisa

Muscle was harvested, rinsed in ice-cold PBS containing indomethacin (5.6 μg/ml), and snap frozen in liquid nitrogen. Frozen samples were pulverized in liquid nitrogen. The powder was transferred to an Eppendorf tube with 500 μl of lysate buffer (50 mM Tris-HCl pH 7.5, 150 mM NaCl, 4 mM CaCl, 1.5% Triton X-100, protease inhibitors and micrococcal nuclease), and then homogenized using a tissue homogenizer. The PGE2 level of the supernatant was measured using a PGE2 ELISA Kit (R&D Systems, catalog #KGE004B) and expressed relative to total protein measured by BCA assay (BioRad) and expressed as ng of PGE2. Each sample was assayed in duplicate and in each of two independent experiments.

cAMP Activity Assay

MuSCs were treated with DMSO (vehicle) or PGE2 (10 ng/ml) for 1 h and cyclic AMP levels measured according to the cAMP-Glo Assay protocol optimized by the manufacturer (Promega). Each sample was assayed in triplicate and in two independent experiments.

Flow Cytometry

We assayed Annexin V as a readout of apoptosis for MuSCs after 7 days in culture on hydrogels, after an initial acute (24 hr) treatment of vehicle (DMSO) or PGE2 (10 ng/ml). We used the FITC Annexin V Apoptosis Detection Kit (Biolegend, cat #640914) according to the protocol of the manufacturer. We analyzed the cells for Annexin V on a FACS LSR II cytometer using FACSDiva software (BD Biosciences) in the Shared FACS Facility, purchased using an NIH S10 Shared Instrument Grant (S10RR027431-01).

Mass Spectrometry

Analytes:

All prostaglandin standards—PGF2α; PGE2; PGD2; 15-keto PGE2; 13,14-dihydro 15-keto PGE2; PGE2-D4; and PGF2α-D9—were purchased from Cayman Chemical. For the PGE2-D4 internal standard, positions 3 and 4 were labeled with a total of four deuterium atoms. For PGF2α-D9, positions 17, 18, 19 and 20 were labeled with a total of nine deuterium atoms.

Calibration Curve Preparation:

Analyte stock solutions (5 mg/mL) were prepared in DMSO. These stock solutions were serially diluted with acetonitrile/water (1:1 v/v) to obtain a series of standard working solutions, which were used to generate the calibration curve. Calibration curves were prepared by spiking 10 uL of each standard working solution into 200 μL of homogenization buffer (acetone/water 1:1 v/v; 0.005% BHT to prevent oxidation) followed by addition of 10 uL internal standard solution (3000 ng/mL each PGF2α-D9 and PGE2-D4). A calibration curve was prepared fresh with each set of samples. Calibration curve ranges: for PGE2 and 13,14-dihydro 15-keto PGE2, from 0.05 ng/mL to 500 ng/mL; for PGD2 and PGF2α, from 0.1 ng/mL to 500 ng/mL; and for 15-keto PGE2, from 0.025 ng/mL to 500 ng/mL.

Extraction Procedure:

The extraction procedure was modified from that of Prasain et al.[11] and included acetone protein precipitation followed by 2-step liquid-liquid extraction; the latter step enhances LC-MS/MS sensitivity. Butylated hydroxytoluene (BHT) and evaporation under nitrogen ($N_2$) gas were used to prevent oxidation.

Solid tissues were harvested, weighed, and snap-frozen with liquid nitrogen. Muscle tissue was combined with homogenization beads and 200 μL homogenization buffer in a polypropylene tube and processed in a FastPrep 24 homogenizer (MP Biomedicals) for 40 seconds at a speed of 6 m/s. After homogenization, 10 μL internal standard solution (3000 ng/mL) was added to tissue homogenate followed by sonication and shaking for 10 minutes. Samples were centrifuged and the supernatant was transferred to a clean eppendorf tube. 200 μL hexane was added to the sample, followed by shaking for 15 minutes, then centrifugation. Samples were frozen at −80° C. for 40 minutes. The hexane layer was poured off from the frozen lower aqueous layer, and discarded. After thawing, 25 μL of IN formic acid was added to the bottom aqueous layer, and the samples were vortexed. For the second extraction, 200 μL chloroform was added to the aqueous phase. Samples were shaken for 15 minutes to ensure full extraction. Centrifugation was performed to separate the layers. The lower chloroform layer was transferred to a new eppendorf tube and evaporated to dryness under nitrogen at 40° C. The dry residue was reconstituted in 100 μL acetonitrile/10 mM ammonium acetate (2:8 v/v) and analyzed by LC-MS/MS.

LC-MS/MS:

Since many prostaglandins are positional isomers with identical masses and have similar fragmentation patterns, chromatographic separation is critical. Two SRM transitions—one quantifier and one qualifier—were carefully selected for each analyte. Distinctive qualifier ion intensity ratios and retention times were essential to authenticate the target analytes. All analyses were carried out by negative electrospray LC-MS/MS using an LC-20AD$_{XR}$ prominence liquid chromatograph and 8030 triple quadrupole mass spectrometer (Shimadzu). HPLC conditions: Acquity UPLC BEH C18 2.1×100 mm, 1.7 um particle size column was operated at 50° C. with a flow rate of 0.25 mL/min. Mobile phases consisted of A: 0.1% acetic acid in water and B: 0.1% acetic acid in acetonitrile. Elution profile: initial hold at 35% B for 5 minutes, followed by a gradient of 35%-40% in 3 minutes, then 40%-95% in 3 minutes; total run time was 14 minutes. Injection volume was 20 uL. Using these HPLC conditions, we achieved baseline separation of the analytes of interest.

Selected reaction monitoring (SRM) was used for quantification. The mass transitions were as follows: PGD2: m/z 351.10→m/z 315.15 (quantifier) and m/z 351.10→m/z 233.05 (qualifier); PGE2: m/z 351.10→m/z 271.25 (quantifier) and m/z 351.10→m/z 315.20 (qualifier); PGF2α: m/z 353.10→m/z 309.20 (quantifier) and m/z 353.10→m/z 193.20 (qualifier); 15 keto-PGE2: m/z 349.30→m/z 331.20

(quantifier) and m/z 349.30→m/z 113.00 (qualifier); 13,14-dihydro 15-keto PGE2: m/z 351.20→m/z 333.30 (quantifier) and m/z 351.20→m/z 113.05 (qualifier); PGE2-D4: m/z 355.40→m/z 275.20; and PGF2α-D9: m/z 362.20→m/z 318.30. Dwell time was 20-30 ms.

Quantitative analysis was done using LabSolutions LCMS (Shimadzu). An internal standard method was used for quantification: PGE2-D4 was used as an internal standard for quantification of PGE2, 15-keto PGE2, and 13,14-dihydro 15-keto PGE2. PGF2α-D9 was the internal standard for quantification of PGD2 and PGF2α. Calibration curves were linear (R>0.99) over the concentration range using a weighting factor of $1/X^2$ where X is the concentration. The back-calculated standard concentrations were ±15% from nominal values, and ±20% at the lower limit of quantitation (LLOQ).

In Vive Muscle Force Measurement

Aged mice (18 mo.) were subjected to downhill treadmill run for 2 consecutive weeks. During week 1, mice ran daily for 5 days and rested on days 6 and 7. Two hours after each treadmill run during week 1, each (lateral and medial) gastrocnemius (GA) muscle from both legs of each mouse was injected with a dose of either PBS (vehicle control) or 13 nM dmPGE2 (experimental group). During week 2, mice were subjected to 5 days treadmill run only. The treadmill run was performed using the Exer3/6 (Columbus Instruments). Mice ran for 10 minutes on the treadmill at 20 degrees downhill, starting at a speed of 7 meters/min. After 3 min, the speed was increased by 1 meter/min to a final speed of 14 meter/min. 10 minutes run time was chosen, as exhaustion defined as the inability of the animal to remain on the treadmill despite electrical prodding, was observed at a median of 12 minute in an independent control aged mouse group. Force measurements were on the GA muscles at week 5 based on a protocol published previously[5]. Briefly, for each mouse, an incision was made to expose the GA. We severed the calcaneus bone with intact achilles tendon and attached the tendon-bone complex to a 300C-LR force transducer (Aurora Scientific) with a thin metal hook. The muscles and tendons were kept moist by periodic wetting with saline (0.9% sodium chloride) solution. The lower limb was immobilized below the knee by a metal clamp without compromising the blood supply to the leg. The mouse was under inhaled anesthetic (2% isofluorane) during the entire force measuring procedure and body temperature was maintained by a heat lamp. In all measurements, we used 0.1-ms pulses at a predetermined supramaximal stimulation voltage. The GA muscles were stimulated via the proximal sciatic nerve using a bipolar electrical stimulation cuff delivering a constant current of 2 mA (square pulse width 0.1 ms). GA muscles were stimulated with a single 0.1-ms pulse for twitch force measurements, and a train of 150 Hz for 0.3 s pulses for tetanic force measurements. We performed five twitch and then five tetanic measurements on each muscle, with 2-3 min recovery between each measurement with n=5 mice per group. Data were collected with a PCI-6251 acquisition card (National Instruments) and analyzed in Matlab. We calculated specific force values by normalizing the force measurements by the muscle physiological cross-sectional areas (PCSAs), which were similar between the control and the experimental PGE2 treated group (Table 2). PCSA (measured in $mm^2$) was calculated according to the following equation[12]:

$$\text{PCSA (mm}^2\text{)} = [\text{mass (g)} \times \cos\theta] \div [\rho(g/mm^3) \times \text{fiber length (mm)}],$$

where θ is pennation angle of the fiber and ρ is muscle density (0.001056 $g/mm^3$).

Statistical Analyses

We performed cell culture experiments in at least three independent experiments where three biological replicates were pooled in each. In general, we performed MuSC transplant experiments in at least two independent experiments, with at least 3-5 total transplants per condition. We used a paired t-test for experiments where control samples were from the same experiment in vitro or from contralateral limb muscles in vivo. A non-parametric Mann-Whitney test was used to determine the significance difference between untreated (−) vs treated (PGE or dmPGE2) groups using α=0.05. ANOVA or multiple t-test was performed for multiple comparisons with significance level determined using Bonferroni correction or with Fisher's test as indicated in the figure legends. Unless otherwise described, data are shown as the mean±s.e.m.

Methods References

1 Sacco, A., Doyonnas, R., Kraft, P., Vitorovic, S. & Blau, H. M. Self-renewal and expansion of single transplanted muscle stem cells. *Nature* 456, 502-506, doi: 10.1038/nature07384 (2008).

2 Schneider, A. et al. Generation of a conditional allele of the mouse prostaglandin EP4 receptor. *Genesis* 40, 7-14, doi: 10.1002/gene.20048 (2004).

3 Murphy, M. M., Lawson, J. A., Mathew, S. J., Hutcheson, D. A. & Kardon, G. Satellite cells, connective tissue fibroblasts and their interactions are crucial for muscle regeneration. *Development* 138, 3625-3637, doi:10.1242/dev.064162 (2011).

4 Safran, M. et al. Mouse reporter strain for noninvasive bioluminescent imaging of cells that have undergone Cre-mediated recombination. *Molecular imaging* 2, 297-302 (2003).

Cosgrove, B. D. et al. Rejuvenation of the muscle stem cell population restores strength to injured aged muscles. *Nature medicine* 20, 255-264, doi: 10.1038/nm.3464 (2014).

6 Gilbert, P. M. et al. Substrate elasticity regulates skeletal muscle stem cell self-renewal in culture. *Science* 329, 1078-1081, doi: 10.1126/science. 1191035 (2010).

7 Papapetrou, E. P. et al. Genomic safe harbors permit high beta-globin transgene expression in thalassemia induced pluripotent stem cells. *Nature biotechnology* 29, 73-78, doi:10.1038/nbt.1717 (2011).

8 Chenouard, N. et al. Objective comparison of particle tracking methods. *Nature methods* 11, 281-289, doi: 10.1038/nmeth.2808 (2014).

9 Magnusson, K. E., Jalden, J., Gilbert, P. M. & Blau, H. M. Global linking of cell tracks using the Viterbi algorithm. *IEEE transactions on medical imaging* 34, 911-929, doi: 10.1109/TMI.2014.2370951 (2015).

10 Maska, M. et al. A benchmark for comparison of cell tracking algorithms. *Bioinformatics* 30, 1609-1617, doi: 10.1093/bioinformatics/btu080 (2014).

11 Prasain, J. K., Hoang, H. D., Edmonds, J. W. & Miller, M. A. Prostaglandin extraction and analysis in *Caenorhabditis elegans*. *Journal of visualized experiments: JoVE*, doi:10.3791/50447 (2013).

12 Burkholder, T. J., Fingado, B., Baron, S. & Lieber, R. L. Relationship between muscle fiber types and sizes and muscle architectural properties in the mouse hindlimb. *J Morphol* 221, 177-190, doi: 10.1002/jmor.1052210207 (1994).

TABLE 2

Physiological cross-sectional area (PCSA) of aged gastrocnemius week 5 post-exercise.

| Mouse ID | Leg | Pennation angle θ (degree) | Cosine(θ) | Fiber length (mm) | GA Mass (g) | PCSA (medial + lateral) (mm$^2$) |
|---|---|---|---|---|---|---|
| Control-1 | Left | 21 | 0.93 | 6.88 | 0.18 | 23.13 |
| | Right | 21 | 0.93 | 6.64 | 0.18 | 23.82 |
| Control-2 | Left | 26 | 0.90 | 4.03 | 0.16 | 33.79 |
| | Right | 22 | 0.93 | 5.34 | 0.16 | 26.31 |
| Control-3 | Left | 21 | 0.93 | 4.52 | 0.15 | 29.34 |
| | Right | 23 | 0.92 | 4.59 | 0.17 | 32.28 |
| Control-4 | Left | 24 | 0.91 | 5.07 | 0.14 | 23.89 |
| | Right | 23 | 0.92 | 4.75 | 0.13 | 23.86 |
| Control-5 | Left | 19 | 0.95 | 6.07 | 0.16 | 17.75 |
| | Right | 18 | 0.95 | 6.05 | 0.15 | 10.25 |
| dmPGE2-1 | Left | 12 | 0.98 | 7.60 | 0.25 | 30.47 |
| | Right | Tendon damage | — | — | — | — |
| dmPGE2-2 | Left | 12 | 0.96 | 4.85 | 0.16 | 30.56 |
| | Right | 16 | 0.91 | 4.80 | 0.14 | 26.55 |
| dmPGE2-3 | Left | 14 | 0.97 | 5.89 | 0.17 | 26.52 |
| | Right | 13 | 0.94 | 5.63 | 0.14 | 22.94 |
| dmPGE2-4 | Left | 14 | 0.97 | 6.67 | 0.14 | 19.29 |
| | Right | 13 | 0.97 | 7.74 | 0.16 | 19.07 |
| dmPGE2-5 | Left | 11 | 0.98 | 5.56 | 0.17 | 28.42 |
| | Right | 11 | 0.98 | 5.54 | 0.16 | 26.85 |
| Avg. Control | | | | | | 25.09 |
| Avg. dmPGE2 | | | | | | 25.63 |

Example 2: Increased Muscle Forces After Prostaglandin E2 (PGE2) Injection

This example shows an increase in specific twitch force of gastrocnemius muscles in aged mice injected with PGE2. The aged mice (18 months old) were subject to treadmill run to exhaustion daily for 10 days. The treadmill run was performed using the Exer3/6 (Columbus Instruments). Mice ran on the treadmill at 20 degrees downhill, starting at a speed of 10 meters/min. After 3 min, the speed was increased 1 meter/min to a final speed of 20 meters/min. Exhaustion was defined as the inability of the animal to remain on the treadmill despite electrical prodding. 2 h after each treadmill run, both gastrocnemius muscles of each mouse were injected with either PBS (control group) or 3 nM PGE2 (experimental group). The force measurement was performed 4 weeks after the last treadmill run using a 300C-LR force transducer (Aurora Scientific) with a single 0.1 ms pulse at predetermined supramaximal stimulation intensity.

Figure 4M:
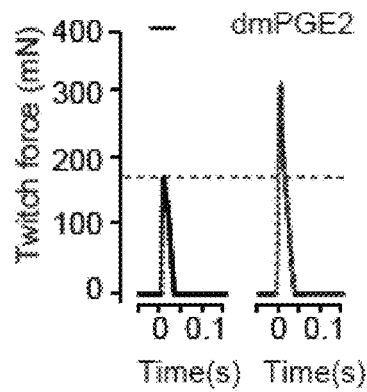
Figure 4N:
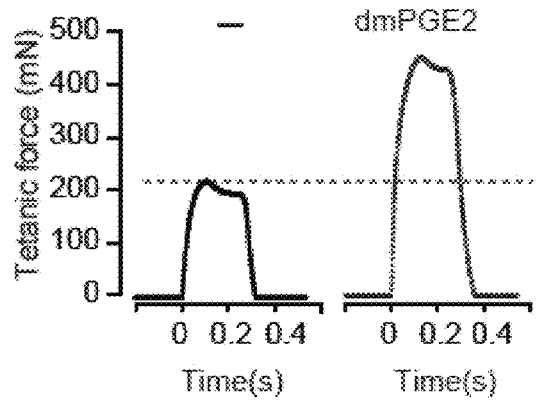
Figure 4O:
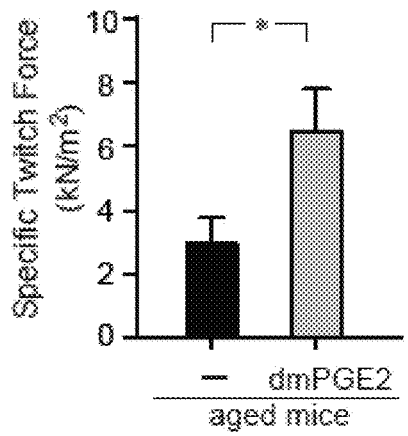
Figure 4P:
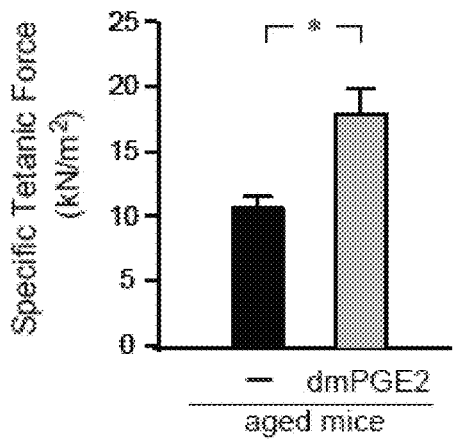

Representative raw muscle force traces of single gastrocnemius muscles are provided in FIGS. 4M-4N. The muscle force and synchronization pulses were recorded via a PCI-6251 acquisition card (National Instruments) and analyzed using Matlab. FIGS. 4O-4P show the specific muscle force values that were calculated by normalizing the force measurements with the muscle physiological cross-sectional area. The specific twitch force values (kN/m$^2$) are represented by the Box and Whiskers plot that shows the minimum, maximum, and median values. Five repetitive measurements were made from each muscle. N=4 for the control group and n=5 for the PGE2 injected group. ** represents a statistical significant value of p<0.005 by 2-tailed Mann Whitney test.

VI. Exemplary Embodiments

Exemplary embodiments provided in accordance with the presently disclosed subject matter include, but are not limited to, the claims and the following embodiments:

1. A method for stimulating the proliferation of a population of isolated muscle cells, the method comprising:
   culturing the population of isolated muscle cells with a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof.

2. The method of embodiment 1, wherein the population of isolated muscle cells is purified.

3. The method of embodiment 1 or 2, wherein the population of isolated muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof.

4. The method of any one of embodiments 1 to 3, wherein the population of isolated muscle cells comprises muscle stem cells, satellite cells, myocytes, myoblasts, myotubes, myofibers, or a combination thereof.

5. The method of any one of embodiments 1 to 4, wherein the population of isolated muscle cells is obtained from a subject.

6. The method of embodiment 5, wherein the subject has a condition or disease associated with muscle damage, injury, or atrophy.

7. The method of embodiment 6, wherein the condition or disease associated with muscle damage, injury, or atrophy is selected from the group consisting of acute muscle injury or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

8. The method of any one of embodiments 1 to 7, wherein the PGE2 derivative comprises 16,16-dimethyl prostaglandin E2.

9. The method of any one of embodiments 1 to 7, wherein the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1).

10. The method of any one of embodiments 1 to 9, wherein culturing the population of isolated muscle cells with the compound comprises acute, intermittent, or continuous exposure of the population of isolated muscle cells to the compound.

11. A method for promoting muscle cell engraftment in a subject, the method comprising:
   culturing a population of isolated muscle cells with an effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, to promote engraftment of the muscle cells in the subject; and
   administering the cultured muscle cells to the subject.

12. The method of embodiment 11, wherein the population of isolated muscle cells is purified.

13. The method of embodiment 11 or 12, wherein the population of isolated muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof.

14. The method of any one of embodiments 11 to 13, wherein the population of isolated muscle cells comprises muscle stem cells, satellite cells, myocytes, myoblasts, myotubes, myofibers, or a combination thereof.

15. The method of any one of embodiments 11 to 14, wherein the population of isolated muscle cells is autologous to the subject.

16. The method of any one of embodiments 11 to 14, wherein the population of isolated muscle cells is allogeneic to the subject.

17. The method of any one of embodiments 11 to 16, wherein the subject has a condition or disease associated with muscle damage, injury, or atrophy.

18. The method of embodiment 17, wherein the condition or disease associated with muscle damage, injury, or atrophy is selected from the group consisting of acute muscle injury or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

19. The method of any one of embodiments 11 to 18, wherein the PGE2 derivative comprises 16,16-dimethyl prostaglandin E2.

20. The method of any one of embodiments 11 to 18, wherein the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1).

21. The method of any one of embodiments 11 to 20, wherein culturing the population of isolated muscle cells with the compound comprises acute, intermittent, or continuous exposure of the population of isolated muscle cells to the compound.

22. A composition comprising a population of isolated muscle cells and a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof.

23. The composition of embodiment 22, wherein the population of isolated muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof.

24. The composition of embodiment 22 or 23, wherein the population of isolated muscle cells comprises muscle stem cells, satellite cells, myocytes, myoblasts, myotubes, myofibers, or a combination thereof.

25. The composition of any one of embodiments 22 to 24, further comprising a pharmaceutically acceptable carrier.

26. A kit comprising the composition of any one of embodiments 22 to 25, and an instruction manual.

27. A method for regenerating a population of muscle cells in a subject having a condition or disease associated with muscle damage, injury, or atrophy, the method comprising:
administering to the subject a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, to increase the population of muscle cells and/or to enhance muscle function in the subject.

28. The method of embodiment 27, wherein the condition or disease associated with muscle damage, injury, or atrophy is selected from the group consisting of acute muscle injury or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

29. The method of embodiment 27 or 28, wherein the population of muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof.

30. The method of any one of embodiments 27 to 29, wherein the population of muscle cells comprises muscle stem cells, satellite cells, myocytes, myoblasts, myotubes, myofibers, or a combination thereof.

31. The method of any one of embodiments 27 to 30, wherein the PGE2 derivative comprises 16,16-dimethyl prostaglandin E2.

32. The method of any one of embodiments 27 to 30, wherein the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1).

33. The method of any one of embodiments 27 to 32, wherein administering the compound comprises oral, intraperitoneal, intramuscular, intra-arterial, intradermal, subcutaneous, intravenous, or intracardiac administration.

34. The method of any one of embodiments 27 to 33, wherein the compound is administered in accordance with an acute regimen.

35. The method of any one of embodiments 27 to 34, wherein administering further comprises administering a population of isolated muscle cells to the subject.

36. The method of embodiment 35, wherein the population of isolated muscle cells is autologous to the subject.

37. The method of embodiment 35, wherein the population of isolated muscle cells is allogeneic to the subject.

38. The method of any one of embodiments 35 to 37, wherein the population of isolated muscle cells is purified.

39. The method of any one of embodiments 35 to 38, wherein the population of isolated muscle cells is cultured with the compound prior to being administered to the subject.

40. The method of embodiment 39, wherein culturing the population of isolated muscle cells with the compound comprises acute, intermittent, or continuous exposure of the population of isolated muscle cells to the compound.

41. The method of any one of embodiments 35 to 40, wherein administering the population of isolated muscle cells comprises injecting or transplanting the cells into the subject.

42. The method of any one of embodiments 35 to 41, wherein the population of isolated muscle cells and the compound are administered to the subject concomitantly.

43. The method of any one of embodiments 35 to 41, wherein the population of isolated muscle cells and the compound are administered to the subject sequentially.

44. A method for preventing or treating a condition or disease associated with muscle damage, injury or atrophy in a subject in need thereof, the method comprising:
   administering to the subject (i) a therapeutically effective amount of a compound selected from the group consisting of prostaglandin E2 (PGE2), a PGE2 prodrug, a PGE2 receptor agonist, a compound that attenuates PGE2 catabolism, a compound that neutralizes PGE2 inhibition, a derivative thereof, an analog thereof, and a combination thereof, and a pharmaceutically acceptable carrier, and (ii) a population of isolated muscle cells, to prevent or treat the condition or disease associated with muscle damage, injury, or atrophy.

45. The method of embodiment 44, wherein the PGE2 derivative comprises 16,16-dimethyl prostaglandin E2.

46. The method of embodiment 44, wherein the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PTG or SLCO2A1).

47. The method of any one of embodiments 44 to 46, wherein the population of isolated muscle cells comprises skeletal muscle cells, smooth muscle cells, cardiac muscle cells, embryonic stem cell-derived muscle cells, induced pluripotent stem cell-derived muscle cells, dedifferentiated muscle cells, or a combination thereof.

48. The method of any one of embodiments 44 to 47, wherein the population of isolated muscle cells comprises muscle stem cells, satellite cells, myoblasts, myocytes, myotubes, myofibers, or a combination thereof.

49. The method of any one of embodiments 44 to 48, wherein the population of isolated muscle cells is purified.

50. The method of any one of embodiments 44 to 49, wherein the population of isolated muscle cells is cultured with the compound prior to being administered to the subject.

51. The method of embodiment 50, wherein culturing the population of isolated muscle cells with the compound comprises acute, intermittent, or continuous exposure of the population of isolated muscle cells to the compound.

52. The method of any one of embodiments 44 to 51, wherein the population of isolated muscle cells is autologous to the subject.

53. The method of any one of embodiments 44 to 51, wherein the population of isolated muscle cells is allogeneic to the subject.

54. The method of any one of embodiments 44 to 53, wherein administering the compound comprises oral, intraperitoneal, intramuscular, intra-arterial, intradermal, subcutaneous, intravenous, or intracardiac administration.

55. The method of any one of embodiments 44 to 54, wherein the compound is administered in accordance with an acute regimen.

56. The method of any one of embodiments 44 to 55, wherein administering the population of isolated muscle cells comprises injecting or transplanting the cells into the subject.

57. The method of any one of embodiments 44 to 56, wherein the compound and the population of isolated muscle cells are administered to the subject concomitantly.

58. The method of any one of embodiments 44 to 56, wherein the compound and the population of isolated muscle cells are administered to the subject sequentially.

59. The method of any one of embodiments 44 to 58, wherein the subject is suspected of having or at risk for developing the condition or disease associated with muscle damage, injury, or atrophy.

60. The method of any one of embodiments 44 to 59, wherein the condition or disease associated with muscle damage, injury or atrophy is selected from the group consisting of acute muscle injury or trauma, soft tissue hand injury, Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, and sarcopenia.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

```
Informal Sequence Listing
Gapdh, forward
                                    (SEQ ID NO: 1)
    5'-TTCACCACCATGGAGAAGGC-3'

Gapdh, reverse
                                    (SEQ ID NO: 2)
    5'-CCCTTTTGGCTCCACCCT-3'

Hpgd, forward
                                    (SEQ ID NO: 3)
    5'-TCCAGTGTGATGTGGCTGAC-3'

Hpgd, reverse
                                    (SEQ ID NO: 4)
    5'-ATTGTTCACGCCTGCATTGT-3'

Ptges, forward
                                    (SEQ ID NO: 5)
    5'-GCTGTCATCACAGGCCAGA-3'

Ptges, reverse
                                    (SEQ ID NO: 6)
    5'-CTCCACATCTGGGTCACTCC-3'

Ptges2, forward
                                    (SEQ ID NO: 7)
    5'-CTCCTACAGGAAAGTGCCCA-3'

Ptges2, reverse
                                    (SEQ ID NO: 8)
    5'-ACCAGGTAGGTCTTGAGGGC-3'
```

Ptger1, forward (SEQ ID NO: 9)
5' GTGGTGTCGTGCATCTGCT-3'

Ptger1, reverse (SEQ ID NO: 10)
5' CCGCTGCAGGGAGTTAGAGT-3'

Ptger2, forward (SEQ ID NO: 11)
5'-ACCTTCGCCATATGCTCCTT-3'

Ptger2, reverse (SEQ ID NO: 12)
5'-GGACCGGTGGCCTAAGTATG-3'

---

What is claimed is:

1. A method of treating muscle damage, muscle injury, or muscle atrophy in a subject having spinal muscular atrophy, said method comprising administering a composition comprising a 15-hydroxyprostaglandin dehydrogenase (15-PGDH) inhibitor to said subject in an amount effective to inhibit 15-PGDH, thereby treating said muscle damage, muscle injury, or muscle atrophy in said subject having spinal muscular atrophy.

2. The method of claim 1, wherein said administering is selected from the group consisting of: parenteral administration, intravenous administration, subcutaneous administration, intraperitoneal administration, intramuscular administration, intra-arterial administration, intravascular administration, intracardiac administration, intrathecal administration, intranasal administration, intradermal administration, intravitreal administration, transmucosal administration, oral administration, administration as a suppository, topical administration, and any combination thereof.

3. The method of claim 1, wherein said administering comprises oral administration.

4. The method of claim 1, wherein said composition is administered in accordance with an acute regimen.

5. The method of claim 1, wherein said composition is administered in accordance with an intermittent regimen.

6. The method of claim 1, wherein said composition is administered in accordance with a chronic regimen.

7. The method of claim 1, wherein said composition further comprises a pharmaceutically acceptable carrier.

* * * * *